US006420426B1

(12) United States Patent
Van Zandt

(10) Patent No.: US 6,420,426 B1
(45) Date of Patent: Jul. 16, 2002

(54) SUBSTITUTED PHENOXYACETIC ACIDS

(75) Inventor: Michael C. Van Zandt, Guilford, CT (US)

(73) Assignee: The Institute for Pharmaceutical Discovery LLC, Branford, CT (US)

( * ) Notice: Subject to any disclaimer, the term of this patent is extended or adjusted under 35 U.S.C. 154(b) by 0 days.

(21) Appl. No.: 09/603,817

(22) Filed: Jun. 23, 2000

Related U.S. Application Data

(60) Provisional application No. 60/141,068, filed on Jun. 25, 1999.

(51) Int. Cl.⁷ .......................... C07C 63/08; A61K 31/19
(52) U.S. Cl. ....................... 514/568; 562/405; 562/450; 562/455; 544/111; 544/359; 546/187; 546/192
(58) Field of Search ................................. 562/405, 450, 562/455; 544/111, 359; 546/187, 192; 514/568

(56) References Cited

U.S. PATENT DOCUMENTS

| 5,399,703 A | | 3/1995 | Yoshimoto et al. |
| 6,054,457 A | * | 4/2000 | Setoi et al. .................. 514/255 |

FOREIGN PATENT DOCUMENTS

| JP | 43 006936 B | 3/1968 |
| WO | WO 86/05779 | 10/1986 |
| WO | WO 94/08945 | 4/1994 |
| WO | WO 96/41795 | 12/1996 |

OTHER PUBLICATIONS

Drain D.J. et al., "Effects of substituing tetrazole for carboxyl in two series of antiinflammatory pehoxyacetic acids." J. Pharm., Pharmacol., vol. 23, No. 111, 1971, pp. 857–864.

Chen, Jichou et al., "Synthesis of carboxyphenoxyacetic acid derivatives using liquid–liquid phase transfer catalysis." retrived from STN Database accession No. 116:151263. XP–002153085.

* cited by examiner

*Primary Examiner*—Floyd D. Higel
*Assistant Examiner*—Andrea Small
(74) *Attorney, Agent, or Firm*—McDonnell Boehnen Hulbert & Berghoff

(57) ABSTRACT

Disclosed are substituted phenoxyacetic acids useful in the treatment of chronic complications arising from diabetes mellitus. Also disclosed are pharmaceutical compositions containing the compounds, alone or in combination with other therapeutic agents, and methods of treatment employing the compounds and pharmaceutical compositions, as well as methods for their synthesis.

30 Claims, No Drawings

SUBSTITUTED PHENOXYACETIC ACIDS

This application claims priority from U.S. Provisional Application No. 60/141,068 filed on Jun. 25, 1999, which is hereby incorporated by reference in its entirety.

BACKGROUND OF THE INVENTION

1. Field of the Invention

This invention relates to substituted phenoxy acetic acids and pharmaceutical compositions containing such compounds. It also relates to the use of such compounds in the treatment or prevention of chronic complications arising from diabetes mellitus.

2. Description of the Related Art

The use of aldose reductase inhibitors (ARIs) for the treatment of chronic diabetic complications is well known. The complications arise from elevated levels of glucose in tissues such as the nerve, kidney, retina and lens that enters the polyol pathway and is converted to sorbitol via aldose reductase. Because sorbitol does not easily cross cell membranes, it accumulates inside certain cells resulting in changes in osmotic pressure, alterations in the redox state of pyridine nucleotides (i.e. increased NADH/NAD$^+$ ratio) and depleted intracellular levels of myoinositol. These biochemical changes, which have been linked to diabetic complications, can be controlled by inhibitors of aldose reductase.

The use of aldose reductase inhibitors for the treatment of chronic diabetic complications has been extensively reviewed, see: (a) *Textbook of Diabetes*, 2$^{nd}$ ed.; Pickup, J. C. and Williams, G. (Eds.); Blackwell Science, Boston, Mass. 1997.; (b) Larson, E. R.; Lipinski, C. A. and Sarges, R., *Medicinal Research Reviews*, 1988, 8 (2), 159–198; (c) Dvornik, D. *Aldose Reductase Inhibition*. Porte, D. (ed), Biomedical Information Corp., New York, N.Y. Mc Graw Hill 1987; (d) Petrash, J. M., Tarle, I., Wilson, D. K. Quiocho. F. A. Perspectives in Diabetes, *Aldose Reductase Catalysis and Crystalography: Insights From Recent Advances in Enzyme Structure and Function, Diabetes*, 1994, 43, 955; (e) Aotsuka, T.; Abe, N.; Fukushima, K.; Ashizawa, N. and Yoshida, M., *Bioorg. & Med. Chem. Letters*, 1997, 7, 1677, (f), T., Nagaki, Y.; Ishii, A.; Konishi, Y.; Yago, H; Seishi, S.; Okukado, N.; Okamoto, K., *J. Med. Chem.*, 1997, 40, 684; (g) Ashizawa, N.; Yoshida, M.; Sugiyama, Y.; Akaike, N.; Ohbayashi, S.; Aotsuka, T.; Abe, N.; Fukushima, K.; Matsuura, A, *Jpn. J. Pharmacol.* 1997, 73, 133; (h) Kador, P. F.; Sharpless, N. E., *Molecular Pharmacology*, 1983, 24, 521; (I) Kador, P. F.; Kinoshita, J. H.; Sharpless, N. E., *J. Med. Chem.* 1985, 28 (7), 841; (j) Hotta, N., *Biomed. & Pharmacother.* 1995, 5, 232; (k) Mylar, B.; Larson, E. R.; Beyer, T. A.; Zembrowski, W. J.; Aldinger, C. E.; Dee, F. D.; Siegel, T. W.; Singleton, D. H., *J. Med. Chem.* 1991, 34, 108; (l) Dvornik, D. *Croatica Chemica Acta* 1996, 69 (2), 613.

The following patents disclose compounds said to have activity as aldose reductase inhibitors: U.S. Pat. Nos. 5,700,819; 4,868,301; and 4,734,419. Although many aldose reductase inhibitors have been extensively developed, none have demonstrated sufficient efficacy in human clinical trials without significant undesirable side effects. Thus no aldose reductase inhibitors are currently available as approved therapeutic agents in the United States, and consequently, there is still a significant need for new, efficacious and safe medications for the treatment of diabetic complications.

SUMMARY OF THE INVENTION

This invention provides compounds that interact with and inhibit aldose reductase. Thus, in a broad aspect, the invention provides compounds of Formula I:

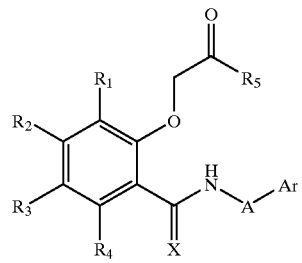

I or pharmaceutically acceptable salts thereof wherein

A is a covalent bond, $C_1$–$C_4$ alkylene group optionally substituted with $C_1$–$C_2$ alkyl or mono- or disubstituted with halogen, preferably fluoro or chloro;

X is oxygen, sulfur or $NR_6$, wherein each $R_6$ is hydrogen, cyano or an alkyl group of 1–6 carbon atoms (which may be substituted with one or more halogens);

$R_1$, $R_2$, $R_3$ and $R_4$ are each independently hydrogen, halogen, nitro, or an alkyl group of 1–6 carbon atoms (which may be substituted with one or more halogens);

$OR_7$, $SR_7$, $S(O)R_7$, $S(O)_2R_7$, $C(O)N(R_7)_2$, or $N(R_7)_2$, wherein each $R_7$ is independently hydrogen, an alkyl group of 1–6 carbon atoms (which may be substituted with one or more halogens) or benzyl, where the phenyl portion is optionally substituted with up to three groups independently selected from halogen, $C_1$–$C_6$ alkyl, $C_1$–$C_6$ alkoxy, amino, and mono- or di($C_1$–$C_6$)alkylamino;

phenyl or heteroaryl such as 2-, 3- or 4-imidazolyl or 2-, 3-, or 4-pyridyl, each of which phenyl or heteroaryl is optionally substituted with up to three groups independently selected from halogen, $C_1$–$C_6$ alkyl, $C_1$–$C_6$ alkoxy, amino, and mono- or di($C_1$–$C_6$) alkylamino;

phenoxy where the phenyl portion is optionally substituted with up to three groups independently selected from halogen, $C_1$–$C_6$ alkyl, $C_1$–$C_6$ alkoxy, amino, and mono- or di($C_1$–$C_6$)alkylamino; or a group of the formula

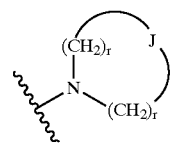

where

J is a bond, $CH_2$, oxygen, or nitrogen; and each r is independently 2 or 3;

$R_5$ is hydroxy or a prodrug group; and

Ar represents aryl or heteroaryl, each of which is optionally substituted with up to five groups.

In another aspect, the invention provides methods for preparing such compounds.

The compounds of the invention inhibit aldose reductase. Since aldose reductase is critical to the production of high levels of sorbitol in individuals with diabetes, inhibitors of aldose reductase are useful in preventing and/or treating various complications associated with diabetes. The compounds of the invention are therefore effective for the treatment of diabetic complications as a result of their ability to inhibit aldose reductase.

Thus, in another aspect, the invention provides methods for treating and/or preventing chronic complications associated with diabetes mellitus, including, for example, diabetic cataracts, retinopathy, nephropathy, and neuropathy.

In another aspect, the invention provides methods for treating and/or preventing chronic complications associated with diabetes mellitus, including, for example, diabetic cataracts, retinopathy, keratopathy, wound healing, diabetic uveitis, diabetic cardiomyopathy, nephropathy, and neuropathy.

The compounds of the invention promote healing of wounds in mammals. In preferred aspects, the compounds are useful in promoting wound healing in diabetic mammals. Thus, the compounds of the invention may be employed in the treatment of wounds in mammals, preferably humans, more preferably in diabetic humans.

In still another aspect, the invention provides for the use of a compound or compounds of Formula I for the preparation of a medicament for the treatment of any of the disorders or diseases (a) listed above or (b) connected with diabetic complications.

Prolonged administration of an ACE inhibitor at a therapeutically effective dose may be deleterious or give rise to side effects in certain patients, for example, it may lead to significant deterioration of renal function, induce hyperkalemia, neutropenia, angioneurotic oedema, rash or diarrhea or give rise to a dry cough. The present invention provides combination therapy comprising administration of a compound of Formula I together with a vasodilator, preferably an ACE inhibitor. Such administration decreases the likelihood of problems associated with administration of vasodilators such as ACE inhibitors that otherwise may result from administration of one of these agents alone. Furthermore, diabetic complications involve a complex mechanism or number of mechanisms, which initiate a cascade of biochemical alternations that in turn lead to structural changes. These may result in a diverse patient population. The present invention, therefore, provides the additional advantage that it allows tailoring of treatment to the needs of a particular patient population.

In this aspect, the present invention provides a pharmaceutical composition which comprises a compound of Formula I and vasodilator, preferably an ACE inhibitor, together with a pharmaceutically acceptable carrier and/or diluent. In addition, the invention contemplates methods of treating diseases or disorders associated with elevated plasma levels of glucose, including complications associated with diabetes and hypertension and/or, congestive heart failure. These methods comprise administering an effective amount of a compound of Formula I in combination with a vasodilating compound, preferably an ACE inhibitor, to a patient in need of such treatment, e.g., a patient suffering from diabetes or hypertension or a patient likely to contract either of those diseases.

In a related aspect, the invention provides methods for the treatment, prevention or reversal of the development of disease conditions associated with impaired neuronal conduction velocity. These methods comprise administering to a patient suffering from or prone to develop such disease conditions an effective amount of a compound of Formula I together with an effective amount of a vasodilating compound, such as for example, an angiotensin converting enzyme inhibitor.

Further, the invention provides methods for the treatment or prevention of diabetic neuropathy comprising administering to a patient suffering from or prone to develop such complications an effective amount of a compound of Formula I.

In still another aspect, the invention provides pharmaceutical compositions containing compounds of Formula I.

In yet another aspect, the invention provides intermediates useful for preparing the compounds of Formula I as well as synthetic methods for making such compounds and intermediates.

DETAILED DESCRIPTION OF THE INVENTION

The numbering system for the compounds of Formula I is as follows:

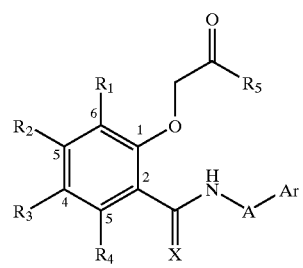

I

As noted above, the invention provides novel substituted phenoxyacetic acids useful in treating and/or preventing complications associated with or arising from elevated levels of glucose in individuals suffering from diabetes mellitus. These compounds are represented by Formula I above.

In preferred compounds of Formula I, as well as in compounds of Formulas II and III, X is oxygen.

In compounds of Formula I, the aryl and heteroaryl groups represented by Ar include:

phenyl where
  (i) the phenyl group is optionally substituted with up to 3 groups independently selected from halogen, an alkyl group of 1–6 carbon atoms (which may be substituted with one or more halogens), nitro, $OR_7$, $SR_7$, $S(O)R_7$, $S(O)_2R_7$ or $N(R_7)_2$ wherein $R_7$ is hydrogen, an alkyl group of 1–6 carbon atoms (which may be substituted with one or more halogens) or benzyl, where the phenyl portion is optionally substituted with up to three groups independently selected from halogen, $C_1-C_6$ alkyl, $C_1-C_6$ alkoxy, amino, and mono- or di($C_1-C_6$) alkylamino;
  (ii) the phenyl group is optionally monosubstituted as described above in (i) and disubstituted with a $C_1-C_5$ alkylene group forming a cycloalkyl ring fused to the phenyl where the $C_1-C_5$ alkylene group is optionally further mono- or disubstituted with hydroxy, halogen, $C_1-C_2$ alkyl, $C_1-C_2$ alkoxy, amino or mono- or di($C_1-C_2$)alkyl amino and where the $C_1-C_5$ alkylene group optionally contains one or two hetero atoms selected from oxygen, nitrogen and sulfur; or (iii) the phenyl group is optionally substituted with up to 3 groups as described above in (i) and further condensed with benzo where the benzo is optionally substituted with one or two of halogen, cyano, nitro, trifluoromethyl, perfluoroethyl, trifluoroacetyl, or ($C_1$–$C_6$)alkanoyl, hydroxy, ($C_1$–$C_6$)alkyl, ($C_1$–$C_6$) alkoxy, ($C_1$–$C_6$)alkylthio, trifluoromethoxy, trifluoromethylthio, ($C_1$–$C_6$)alkylsulfinyl, ($C_1$–$C_6$) alkylsulfonyl;

a heterocyclic 5-membered ring having one nitrogen, oxygen or sulfur, two nitrogens one of which may be replaced by oxygen or sulfur, or three nitrogens one of which may be replaced by oxygen or sulfur, said heterocyclic 5-membered ring substituted by one or two fluoro, chloro, ($C_1$–$C_6$)alkyl or phenyl, or condensed with benzo, or substituted by one of pyridyl, furyl or thienyl, said phenyl or benzo optionally substituted by one of iodo, cyano, nitro, perfluoroethyl, trifluoroacetyl, or ($C_1$–$C_6$)alkanoyl, one or two of fluoro, chloro, bromo, hydroxy, ($C_1$–$C_6$)alkyl, ($C_1$–$C_6$) alkoxy, ($C_1$–$C_6$)alkylthio, trifluoromethoxy, trifluoromethylthio, ($C_1$–$C_6$)alkylsulfinyl, ($C_1$–$C_6$) alkylsulfonyl or trifluoromethyl, or two fluoro or two trifluoromethyl with one hydroxy or one ($C_1$–$C_6$) alkoxy, or one or, preferably, two fluoro and one trifluoromethyl, or three fluoro, said pyridyl, furyl or thienyl optionally substituted in the 3-position by fluoro, chloro, bromo, ($C_1$–$C_6$)alkyl or ($C_1$–$C_6$)alkoxy;

a heterocyclic 6-membered ring having one to three nitrogen atoms, or one or two nitrogen atoms and one oxygen or sulfur, said heterocyclic 6-membered ring substituted by one or two ($C_1$–$C_6$)alkyl or phenyl, or condensed with benzo, or substituted by one of pyridyl, furyl or thienyl, said phenyl or benzo optionally substituted by one of iodo or trifluoromethylthio, or one or two of fluoro, chloro, bromo, ($C_1$–$C_6$)alkyl, ($C_1$–$C_6$) alkoxy, ($C_1$–$C_6$)alkylthio, ($C_1$–$C_6$)alkylsulfinyl, ($C_1$–$C_6$)alkylsulfonyl, or trifluoromethyl, and said pyridyl, furyl or thienyl optionally substituted in the 3-position by fluoro, chloro, ($C_1$–$C_6$)alkyl or ($C_1$–$C_6$) alkoxy;

said benzo-condensed heterocyclic 5-membered or 6-membered rings optionally substituted in the heterocyclic 5-membered or 6-membered ring by one of fluoro, chloro, bromo, methoxy, or trifluoromethyl;

oxazole or thiazole condensed with a 6-membered aromatic group containing one or two nitrogen atoms, with thiophene or with furane, each optionally substituted by one of fluoro, chloro, bromo, trifluoromethyl, methylthio or methylsulfinyl;

imidazolopyridine or triazolopyridine optionally substituted by one of trifluoromethyl, trifluoromethylthio, bromo, or $C_1$–$C_6$ alkoxy, or two of fluoro or chloro;

thienothiophene or thienofuran optionally substituted by one of fluoro, chloro or trifluoromethyl; thienotriazole optionally substituted by one of chloro or trifluoromethyl;

naphthothiazole; naphthoxazole; or thienoisothiazole.

The heterocyclic 5-membered and 6-membered rings are optionally monosubstituted as described above and may be further disubstituted with a $C_1$–$C_5$ alkylene group forming a cycloalkyl ring fused to the heterocyclic ring where the $C_1$–$C_5$ alkylene group is optionally further mono- or disubstituted with hydroxy, halogen, $C_1$–$C_2$ alkyl, $C_1$–$C_2$ alkoxy, amino or mono- or di($C_1$–$C_2$)alkyl amino and where the $C_1$–$C_5$ alkylene group optionally contains one or two hetero atoms selected from oxygen, nitrogen and sulfur.

More specific compounds of the invention are those of Formula I wherein Ar is optionally substituted benzothiazolyl, benzoxazolyl, isoquinolyl, benzothiophen-yl, benzofuran-yl or benzimidazolyl, or substituted oxadiazolyl or indolyl. Other more specific compounds are of Formula I those wherein, A is a covalent bond or $CH_2$, $R_5$ is hydroxy, and each of $R_1$–$R_4$ are independently hydrogen, halogen, more preferably bromo, chloro or fluoro, $C_1$–$C_6$, more preferably, $C_1$–$C_2$ alkyl, phenoxy, benzyloxy, or $C_1$–$C_6$, more preferably, $C_1$–$C_2$ alkoxy. In the compounds of Formula I, $R_1$ and $R_4$ are more preferably hydrogen or $C_1$–$C_3$ alkyl, most preferably. hydrogen. Also, the more preferred compounds of Formula I are those where $R_2$ and $R_3$ are independently hydrogen, halogen, more preferably chloro or fluoro, $C_1$–$C_6$ alkyl, more preferably methyl or ethyl, $C_1$–$C_6$ alkoxy, more preferably methoxy or ethoxy, amino, mono or di($C_1$–$C_3$)alkylamino, morpholinyl, piperidin-1-yl, or piperazin-1-yl.

Preferred compounds of the invention are those wherein A is methylene, $R_5$ is hydroxy, Ar is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, benzothiophen-2-yl, benzofuran-2-yl, or thazolo[4,5-pyridine-2-y, thieno[2,3-b]pyridine2-yl, imidazo[1,5-a]pyridine-2-yl, or indol-2-yl, or substituted 1,2,4-oxadiazol-3-yl, 1,2,4-oxadiazol-5-yl, isothiazol-5-yl, isothiazol-4-yl, 1,3,4-oxadiazol-5-yl, 1,2,5-thiadiazol-3-yl, oxazol-2-yl, thiazol-2-yl, or thiazol-4-yl, $R_1$–$R_4$ are independently hydrogen, halogen, more preferably bromo, chloro or fluoro, $C_1$–$C_2$ alkyl, phenoxy, benzyloxy or phenyl where each phenyl portion is optionally substituted with $C_1$–$C_6$ alkyl, halogen, $C_1$–$C_6$ alkoxy, hydroxy, amino or mono- or di ($C_1$–$C_6$) alkylamino. Preferably, $R_1$ and $R_4$ in the compounds of the invention are hydrogen or $C_1$–$C_3$ alkyl, more preferably hydrogen.

Other more specific compounds of the invention are those wherein A is methylene, $R_5$ is hydroxy, Ar is optionally 4,5,6 or 7 benzo-substituted benzothiazolyl, benzoxazolyl, benzimidazolyl, benzothiophenyl, benzofuranyl, or indolyl, or Ar is 2-benzothiazolyl substituted on benzo by one trifluoroacetyl or trifluoromethylthio, or one or two of fluoro chloro, bromo, hydroxy, methyl, methoxy, trifluoromethyl, trifluoromethoxy, trifluoromethylthio, or one or, preferably, two fluoro and one trifluoromethyl, or two fluoro or two trifluoromethyl with one methoxy, or three fluoro, or by 6,7-benzo. Preferably, $R_1$ and $R_4$ in the compounds of the invention are hydrogen or $C_1$–$C_3$ alkyl, more preferably hydrogen.

Preferred compounds of the invention include those where Ar in Formula I is substituted phenyl, i.e., compounds of Formula II:

II

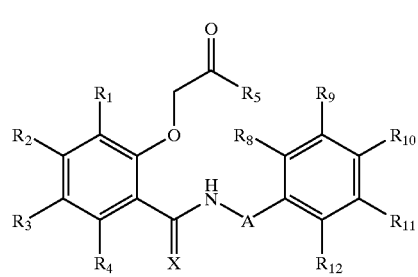

wherein
A is a $C_1$–$C_4$ alkylene group optionally substituted with $C_1$–$C_2$ alkyl;

X is oxygen, sulfur or $NR_6$, wherein each $R_6$ is hydrogen, cyano or an alkyl group of 1–6 carbon atoms (which may be substituted with one or more halogens);

$R_1$, $R_2$, $R_3$ and $R_4$ are each independently hydrogen, halogen, an alkyl group of 1–6 carbon atoms (which may be substituted with one or more halogens), nitro, $OR_7$, $SR_7$, $S(O)R_7$, $S(O)_2NR_7$, $C(O)N(R_7)_2$, or $N(R_7)_2$, wherein each $R_7$ is independently hydrogen, an alkyl group of 1–6 carbon atoms (which may be substituted with one or more halogens) or benzyl, where the phenyl portion is optionally substituted with up to three groups independently selected from halogen, $C_1$–$C_6$ alkyl, $C_1$–$C_6$ alkoxy, amino, and mono- or di($C_1$–$C_6$) alkylamino;

phenyl or heteroaryl such as 2-, 3- or 4-imidazolyl or 2-, 3-, or 4-pyridyl, each of which phenyl or heteroaryl is optionally substituted with up to three groups independently selected from halogen, $C_1$–$C_6$ alkyl, $C_1$–$C_6$ alkoxy, amino, and mono- or di($C_1$–$C_6$) alkylamino;

phenoxy where the phenyl portion is optionally substituted with up to three groups independently selected from halogen, $C_1$–$C_6$ alkyl, $C_1$–$C_6$ alkoxy, amino, and mono- or di($C_1$–$C_6$)alkylamino; or a group of the formula

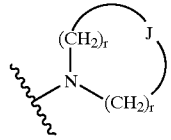

where

J is a bond, $CH_2$, oxygen, or nitrogen; and each r is independently 2, or 3;

$R_5$ is hydroxy, an alkoxy group of 1–6 carbon atoms, or —O—M+ where M+ is a cation forming a pharmaceutically acceptable salt; and $R_8$, $R_9$, $R_{10}$, $R_{11}$, and $R_{12}$ in combination, represent hydrogen, or 1–3 groups selected from fluorine, chlorine, bromine, trifluoromethyl or nitro.

Other preferred compounds of the invention are those where Ar is a substituted benzothiazole, i.e., compounds of Formula III:

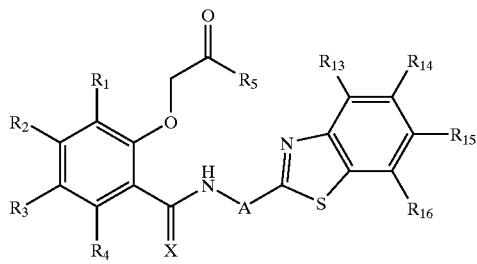

wherein

A is a covalent bond, $C_1$–$C_4$ alkylene group optionally substituted with $C_1$–$C_2$ alkyl;

X is oxygen, sulfur or $NR_6$, wherein each $R_6$ is hydrogen, cyano or an alkyl group of 1–6 carbon atoms (which may be substituted with one or more halogens);

$R_1$, $R_2$, $R_3$ and $R_4$ are each independently hydrogen, halogen, an alkyl group of 1–6 carbon atoms (which may be substituted with one or more halogens), nitro, $OR_7$, $SR_7$, $S(O)R_7$, $S(O)_2NR_7$, $C(O)N(R_7)_2$ or $N(R_7)_2$, wherein each $R_7$ is independently hydrogen, an alkyl group of 1–6 carbon atoms (which may be substituted with one or more halogens) or benzyl, where the phenyl portion is optionally substituted with up to three groups independently selected from halogen, $C_1$–$C_6$ alkyl, $C_1$–$C_6$ alkoxy, amino, and mono- or di($C_1$–$C_6$) alkylamino;

phenyl or heteroaryl such as 2-, 3- or 4-imidazolyl or 2-, 3-, or 4-pyridyl, each of which phenyl or heteroaryl is optionally substituted with up to three groups independently selected from halogen, $C_1$–$C_6$ alkyl, $C_1$–$C_6$ alkoxy, amino, and mono- or di($C_1$–$C_6$) alkylamino;

phenoxy where the phenyl portion is optionally substituted with up to three groups independently selected from halogen, $C_1$–$C_6$ alkyl, $C_1$–$C_6$ alkoxy, amino, and mono- or di($C_1$–$C_6$)alkylamino; or a group of the formula

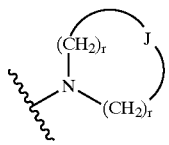

where

J is a bond, $CH_2$, oxygen, or nitrogen; and each r is independently 2 or 3;

$R_5$ is hydroxy, $C_1$–$C_6$ alkoxy, or —O⁻M+ where M+ is a cation forming a pharmaceutically acceptable salt; and $R_{13}$, $R_{14}$, $R_{15}$ and $R_{16}$ are independently hydrogen, halogen, nitro, hydroxy, $C_1$–$C_6$ alkyl, $C_1$–$C_6$ alkoxy, $C_1$–$C_6$ alkylthio, trifluoromethyl, trifluoromethoxy, $C_1$–$C_6$ alkylsulfinyl, or $C_1$–$C_6$ alkylsulfonyl.

In preferred compounds of Formula III, the $R_{13}$, $R_{14}$, $R_{15}$ and $R_{16}$ substituents, in combination, represent one of bromo, cyano or nitro, one or two of fluoro, chloro, hydroxy, ($C_1$–$C_6$)alkyl, ($C_1$–$C_6$) alkoxy, or trifluoromethyl, or two fluoro or two methyl with one hydroxy or one ($C_1$–$C_6$) alkoxy, or one of, preferably, two fluoro and one methyl, or three fluoro groups. Particularly preferred $R_{13}$, $R_{14}$, $R_{15}$ and $R_{16}$ substituents are, independently, fluorine, chlorine, nitro, and trifluoromethyl.

In preferred compounds of Formulas II and III, A is preferably methylene, methylene substituted with a methyl group, or ethylene.

Preferred compounds according to Formula II above include those wherein $R_8$ is fluorine, $R_{10}$ is bromine and $R_9$, $R_{11}$ and $R_{12}$ are hydrogens; or those wherein $R_8$, $R_{10}$, $R_{11}$ and $R_{12}$ are hydrogens and $R_9$ is nitro. Other preferred compounds of Formula II include those where $R_2$ and $R_3$ are independently hydrogen, halogen, more preferably chloro or fluoro, $C_1$–$C_6$ alkyl, more preferably methyl or ethyl, alkoxy, more preferably methoxy or ethoxy, amino, mono or di($C_1$–$C_3$ alkyl)amino, morpholinyl, piperidin-1-yl, or piperazin-1-yl; $R_8$ is fluorine, $R_{10}$ is bromine and $R_9$, $R_{11}$ and $R_{12}$ are hydrogens; or those wherein $R_2$ and $R_3$ are independently hydrogen, halogen, more preferably chloro or fluoro, $C_1$–$C_6$ alkyl, more preferably methyl or ethyl, alkoxy, more preferably methoxy or ethoxy, amino, mono or di($C_1$–$C_3$ alkyl)amino, morpholinyl, piperidin-1-yl, or piperazin-1-yl; $R_8$ $R_{10}$, $R_{11}$ and $R_{12}$ are hydrogens, and $R_9$ is nitro.

Preferred compounds of Formula III above are those wherein the benzothiazole moiety is substituted with nitro, one, two, or three of fluoro, one or two of chloro, or one trifluoromethyl group. More preferred compounds of Formula II are those where A is methylene, and $R_5$ is hydroxy or $C_1$–$C_6$ alkoxy. Other more preferred compounds of III are those where $R_2$ and $R_3$ are independently hydrogen, halogen, more preferably chloro or fluoro, $C_1$–$C_6$ alkyl, more preferably methyl or ethyl, alkoxy, more preferably methoxy or ethoxy, amino, mono or di($C_1$–$C_3$ alkyl)amino, morpholinyl, piperidin-1-yl, or piperazin-1-yl.

Still more preferred compounds of Formula III are those wherein $R_{13}$, $R_{14}$ and $R_{16}$ are fluorines and $R_{15}$ is hydrogen.

The term "prodrug group" denotes a moiety that is converted in vivo into the active compound of formula I wherein $R_5$ is hydroxy. Such groups are generally known in the art and include ester forming groups, to form an ester prodrug, such as benzyloxy, di($C_1$–$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$–$C_8$), preferably $C_1$–$C_6$, more preferably $C_1$–$C_3$, alkoxy optionally substituted by N-morpholino and amide-forming groups such as di($C_1$–$C_6$)alkylamino. Preferred prodrug groups include $C_1$–$C_6$ alkoxy most preferably $C_1$–$C_2$ alkoxy, and $O^-M^+$ where $M^+$ represents a cation. Preferred cations include sodium, potassium, ammonium, magnesium and calcium. Where M is a divalent cation such as magnesium or calcium it will be understood that such cations will be associated with more than one, generally two, carboxylate anions formed by the compound of formula I.

In certain situations, compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained as pure compounds or in enantiomeric excess, by asymmetric synthesis or by resolution of the racemates. Resolution of the racemates can be accomplished, for example, by conventional methods such as crystallization in the presence of a resolving agent, or chromatography, using, for example, a chiral HPLC column.

Representative compounds of the present invention include the pharmaceutically acceptable acid addition salts of compounds where $R_5$ includes basic nitrogen atom, i.e, an alkylamino or morpholino group. In addition, if the compound or prodrug of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Non-toxic pharmaceutical base addition salts include salts of bases such as sodium, potassium, calcium, ammonium, magnesium, and the like. Those skilled in the art will recognize a wide variety of non-toxic pharmaceutically acceptable addition salts.

As used herein, the terms 2-benzothiazolyl and benzothiazol-2-yl are synonymous.

Representative groups of the formula

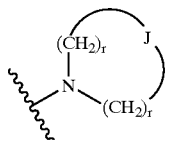

include those where J is oxygen and each r is 2 (morpholinyl), J is nitrogen and each r is 2 (piperazinyl) or one r is 2 and the other 3 (homopiperazinyl), or J is $CH_2$ and each r is 2 (piperidinyl) or one r is 2 and the other 3 (homopiperidinyl). Preferred groups of this formula are morpholinyl and piperazinyl. Any of these groups may optionally be substituted on a carbon atom with $C_1$–$C_6$ alkyl.

The heterocyclic 5-membered ring having one to three nitrogen atoms, one of which may be replaced by oxygen or sulfur includes imidazolyl, oxazolyl, thiazolyl, pyrazolyl, oxadiazolyl, thiadiazolyl, and triazolyl.

The heterocyclic 6-membered ring having one to three nitrogen atoms, or one or two nitrogen atoms and one oxygen or sulfur includes triazinyl, pyrimidyl, pyridazinyl, oxazinyl and triazinyl.

The heterocyclic ring may be condensed with benzo so that said ring is attached at two neighboring carbon atoms to form a phenyl group. Such benzoheterocyclic ring may be attached to A either through the heterocyclic group or through the benzo group of the benzoheterocyclic ring. Representative examples of compounds wherein said heterocyclic ring is condensed with a benzo include benzoxazolyl, quinazolin-2-yl, 2-benzimidazolyl, quinazolin-4-yl and benzothiazolyl. The oxazole or thiazole condensed with a 6-membered aromatic group containing one or two nitrogen atoms include positional isomers such as oxazolo[4,5-b]pyridine-2-yl, thiazolo[4,5-b]pyridine-2-yl, oxazolo[4,5-c]pyridine-2-yl, thiazolo[4,5-c]pyridine-2-yl, oxazolo[5,4-b]pyridine-2-yl, thiazolo[5,4-b]pyridine-2-yl, oxazolo[5,4-c]pyridine-2-yl, and thiazolo[5,4-c]pyridine-2-yl. The 5- or 6-membered heterocyclic rings are preferably covalently bonded to the A group by a carbon atom in the heterocyclic ring, and more preferably by a carbon atom between 2 hetero atoms.

By "heteroaryl" is meant an aromatic ring system comprising one, two or three rings of 5-, 6-, 7-, or 8-atoms per ring wherein at least one aromatic ring contains at least one and up to four heteroatoms selected from nitrogen, oxygen, or sulfur. Such heteroaryl groups include, for example, thienyl, furanyl, thiazolyl, imidazolyl, isoxazolyl, oxazolyl, pyridyl, pyrimidinyl, isoquinolinyl, quinolinyl, napthyridinyl, benzothiazolyl, benzimidazolyl, and benzoxazolyl. Preferably, the heteroaryl group is attached to the parent molecular moiety through a carbon atom in the heteroaryl group. Where the heteroaryl group is connected to the parent moiety through a nitrogen, the adjacent X group will be an alkylene group. Preferred heteroaryl groups are monocyclic where the ring has 5 or 6 members and contains 1 or 2 nitrogen atoms, or bicyclic, where one ring has 5 or 6 members and contains 1 or 2 nitrogen atoms and the second ring has 5, 6, or 7 members and contains 0, 1, or 2 nitrogen atoms. Preferred heteroaryl groups are benzimidazolyl, imidazopyridinyl, benzothiazolyl, and imidazopyrazinyl.

The following compounds of the invention are provided to give the reader an understanding of the compounds encompassed by the invention:

[2-(4-Bromo-2-fluoro-benzylcarbamoyl)-5-chloro-phenoxy]-acetic acid

[5-Chloro-2-(3-trifluoromethyl-benzylcarbamoyl)-phenoxy]-acetic acid

[2-(3-Nitro-benzylcarbamoyl)-5-chloro-phenoxy]-acetic acid

[5-Chloro-2-(3-fluoro-5-trifluoromethyl-benzylcarbamoyl)-phenoxy]-acetic acid

[5-Chloro-2-(3,4-dichloro-benzylcarbamoyl)-phenoxy]-acetic acid

[2-(4-Bromo-2-fluoro-benzylcarbamoyl)-phenoxy]-acetic acid

[2-(4-Bromo-2-fluoro-benzylcarbamoyl)-4-chloro-phenoxy]-acetic acid

[4-Bromo-2-(4-bromo-2-fluoro-benzylcarbamoyl)-phenoxy]-acetic acid

[2-(4-Bromo-2-fluoro-benzylcarbamoyl)-4-fluoro-phenoxy]-acetic acid

[2-(4-Bromo-2-fluoro-benzylcarbamoyl)-4-methyl-phenoxy]-acetic acid

[4-nitro-2-(4-bromo-2-fluoro-benzylcarbamoyl)-phenoxy]-acetic acid

[2-(4-Bromo-2-fluoro-benzylcarbamoyl)-5-methylsulfanyl-phenoxy]-acetic acid

[2-(3-Nitro-benzylcarbamoyl)-4-methyl-phenoxy]-acetic acid

[2-(3-nitro-benzylcarbamdyl)-4-trifluoromethoxy-phenoxy]-acetic acid

[5-Fluoro-2-(3-nitro-benzylcarbamoyl)-phenoxy]-acetic acid

[2-(4-Bromo-2-fluoro-benzylcarbamoyl)-5-fluoro-phenoxy]-acetic acid

[5-Fluoro-2-(4-methyl-3-nitro-benzylcarbamoyl)-phenoxy]-acetic acid

[2-(4-Bromo-2-fluoro-benzylcarbamoyl)-4,5-difluoro-phenoxy]-acetic acid

[5-Fluoro-2-(3-nitro-benzylthiocarbamoyl)-phenoxy]-acetic acid

[2-(4-Bromo-2-fluoro-benzylthiocarbamoyl)-5-fluoro-phenoxy]-acetic acid

[4-Bromo-2-(4-bromo-2-fluoro-benzylthiocarbamoyl)-phenoxy]-acetic acid

[2-(4-Bromo-2-fluoro-benzylthiocarbamoyl)-4-trifluoromethoxy-phenoxy]-acetic acid

[2-(4-Bromo-2-fluoro-benzylthiocarbamoyl)-4,5-difluoro-phenoxy]-acetic acid

[2-(4-Bromo-2-fluoro-benzylcarbamoyl)-5-fluoro-4-methyl-phenoxy]-acetic acid

[2-(4-Bromo-2-fluoro-benzylthiocarbamoyl)-5-fluoro-4-methyl-phenoxy]-acetic acid

[2-(3-Nitro-benzylcarbamoyl)-5-fluoro-4-methyl-phenoxy]-acetic acid

[2-(3-Nitro-benzylthiocarbamoyl)-5-fluoro-4-methyl-phenoxy]-acetic acid

[2-(3-Nitro-benzylcarbamoyl)-4-bromo-5-fluoro-phenoxy]-acetic acid

[5-(3-Nitro-benzylcarbamoyl)-2-fluoro-biphenyl-4-yloxy]-acetic acid

[5-(3-Nitro-benzylthiocarbamoyl)-2-fluoro-biphenyl-4-yloxy]-acetic acid

[2-(3-Nitro-benzylcarbamoyl)-4-cyano-5-fluoro-phenoxy]-acetic acid

[2-(3-Nitro-benzylcarbamoyl)-5-fluoro-4-morpholin-4-yl-phenoxy]-acetic acid

{5-Fluoro-2[(4,5,7-trifluoro-benzothiazol-2-ylmethyl)carbamoyl]-phenoxy}-acetic acid {5-Fluoro-2-[(4,5,7-trifluoro-benzothiazol-2-ylmethyl)-thiocarbamoyl]-phenoxy}-acetic acid {5-Fluoro-2-[(5-trifluoromethyl-benzothiazol-2-ylmethyl)-carbamoyl]-phenoxy}-acetic acid {5-Chloro-2-[(5-trifluoromethyl-benzothiazol-2-ylmethyl)-carbamoyl]-phenoxy}-acetic acid The above compounds, further described in the Examples and other description of the invention below, are illustrative but are not meant to limit in any way the scope of the contemplated compounds according-to the present invention.

The compounds of the invention are administered to a patient or subject in need of treatment either alone or in combination with other compounds having similar or different biological activities. For example, the compounds of the invention may be administered in a combination therapy, i.e., either simultaneously in single or separate dosage forms or in separate dosage forms within hours or days of each other. Examples of such combination therapies include administering the compounds of Formula I with other agents used to treat hyperglycemia, hyperlipidemia, and diabetic complications.

Suitable compounds for use in combination therapy include

For Hyperglycemia:
 Insulin
 Metformin
 Troglitazone
 Pioglitazone
 Rosiglitazone
 Darglitazone
 Sulfonylureass such as glipizide and glimepiride
 Repaglinide
 alpha-glucosidase inhibitors such as acarbose, miglitol For Diabetic Complications:
 ACE inhibitors: Captopril, lisinopril, omaprilat
 Angiotensin II receptor antagonists (AT1-receptor) such as candesartan, losartan, irbesartan, and valsartan
 MMP inhibitors
 Protein kinase C inhibitors For Antihyperlipidemia:
 Statins such as Atorvastatin, simvastatin, pravastatin, fluvastatin, lovastatin, cerivastatin
 Fibrates such as Fenofibrate, bezafibrate, ciprofibrate, gemfibrozil.

Such combination therapy may involve, for example, simultaneous administration of the vasodilator, preferably an ACE inhibitor, and a compound of Formula I in separate pharmaceutical compositions, one pharmaceutical composition comprising both the vasodilator, preferably an ACE inhibitor, and the compound of Formula I, or administration of the two compounds at different times. Those skilled in the art will recognize other ways of achieving combination therapy with, for example, ACE inhibitors and the compounds of Formula I.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay, disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels on the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 1000 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The compounds of the present invention may be prepared by use of known chemical reactions and procedures. General methods for synthesizing the compounds are presented below. It is understood that the nature of the substituents required for the desired target compound often determines the preferred method of synthesis. All variable groups of these methods are as described in the generic description if they are not specifically defined below. More detailed procedures for particular examples are presented below in the experimental section.

METHODS OF PREPARATION

In general, compounds of the invention where X in Formula I is oxygen or sulfur can be conveniently prepared from a substituted salicyclic acid using general Scheme A set forth below.

dicyclohexylcarbodiinide (DCC). A review of such methods can be found in Bodanszky, M. *Principles of Peptide Synthesis*; Springer-Verlag: New York, 1984. It is understood, that the choice of the coupling method used will depend on such factors as functional group compatibility and desired scale. In general, when an unprotected salicylic acid is used, formation of an acid chloride using thionyl chloride is convenient. Subsequent addition of amine V, in the presence of an amine base like triethylamine or pyridine in an aprotic solvent like dichloromethane provides amide VI. Alternatively, aqueous or biphasic reaction conditions can be used with an inorganic base such as sodium hydroxide or potassium carbonate. This reaction, known as the Schotten-Baumann reaction, is illustrated in *Bioorg. Med. Chem. Letters* 1994, 4, 335. Introduction of the acetic acid moiety to provide phenoxyacetic acid derivative VII is typically accomplished using an alkylating reagent like ethyl bromoacetate or sodium 2-chloroacetic acid in an aqueous acetone solution with a base such as potassium carbonate. Other method using anhydrous reaction conditions are also useful and well known to those skilled in the art of organic synthesis. If the amide product VIII is desired, ester inter-

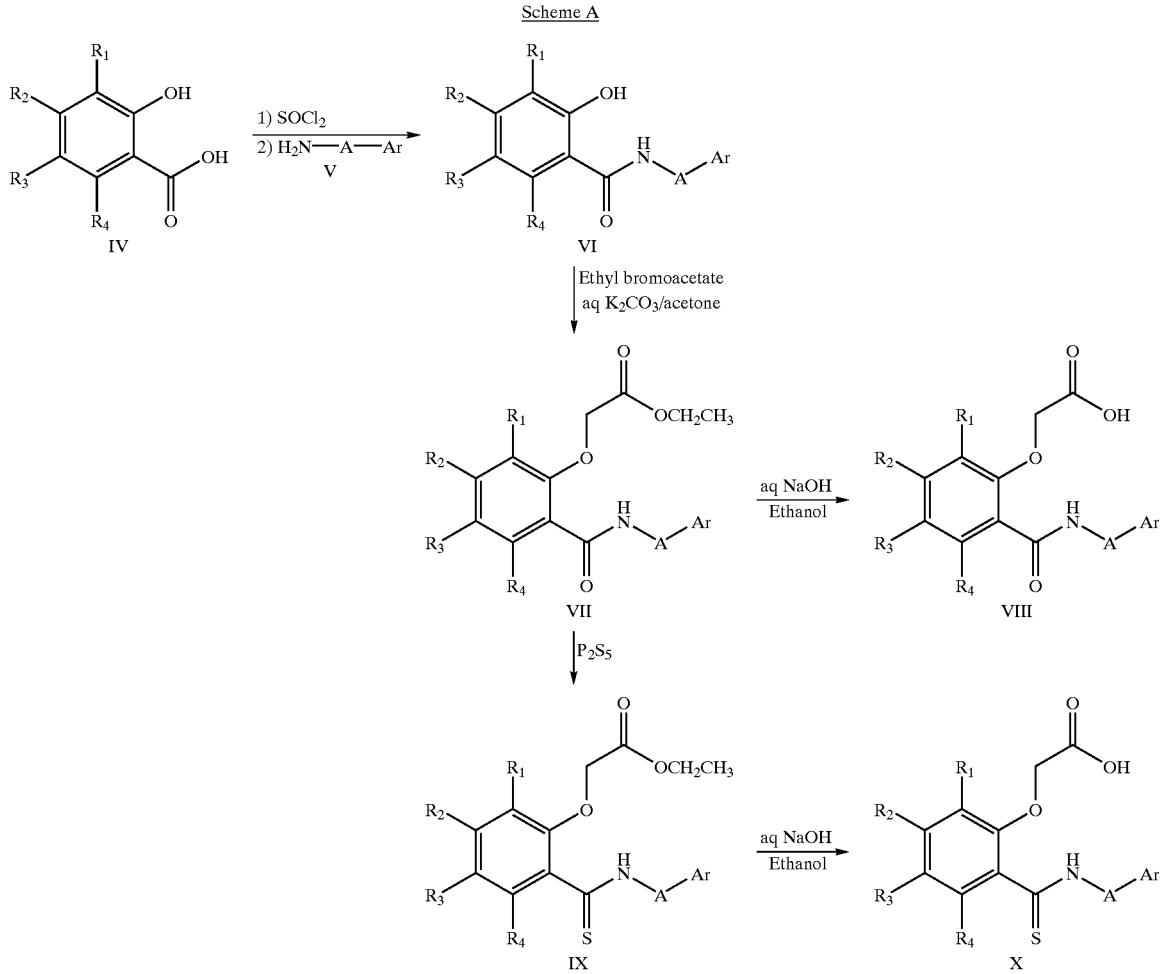

Scheme A

In this method a substituted salicyclic acid moiety IV is activated and coupled with an amine. Some examples of activating methods well-known to those skilled in the art include formation of acid chlorides or mixed anhydrides and the use of coupling reagents such as 1,3- mediate VII can be hydrolyzed to the acid using either aqueous acid or base conditions. Thioamide derivatives X can be prepared from the corresponding amides IX by treatment with reagents like phosphorous pentasulfide in an aprotic solvent like toluene. Thioamide products X can be obtained in a manner analogue to the amide product VIII. Ester intermediate IX can be hydrolyzed to the acid using either aqueous acid or base conditions.

If the desired substituted salicylic acid is not readily available, it can be prepared using known methods. One useful method is outlined in scheme B where a 2-flourobenzoic acid XI is treated with a base like sodium hydroxide in 1,3-dimethyl-2-imidazolidinone (DMI) at elevated temperatures (preferably about 135° C.).

Scheme B

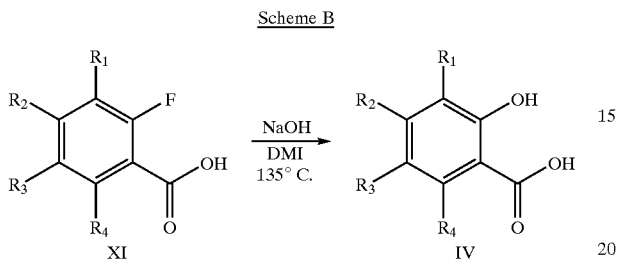

Scheme C

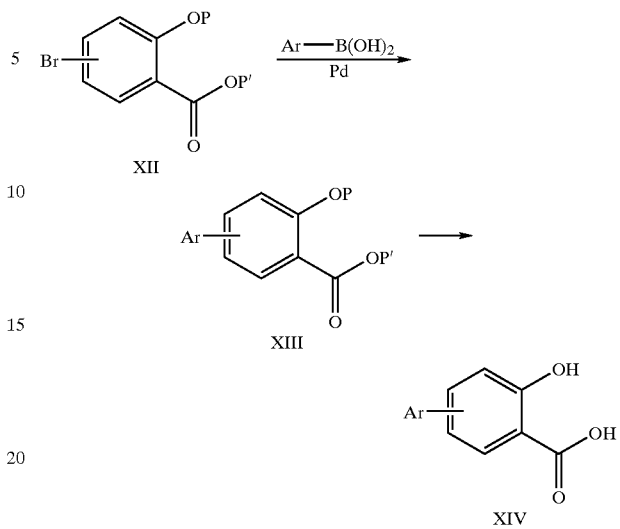

In general, the intermediate compounds IV wherein one of $R_{1-4}$ is aryl or heteroaryl can be synthesized using well established transition metal catalyzed coupling reactions like the Suzuki and Stille reactions. It is understood that, depending on the specific chemistry used, a protecting group, P, may be required. The use of these general methods is illustrated in *Protective Groups in Organic Synthesis*, Second Edition, T. W. Green and P. G. M. Wuts, John Wiley and Sons, New York, 1991.

In the Suzuki reaction, as outlined in scheme C, an optionally substituted aryl halide XII can be treated with an aryl- or heteroarylboronic acid and a palladium catalyst to provide the substituted salicylic acid derivatives XIII. These reactions are most often carried out in a mixture of ethereal or alcohol solvents with aqueous base in the presence of a palladium catalyst, such as $Pd(OAc)_2$, $Pd(OAc)_2$ w/$PPh_3$ or $Pd(PPh_3)_4$ as described in *Tetrahedron Lett*. 1998, 39, 4467, *J. Org. Chem*. 1999, 64, 1372 and *Heterocycles* 1992, 34, 1395. Deprotection, if required, can be carried out using known methods to provide intermediate XIV. A general review of Suzuki cross-couplings between boronic acids and aryl halides can be found in Miyaura, N; Suzuki, *A. Chem. Rev*. 1995, 95, 2457.

In addition, the Stille reaction also serves as a general method for the regiocontrolled synthesis of substitution salicylic acid intermediates XIV, as indicated in scheme D below. In this method, the salicylic acid moiety may serve as either the organotin species or the aryl halide. The stannyl-salicycilic acid derivative XV is conveniently prepared from the corresponding arylbromide Ar—Br (XII) by treatment with hexamethylditin (HMDT) and a palladium catalyst such as $Pd(PPh_3)_4$. Subsequently, this tin intermediate can be treated with a variety of partners (i.e., vinyl/allylic halides, vinyl triflates, aryl/heteroaryl halides and acyl halides, XVI) in the presence of a Palladium catalyst to provide the desired aryl- or heteroaryl coupled salicylic acid intermediates (XIII). Conversely, a halosalicylic acid derivative (XII) can be treated with a variety of tin reagents under Stille conditions to provide the desired substituted salicylic acids (XIII). For reviews of this chemistry see: (a) *Heterocycles* 1988, 27, 1585, (b) *Synth. Comm* 1992, 22, 1627, (c) *Synnlett* 1993, 771, (d) *Helv. Chim. Acta* 1993, 76, 2356 (e) *J. Org. Chem*. 1994, 59, 4250 and Farina, V.; Krishnamurthy, V; Scott, W., *Organic Reactions*, 1998, 50, 1–652.

Scheme D

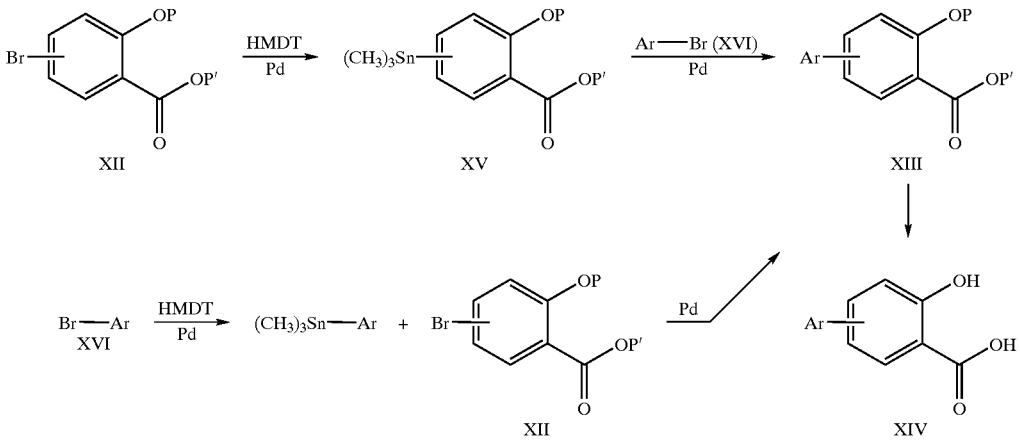

Transition metal catalyzed reactions can also be used to couple aryl- or heteroaryl halides with amines, alcohols and sulfur containing compounds to form the corresponding aryl- and heteroaryl aniline, ether and thioether derivatives. A general procedure for the synthesis of intermediate compounds where one of $R_{1-4}$ is —N(H)R, is outlined in scheme E below. Typically the aryl bromide or chloride XII is treated with a heteroatom containing intermediate XV, a base such as potassium tert-butoxide or cesium carbonate, a palladium catalyst like $Pd_2(dba)_3$ or $(DPPF)PdCl_2$ and a ligand such as BINAP or DPPF in toluene or tetrahydrofuran at elevated temperatures, typically 50–150° C. to produce the desired intermediate XVI.

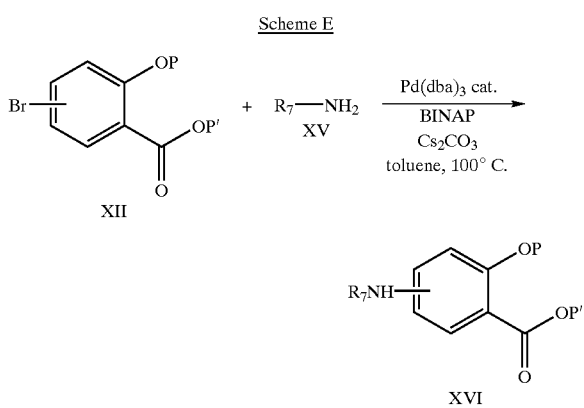

Scheme E

A more detailed description of this chemistry can be found in: (a) *J. Chem. Soc.*, Perkin Trans. 1, 1998, 2615, (b) *Acc. Chem. Res.* 1998, 31, 805, (c) *Tetrahedron Letters*, 1997, 38, 6359.

In addition to the synthesis of substituted salicylic acid intermediates, transition metal catalyzed coupling reactions can also be used to prepare target compounds from advanced intermediates. For example, as illustrated in scheme F, treatment of the intermediate bromide XVII with an aryl or heteroaryl boronic acid or tin intermediates, R-M, using Pd-mediated coupling conditions provides the desired aryl and heteroaryl product XVIII. In general the utility of this method is determined by the ease of synthesis of advanced intermediates of type XVII and the availability of aryl and heteroaryl boronic acids and tin derivatives.

Scheme F

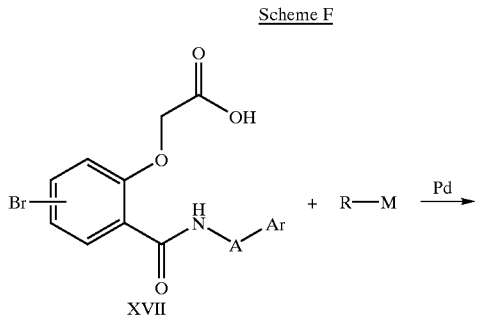

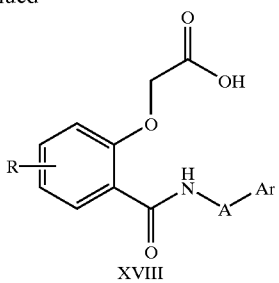

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference.

The preparation of the compounds of the present invention is illustrated further by the following examples, which are not to be construed as limiting the invention in scope or spirit to the specific procedures and compounds described in them.

EXAMPLE 1

[2-(4-Bromo-2-fluoro-benzylcarbamoyl)-5-chloro-phenoxy]-acetic Acid

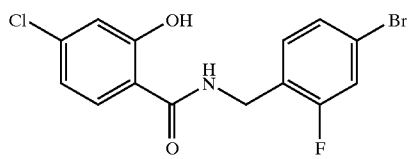

Step 1: N-(4-Bromo-2-fluoro-benzyl)-4-chloro-2-hydroxy-benzamide:

A solution of 5-chloro-2-hydroxy-benzoic acid (20.0 g, 116 mmol) in heptane (232 mL, 0.5 M) was treated with thionyl chloride (25.4 mL, 348 mmol) and heated to 60° C. for 6 h. After cooling to room temperature, the solution was concentrated under reduced pressure to give 5-chloro-2-hydroxy-benzoyl chloride as a thick yellow oil (22 g) which was used without further purification.

A solution of 5-chloro-2-hydroxy-benzoyl chloride (4.00 g, 23.2 mmol) in dichloromethane (46 mL, 0.5 M) was treated with triethylamine (6.46 mL, 46.4 mmol) and 4-bromo-2-fluorobenzylamine (6.10 g, 30.1 mmol). After stirring at room temperature for 16 h, the solution was washed successively with 2 N HCl and saturated aq NaCl. The organic layer was dried over $Na_2SO_4$, filtered and concentrated. Purification by MPLC (10–50% ethyl acetate in heptane, 23 mL/min, 70 min) gave N-(4-bromo-2-fluoro-benzyl)-4-chloro-2-hydroxy-benzamide as a white crystalline solid (4.4 g, 53%): mp 159–161° C.; $R_f$ 0.49 (30% ethyl acetate in heptane); $^1H$ NMR (DMSO-$d_6$, 300 MHz) δ 12.56 (br s, 1H), 9.28 (br t, J=5.4 Hz, 1H), 7.88 (d, J=6.0 Hz, 1H), 7.50 (dd, $J_1$=9.9 Hz, $J_2$=1.8 Hz, 1H), 7.37 (dd, $J_1$=8.4 Hz, $J_2$=1.8 Hz, 1H), 7.33 (dd, $J_1$=15.9 Hz, $J_2$=8.1 Hz, 1H), 6.99–6.93 (m, 2H), 4.50–4.46 (m, 2H). ESI-LC/MS m/z calcd for $C_{14}H_{10}BrClFNO_2$: 358.6; found 360.0 (M+1)$^+$. Anal. calcd for $C_{14}H_{10}BrClFNO_2$: C, 46.89; H, 2.81; N, 3.91; Cl, 19.78. Found C, 46.89; H, 2.81; N, 3.90; Cl, 19.73.

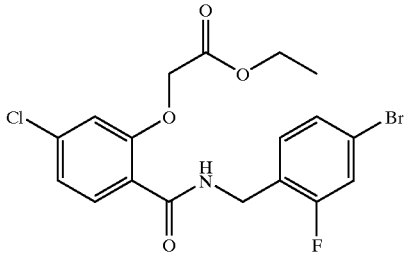

Step 2: [2-(4-Bromo-2-fluoro-benzylcarbamnoyl)-5-chloro-phenoxy]-acetic Acid Ethyl Ester A solution of N-(4-bromo-2-fluoro-benzyl)-4-chloro-2-hydroxy-benzamide (3.25 g, 9.06 mmol) in acetone (45 mL, 0.2 M) was treated with aq $K_2CO_3$ (2 M, 6.8 mL, 14 mmol) and ethyl bromoacetate (1.2 mL, 11 mmol). After being heated to 50° C. for 8 h, the solution was cooled to room temperature and concentrated under reduced pressure until most of the acetone was removed. The solution was acidified to pH 1–2 with 2 N HCl, diluted with ethyl acetate and washed with saturated aq NaCl. The organic layer was dried over $Na_2SO_4$, filtered and concentrated. Purification by MPLC (10–60% ethyl acetate in heptane, 23 mL/min, 70 min) gave [2-(4-bromo-2-fluoro-benzylcarbamoyl)-5-chloro-phenoxy]-acetic acid ethyl ester as a white crystalline solid (3.78 g, 94%): mp 126–127° C.; $R_f$ 0.61 (50% ethyl acetate in heptane); $^1$H NMR (DMSO-$d_6$, 300 MHz) δ 8.90 (t, J=6 Hz, 1H), 7.82 (d, J=8.4 Hz, 1H), 7.52–7.47 (m, 1H), 7.39–7.31 (m, 2H),. 7.28 (d, J=1.8 Hz, 1H), 7.14 (dd, J=8.4 Hz, $J_2$=1.8 Hz, 1H), 5.00, (s, 2H), 4.49 (d, J=6 Hz, 2H), 4.16 (q, J=7.2 Hz, 2H), 1.18 (t, J=6.6 Hz, 3H). ESI-LC/MS ml/z calcd for $C_{18}H_{16}BrClFNO_4$: 444.7; found 446.0 (M+1)$^+$. Anal. calcd for $C_{18}H_{16}BrClFNO_4$: C, 48.62; H, 3.63; N, 3.15; Cl, 15.95. Found C, 48.57; H, 3.63; N, 3.11; Cl, 16.00.

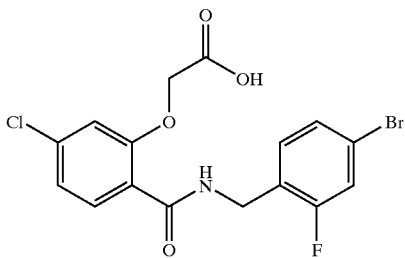

Step 3: [2-(4-Bromo-2-fluoro-benzylcarbamoyl)-5-chloro-phenoxy]-acetic Acid

A solution of [2-(4-bromo-2-fluoro-benzylcarbamoyl)-5-chloro-phenoxy]-acetic acid ethyl ester (3.20 g, 7.20 mmol) in ethanol (36 mL, 0.2 M) was cooled to 0° C. and treated with aq NaOH (1.25 M, 28.8 mL, 36.0 mmol). After stirring for 30 min, the solution was warmed to room temperature and stirred an additional 4 h. Next, the solution was acidified to pH 1–2 with 2 N HCl, diluted with ethyl acetate and washed with saturated aq NaCl. The organic layer was dried over $Na_2SO_4$, filtered and concentrated to give [2-(4-bromo-2-fluoro-benzylcarbamoyl)-5-chloro-phenoxy]-acetic acid as a white crystalline solid (2.91 g, 97%): mp 184–185° C.; $R_f$ 0.31 (20% methanol in dichloromethane); $^1$H NMR (DMSO-$d_6$, 300 MHz) δ 13.40 (br s, 1H), 9.05, (t, J=5.7 Hz, 1H), 7.83, (d, J=8.4 Hz, 1H), 7.48 (d, J=10.5 Hz, 1 Hz), 7.38–7.32 (m, 2H), 7.26 (d, J=1.8 Hz, 1H), 7.13 (dd, $J_1$=8.4 Hz, $J_2$=1.5 Hz, 1H), 4.91 (s, 2H), 4.49 (d, J=5.7 Hz, 2H). ESI-LC/MS m/z calcd for $C_{16}H_{12}BrClFNO_4$: 416.6; found 418.0 (M+1)$^+$. Anal. calcd for $C_{16}H_{12}BrClFNO_4$: C, 46.13; H, 2.90; N, 3.36; Cl, 17.02. Found C, 46.04; H, 2.89; N, 3.31; Cl, 17.09.

EXAMPLE 2

(2-Benzylcarbamoyl-5-chloro-phenoxy)-acetic Acid

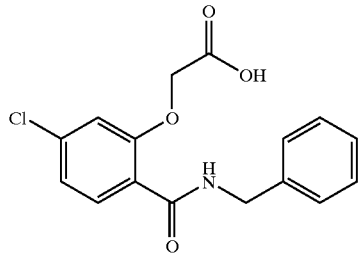

(2-Benzylcarbamoyl-5-chloro-phenoxy)-acetic was prepared in a manner analogous to that set forth in Example 1, except benzylamine was used in place of 4-bromo-2-fluorobenzylamine hydrochloride in step 1: mp 145–146° C.; $R_f$ 0.48 (20% methanol in dichloromethane); $^1$H NMR (DMSO-$d_6$ 300 MHz) δ 13.37 (s, 1H), 9.09 (t, J=6.0 Hz, 1H), 7.86 (d, J=8.4 Hz, 1H), 7.34–7.18 (m, 6H), 7.14 (dd, $J_1$=8.4 Hz, $J_2$=1.8 Hz, 1H), 4.92 (s, 2H), 4.50 (d, J=6.0 Hz, 2H). ESI-LC/MS m/z calcd for $C_{16}H_{14}ClNO_4$: 319.74; Found 318.0 (M−1)$^-$. Anal. calcd for $C_{16}H_{14}ClNO_4$: C, 60.10; H, 4.41; N, 4.38; Cl, 11.09. Found C, 60.03; H, 4,49; N, 4.36; Cl, 11.05.

EXAMPLE 3

[5-Chloro-2-(3-fluoro-benzylcarbamoyl)-phenoxy]-acetic Acid

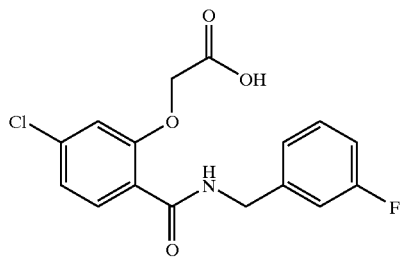

[5-Chloro-2-(3-fluoro-benzylcarbamoyl)-phenoxy]-acetic acid was prepared in a manner analogous to that set forth in Example 1, except 3-fluorobenzylamine was used in place of 4-bromo-2-fluorobenzylamine hydrochloride in step 1: mp 155° C.; $R_f$ 0.43 (20% methanol in dichloromethane); $^1$H NMR (DMSO-$d_6$ 300 MHz) δ 10.81 (br s, 1H), 7.73 (d, J=9.0 Hz, 1H), 7.34–7.27 (m, 1H), 7.19–7.11 (m, 2H), 7.05 (dd, $J_1$=8.3 Hz, $J_2$=1.7 Hz, 1H), 6.99 (dt, $J_1$=8.3 Hz, $J_2$=2.0 Hz, 1H), 4.51–4.47 (m, 4H). ESI-LC/MS m/z calcd for $C_{16}H_{13}ClFNO_4$: 337.7; Found 336, 338.0 (M−1, M+1)$^±$. Anal. calcd $C_{16}H_{15}ClFNO_5$: C, 54.02; H, 4.25; N, 3.94; Cl, 9.97. Found C, 53.94; H, 3.75; N, 3.91; Cl, 9.99.

EXAMPLE 4

[5-Chloro-2-(3-trifluoromethyl-benzylcarbamoyl)-phenoxy]-acetic Acid

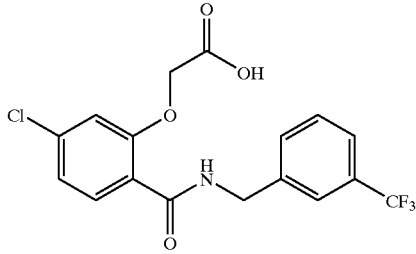

[5-Chloro-2-(3-trifluoromethyl-benzylcarbamoyl)-phenoxy]-acetic acid was prepared in a manner analogous to that set forth in Example 1, except 3-(trifluoromethyl)-benzyl amine was used in place of 4-bromo-2-fluorobenzylamine hydrochloride in step 1: mp 179–181° C.; $R_f$ 0.76 (20% methanol in dichloromethane); $^1$H NMR (DMSO-$d_6$ 300 MHz) δ 13.36 (br s, 1H), 9.17 (t, J=6.2 Hz, 1H), 7.84 (d, J=8.1 Hz, 1H), 7.67–7.52 (m, 4H), 7.27 (d, J=1.8 Hz, 1H), 7.15 (dd, $J_1$=8.3 Hz, $J_2$=2.0 Hz, 1H), 4.93 (s, 2H), 4.59 (d, J=6 Hz, 2H). ESI-LC/MS m/z calcd for $C_{17}H_{15}ClF_3NO_4$: 387.7; Found 388.0 (M+1)$^+$. Anal. calcd for $C_{17}H_{15}ClF_3NO_4$: C, 52.66; H, 3.38; N, 3.61; Cl, 9.14. Found C, 52.57; H, 3.39; N, 3.55; Cl, 9.21.

EXAMPLE 5

[2-(3-Nitro-benzylcarbamoyl)-5-chloro-phenoxy]-acetic Acid

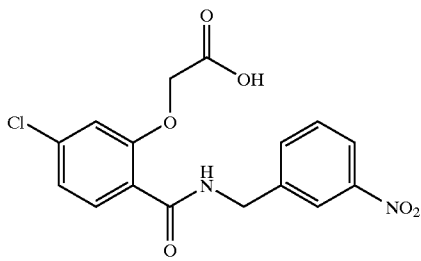

[2-(3-Nitro-benzylcarbamoyl)-5-chloro-phenoxy]-acetic acid was prepared in a manner analogous to that set forth in Example 1, except 3-nitrobenzylamine hydrochloride was used in place of 4-bromo-2-fluorobenzylamine hydrochloride in step 1: mp 200° C.; $R_f$ 0.25 (20% methanol in dichloromethane); $^1$H NMR (DMSO-$d_6$ 300 MHz) δ 13.35 (br s, 1H), 9.21 (br t, J=5.4 Hz, 1H), 8.18 (br s, 1H), 8.05–8.07 (m, 1H), 7.82 (d, J=8.4 Hz, 1H), 7.81 (t, J=9.3 Hz, 1H), 7.60 (t, J=7.8 Hz, 1H), 7.25 (d, J=2.1 Hz, 1H), 7.13 (dd, $J_1$=8.4 Hz, $J_2$=1.8 Hz, 1H), 4.91 (s, 2H), 4.61 (d, J=6.3 Hz, 2H). ESI-LC/MS m/z calcd for $C_{16}H_{13}ClN_2O_6$: 364.1; Found 365.0 (M+1)$^+$. Anal. calcd for $C_{16}H_{13}ClN_2O_6$: C, 52.96; H, 3.59; N, 7.68; Cl, 9.72. Found C, 52.63; H, 3.64; N, 7.60; Cl, 9.81.

EXAMPLE 6

[5-Chloro-2-(4-chloro-benzylcarbamoyl)-phenoxy]-acetic Acid

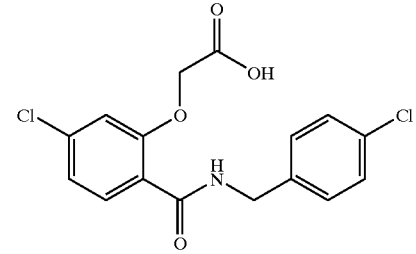

[5-Chloro-2-(4-chloro-benzylcarbamoyl)-phenoxy]-acetic acid was prepared in a manner analogous to that set forth in Example 1, except 4-chlorobenzylamine was used in place of 4-bromo-2-fluorobenzylamine hydrochloride in step 1: mp 184–186° C.; $R_f$ 0.49 ((20% methanol in dichloromethane); $^1$H NMR (DMSO-$d_6$ 300 MHz)δ 13.34 (br s, 1H), 9.10 (t, J=6.2 Hz, 1H), 7.84 (d, J=8.4 Hz, 1H), 7.35 (s, 4H), 7.25 (d, J=1.8 Hz, 1H), 7.13 (dd, $J_1$=8.3 Hz, $J_2$=2.0 Hz, 1H), 4.91 (s, 2H), 4.48 (d, J=6 Hz, 2H). ESI-LC/MS m/z calcd for $C_{16}H_{13}Cl_2NO_4$: 354.2; Found 354.0, 355.0 (M, M+1)$^+$. Anal. calcd for $C_{16}H_{13}Cl_2NO_4$: C, 54.26; H, 3.70; N, 3.95; Cl, 20.02. Found C, 54.30; H, 3.74; N, 3.90; Cl, 20.10.

EXAMPLE 7

[2-(4-Bromo-benzylcarbamoyl)-5-chloro-phenoxy]-acetic Acid

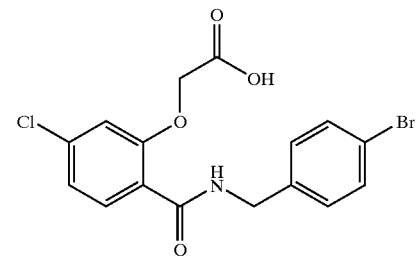

[2-(4-Bromo-benzylcarbamoyl)-5-chloro-phenoxy]-acetic acid was prepared in a manner analogous to that set forth in Example 1, except 4-bromobenzylamine hydrochloride was used in place of 4-bromo-2-fluorobenzylamine hydrochloride in step 1: mp 172–173° C.; $R_f$ 0.63 (20% methanol in dichloromethane); $^1$H NMR (DMSO-$d_6$ 300 MHz) δ 9.10 (t, J=5.6 Hz, 1H), 7.84 (d, J=8.4 Hz, 1H), 7.50–7.46 (m, 2H), 7.30–7.24 (m, 3H), 7.13 (dd, $J_1$=8.4 Hz, $J_2$=2.0 Hz, 1H), 4.91 (s, 2H), 4.46 (d, J=5.7 Hz, 2H). ESI-LC/MS m/z calcd for $C_{16}H_{13}BrClNO_4$: 398.6; Found 399.0 (M+1)$^+$, 400 (M+2)$^+$. Anal. calcd for $C_{16}H_{13}BrClNO_4$: C, 48.21; H, 3.29; N, 3.51; Cl, 17.79; Br, 40.09. Found C, 48.53; H, 3.70; N, 3.21; Cl, 17.89; Br, 40.32.

EXAMPLE 8

[5-Chloro-2-(4-methoxy-benzylcarbamoyl)-phenoxy]-acetic Acid

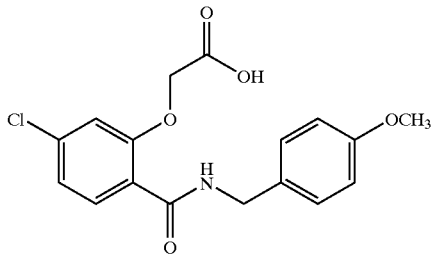

[5-Chloro-2-(4-methoxy-benzylcarbamoyl)-phenoxy]-acetic acid was prepared in a manner analogous to that set forth in Example 1, except 4-methoxybenzylamine hydrochloride was used in place of 4-bromo-2-fluorobenzylamine hydrochloride in step 1: MP 178–179° C.; $R_f$ 0.80 (20% methanol in dichloromethane); $^1$H NMR (acetone-$d_6$ 300 MHz) δ 9.02 (br s, 1H), 8.09 (d, J=8.4 Hz, 1H), 7.32 (d, J=8.7 Hz, 2H), 7.25 (d, J=2.1 Hz, 1H), 7.15 (dd, $J_1$=8.6 Hz, $J_2$=1.8 Hz, 1H), 6.85 (dd, $J_1$=6.6 Hz, $J_2$=2.1 Hz, 2H), 5.0 (s, 2H), 4.54 (d, J=6 Hz, 2H), 3.76 (s, 3H). ESI-LC/MS m/z calcd for $C_{20}H_{22}ClNO_5$: 349.8; Found 350.0 (M+1)$^+$. Anal. calcd for $C_{20}H_{22}ClNO_5$: C, 58.38; H, 4.61; N, 4.00. Found C, 58.35; H, 4.75; N, 3.87.

EXAMPLE 9

[5-Chloro-2-(4-trifluoromethoxy-benzylcarbamoyl)-phenoxy]-acetic Acid

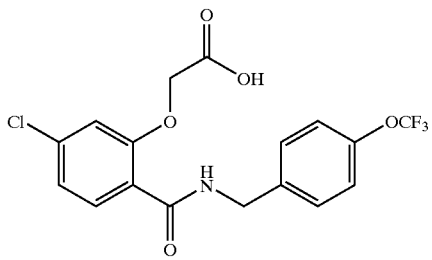

[5-Chloro-2-(4-trifluoromethoxy-benzylcarbamoyl)-phenoxy]-acetic acid was prepared in a manner analogous to that set forth in Example 1, except (4-trifluoromethoxy)-benzyl amine was used in place of 4-bromo-2-fluorobenzylamine hydrochloride in step 1: mp 184–185° C.; $R_f$ 0.41 (20% methanol in dichloromethane); $^1$H NMR (DMSO-$d_6$ 300 MHz) δ 9.18 (t, J=6 Hz, 1H), 7.85 (J=8.4 Hz, 1H), 7.47–7.42 (m, 2H), 7.32–7.26 (m, 3H), 7.14 (dd, $J_1$=8.4 Hz, $J_2$=1.8 Hz, 1H), 4.92 (s, 2H), 4.53 (d, J=6 Hz, 2H). ESI-LC/MS m/z calcd for $C_{17}H_{13}ClF_3NO_5$: 403.7; Found 404.0 (M+1)$^+$.

EXAMPLE 10

[5-Chloro-2-(2,6-difluoro-benzylcarbamoyl)-phenoxy]-acetic Acid

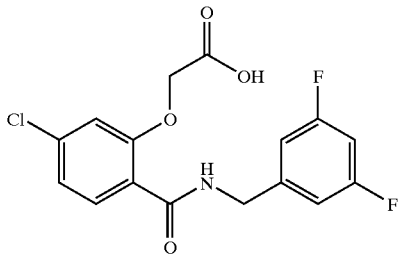

[5-Chloro-2-(2,6-difluoro-benzylcarbamoyl)-phenoxy]-acetic acid was prepared in a manner analogous to that set forth in Example 1, except 2,6-difluorobenzylamine hydrochloride was used in place of 4-bromo-2-fluorobenzylamine hydrochloride in step 1: mp 188–190° C.; $R_f$ 0.76 (20% methanol in dichloromethane); $^1$H NMR (acetone-$d_6$ 300 MHz) δ 8.86 (br s, 1H), 8.07 (d, J=8.4 Hz, 1H), 7.37 (dt, $J_1$=7.2 Hz, $J_2$=1.8 Hz, 1H), 7.24 (d, J=1.5 Hz, 1H), 7.15 (dd, $J_1$=8.6 Hz, $J_2$=1.5 Hz, 1H), 6.99 (t, J=7.8 Hz, 1H), 4.97 (s, 2H), 4.69 (d, J=5.1 Hz, 2H). ESI-LC/MS m/z calcd for $C_{16}H_{12}ClF_2 NO_4$: 355.72; Found 356 (M+1)$^+$. Anal. calcd for $C_{16}H_{12}ClF_2 NO_4$: C, 54.02; H, 3.40; N, 3.94; Cl, 9.97. Found C, 53.43; H, 3.46; N, 3.83; Cl, 9.82.

EXAMPLE 11

[5-Chloro-2-(3-fluoro-5-trifluoromethyl-benzylcarbamoyl)-phenoxy]-acetic Acid

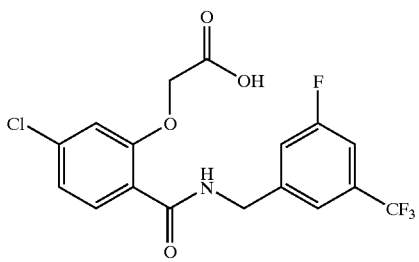

[5-Chloro-2-(3-fluoro-5-trifluoromethyl-benzylcarbamoyl)-phenoxy]-acetic acid was prepared in a manner analogous to that set forth in Example 1, except 3-fluoro-5-(trifluoromethyl)-benzylamine was used in place of 4-bromo-2-fluorobenzylamine hydrochloride in step 1: mp 160–162° C.; $R_f$ 0.42 (20% methanol in dichloromethane); $^1$H NMR (DMSO-$d_6$ 300 MHz) δ 13.34 (br s, 1H), 9.16 (t, J=6 Hz, 1H), 7.83 (d, J=8.7 Hz, 1H), 7.55–7.47 (m, 3H), 7.27 (d, J=2.1 Hz, 1H), 7.14 (dd, $J_1$=8.4 Hz, $J_2$=1.8 Hz, 1H), 4.93 (s, 2H), 4.59 (d, J=6.3 Hz, 2H). ESI-LC/MS m/z calcd for $C_{17}H_{12}ClF_4NO_4$: 405.73; Found 406.0 (M+1)$^+$. Anal. calcd $C_{17}H_{12}ClF_4NO_4$: C, 50.32; H, 2.98; N, 3.45; Cl, 8.74. Found C, 50.28; H, 3.01; N, 3.40; Cl, 8.79.

EXAMPLE 12

[2-(3,5-Bistrifluoromethyl-benzylcarbamoyl)-5-chloro-phenoxy]-acetic Acid

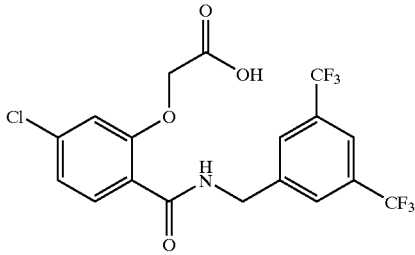

[2-(3,5-Bistrifluoromethyl-benzylcarbamoyl)-5-chlorophenoxy]-acetic acid was prepared in a manner analogous to that set forth in Example 1, except 3,5-(bistrifluoromethyl)-benzylamine was used in place of 4-bromo-2-fluorobenzylamine hydrochloride in step 1: mp 191–193° C.; $R_f$ 0.23 (20% methanol in dichloromethane); $^1$H NMR (DMSO-$d_6$ 300 MHz) δ 13.34 (br s, 1H), 9.20 (t, J=6 Hz, 1H), 8.01–7.97 (m, 3H), 7.80 (d, J=3 Hz, 1H), 7.26 (d, J=1.8 Hz, 1H), 7.14 (dd, $J_1$=8.7 Hz, $J_2$=2.1 Hz, 1H), 4.92 (s, 2H), 4.67 (d, J=6 Hz, 2H). ESI-LC/MS m/z calcd for $C_{18}H_{12}ClF_6NO_4$: 455.7; Found 456.0 (M+1)$^+$. Anal. calcd for $C_{18}H_{12}ClF_6NO_4$: C, 47.44; H, 2.65; N, 3.07; Cl, 7.78. Found C, 47.53; H, 2.72; N, 3.06; Cl, 7.86.

EXAMPLE 13

[5-Chloro-2-(3,5-dimethoxy-benzylcarbamoyl)-phenoxy]-acetic Acid

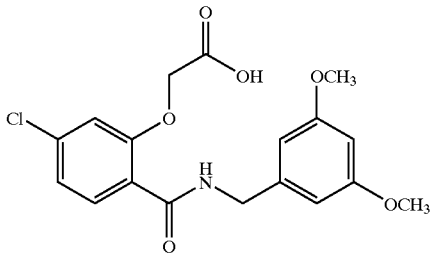

[5-Chloro-2-(3,5-dimethoxy-benzylcarbamoyl)-phenoxy]-acetic acid was prepared in a manner analogous to that set forth in Example 1, except 3,5-dimethoxybenzylamine was used in place of 4-bromo-2-fluorobenzylamine hydrochloride in step 1: mp 163° C.; $R_f$ 0.57 (20% methanol in dichloromethane); $^1$H NMR (DMSO-$d_6$ 300 MHz) δ 3.39 (br s, 1H), 9.04 (t, J=6.2 Hz, 1H), 7.86 (d, J=8.2 Hz, 1H), 7.25 (d, J=1.9 Hz, 1H), 7.14 (dd, $J_1$=8.2 Hz, $J_2$=1.9 Hz, 1H), 6.49 (d, J=2.2 Hz, 2H), 6.34 (t, J=2.4 Hz, 1H), 4.93 (s, 2H), 4.43 (d, J=6 Hz, 2H), 3.69 (s, 6H). ESI-LC/MS m/z calcd for $C_{18}H_{18}ClNO_6$: 379.8; Found 380.0 (M+1)$^+$. Anal. calcd for $C_{18}H_{18}ClNO_6$: C, 56.92; H, 4.78; N, 3.69; Cl, 9.33. Found C, 56.93; H, 4.84; N, 3.76; Cl, 9.25.

EXAMPLE 14

[5-Chloro-2-(3,4-dichloro-benzylcarbamoyl)-phenoxy]-acetic Acid

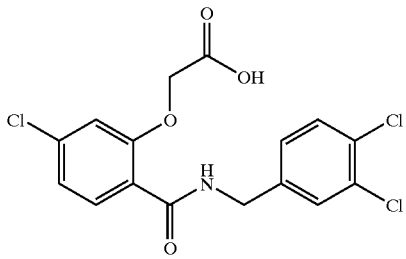

[5-Chloro-2-(3,4-dichloro-benzylcarbamoyl)-phenoxy]-acetic acid was prepared in a manner analogous to that set forth in Example 1, except 3,4-dichlorobenzylamine was used in place of 4-bromo-2-fluorobenzylamine hydrochloride in step 1: mp 177–178° C.; $R_f$ 0.39 (20% methanol in dichloromethane); $^1$H NMR (DMSO-$d_6$ 300 MHz) δ 9.19 (t, J=6.0 Hz, 1H), 7.81 (d, J=8.1 Hz, 1H), 7.55 (d, $J_1$=8.1 Hz, 1H), 7.55, (d, J=1.8 Hz, 1H), 7.31 (dd, $J_1$=8.1 Hz, $J_2$=2.1 Hz, 1H), 7.25 (d, J=1.8 Hz, 1H), 7.12 (dd, $J_1$=8.4 Hz, $J_2$=1.8 Hz, 1H), 4.90 (s, 2H), 4.48 (d, J=6.0 Hz, 2H). ESI-LC/MS m/z calcd for $C_{16}H_{12}Cl_3NO_4$: 387.0; Found 388.0 (M+1)$^+$. Anal. calcd for. $C_{16}H_{12}Cl_3NO_4$: C, 49.45; H,. 3.11; N, 3.60; Cl, 27.37. Found C, 49.36; H, 3.16; N, 3.53; Cl, 27.25.

EXAMPLE 15

{2-[(Benzo[1,3]dioxol-5-ylmethyl)-carbamoyl]-5-chloro-phenoxy}-acetic Acid

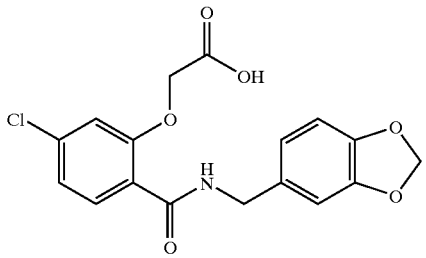

{2-[(Benzo[1,3]dioxol-5-ylmethyl)-carbamoyl]-5-chlorophenoxy}-acetic acid was prepared in a manner analogous to that set forth in Example 1, except piperonylamine was used in place of 4-bromo-2-fluorobenzylamine hydrochloride in step 1: mp 208–209° C.; $R_f$ 0.25 (10% methanol in dichloromethane); $^1$H NMR (DMSO-$_6$ 300 MHz) δ 13.38 (br s, 1H), 9.02 (t, J=6.0 Hz, 1H), 7.84 (d, J=8.4 Hz, 1H), 7.24 (d, J=1.2 Hz, 1H), 7.13 (dd, $H_1$=8.1 Hz, $J_2$=0.9 Hz, 1H), 6.87 (s, 1H), 6.83–6.73 (m, 2H), 5.94 (s, 2H), 4.9 (s, 2H), 4.39 (d, J=6.0 Hz, 2H). ESI-LC/MS m/z calcd for $C_{17}H_{14}ClNO_6$: 363.1; Found 362.0 (M−1)$^−$. Anal. calcd for $C_{17}H_{14}ClNO_6$: C, 56.13; H, 3.88; N, 3.85; Cl, 9.75. Found C, 56.24; H, 3.88; N, 3.82; Cl, 9.84.

EXAMPLE 16

[2-(4-Bromo-2-fluoro-benzylcarbamoyl)-5-methoxy-phenoxy]-acetic Acid

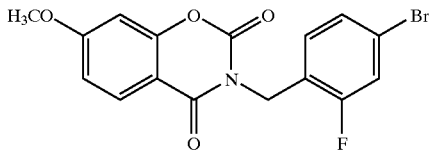

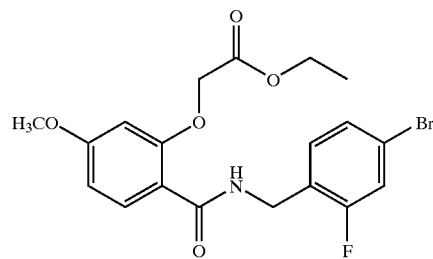

Step 1: 3-(4-Bromo-2-fluoro-benzyl)-7-methoxy Benzo[e][1,3]oxazine-2,4-dione:

A solution of 2-hydroxy-4-methoxybenzoic acid (2.04 g, 12.2 mmol) in tetrahydrofuran (20 mL, 0.6 M) was cooled to 0° C. After being treated with diisopropylethylamine (4.4 mL, 25.3 mmol) and ethyl chloroformate (2.4 mL, 25.1 mmol), the mixture was stirred at room temperature for 1 h and subsequently treater with a solution of 2-fluoro-4-bromobenzylamine (2.92 g, 12.1 mmol) and diisopropylethylamine (4.4 mL, 25.3 mmol) in tetrahydrofuran (15 mL). After stirring at room temperature for 22 h, the reaction mixture was diluted ethyl acetate and successively washed with 2 N HCl, saturated aq NaHCO$_3$ and saturated aq NaCl. The organic layer was dried over Na$_2$SO$_4$, filtered and concentrated. The crude solid was purified by recrystallization with heptane and ethyl acetate to give 3-(4-bromo-2-fluoro-benzyl)-7-methoxy benzo[e][1,3]oxazine-2,4-dione (1.68 g, 36%): $^1$H NMR (DMSO-d$_6$, 300 MHz) δ 7.87 (d, J=8.4 Hz, 1H), 7.53 (dd, J$_1$=10.5 Hz, J$_2$=1.1 Hz, 1H), 7.33–7.34 (m, 2H), 7.03–6.99 (m, 2H), 5.02 (s, 2H), 3.87 (s, 3H).

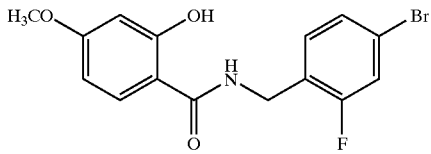

Step 2: N-(4-Bromo-2-fluoro-benzyl)-2-hydroxy-4-methoxy-benzamide:

A. solution of 3-(4-bromo-2-fluoro-benzyl)-7-methoxy benzo[e][1,3]oxazine-2,4-dione (1.67 g, 4.4 mmol) in ethanol (80 ml, 0.06 M) was cooled to 0° C. and treated with aq KOH (0.673 g, 11.9 mmol, 1.2 M). After 3 h, the reaction was acidified to pH 1–2 with 2 N HCl and extracted with ethyl acetate (3x). The combined organic extracts were washed with saturated aq NaCl, dried over Na$_2$SO$_4$, filtered and concentrated. The crude solid was recrystallized from heptane and ethyl acetate to give N-(4-bromo-2-fluoro-benzyl)-2-hydroxy-4-methoxy-benzamide as a white crystalline solid (1.10 g, 71%): mp 128–129.5° C.; R$_f$ 0.28 (25% ethyl acetate in heptane); $^1$H NMR (DMSO-d$_6$ 300 MHz) δ 12.70 (br s, 1H), 9.14 (br t, J=5.2 Hz, 1H), 7.80 (d; J=8.5 Hz, 1H), 7.50 (d, J=8.5 Hz, 1H), 7.40–7.25 (m, 2H), 6.50–6.48 (m, 2H), 4.45 (d, J=5.2 Hz, 2H), 3.75 (s, 3H). ESI-LC/MS m/z calcd for C$_{15}$H$_{13}$BrFNO$_2$: 353.0; found 352.0 (M–1)$^-$. Anal. calcd for C$_{15}$H$_{13}$BrFNO$_2$: C, 50.87; H, 3.70; N, 3.95. Found C, 50.70; H, 3.73; N, 3.91.

Step 3: [2-(4-Bromo-2-fluoro-benzylcarbamoyl)-5-methoxy-phenoxy-acetic Acid Ethyl Ester A solution of N-(4-bromo-2-fluoro-benzyl)-2-hydroxy-4-methoxy-benzamide (2.33 g, 6.9 mmol) in acetone (35 mL, 0.2 M) was treated with aq K$_2$CO$_3$ (2 M, 5.0 mL, 10.0 mmol) and ethyl bromoacetate (0.9 mL, 8.1 mmol). After being heated to 50° C. for 2.5 h, the solution was cooled to room temperature and concentrated under reduced pressure until most of the acetone was removed. The solution was acidified to pH 1–2 with 2 N HCl, diluted with ethyl acetate and washed with saturated aq NaCl. The organic layer was dried over Na$_2$SO$_4$, filtered and concentrated. Purification by MPLC (10–60% ethyl acetate in heptane, 23 mL/min, 70 min) gave [2-(4-bromo-2-fluoro-benzylcarbamoyl)-5-chloro-phenoxy]-acetic acid ethyl ester as a crude white solid (2.86 g, 97%): $^1$H NMR (DMSO-d$_6$, 300 MHz) δ 8.85 (br t, J=6.0 Hz, 1H), 7.85 (d, J=9.0 Hz, 1H), 7.50 (dd, J$_1$=9.7 Hz, J$_2$=1.7 Hz, 1H), 7.38–7.28 (m, 3H), 6.68–6.65 (m, 1H), 4.96 (s, 2H), 4.49 (d, J=6.0 Hz, 2H), 4.16 (q, J$_1$=14.3 Hz, J$_2$=1.7 Hz, 2H), 3.79 (s, 3H), 1.18 (t, J=6.6 Hz, 3H).

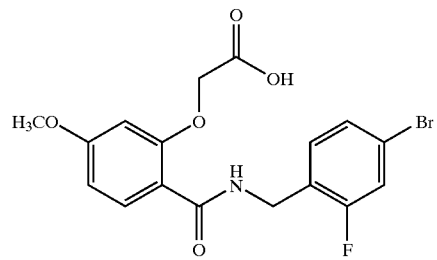

Step 4: [2-(4-Bromo-2-fluoro-benzylcarbamoyl)-5-methoxy-phenoxy]-acetic Acid

A solution of [2-(4-bromo-2-fluoro-benzylcarbamoyl)-5-chloro-phenoxy]-acetic acid ethyl ester (1.23 g, 2.8 mmol) in ethanol (16 mL, 0.18 M) was cooled to 0° C. and treated with aq NaOH (1.25 M, 7.0 mL, 8.7 mmol). After stirring for 2.5 h, the solution was warmed to room temperature and stirred an additional 24 h. Next, the solution was acidified to pH 1–2 with 2 N HCl, diluted with ethyl acetate and washed with saturated aq NaCl. The organic layer was dried over Na$_2$SO$_4$, filtered and concentrated to give [2-(4-bromo-2-fluoro-benzylcarbamoyl)-5-methoxy-phenoxy]-acetic acid as a white solid (1.03 g, 89%): mp 203–204° C.; R$_f$ 0.10 (10% methanol in dichloromethane); $^1$H NMR (DMSO-d$_6$, 300 MHz) δ 9.02 (br t, J=5.9 Hz, 1H), 7.84, (d, J=8.2 Hz, 1H), 7.50, (br d, J=8.7 Hz, 1H), 7.48–7.29 (m, 2H), 6.69–6.80 (m, 2H), 4.87 (s, 2H), 4.49 (d, J=5.8 Hz, 2H), 3.79 (s, 3H). ESI-LC/MS m/z calcd for C$_{17}$H$_{15}$BrFNO$_5$: 411.0; found 412.0 (M+1)$^-$. Anal. calcd for C$_{17}$H$_{15}$BrFNO$_5$: C, 49.53; H, 3.67; N, 3.40. Found C, 49.48; H, 3.68; N, 3.39.

EXAMPLE 17

[2-(4-Bromo-2-fluoro-benzylcarbamoyl)-4-chloro-phenoxy]-acetic Acid

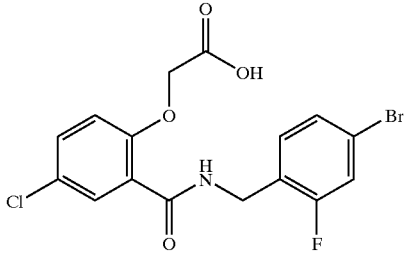

[2-(4-Bromo-2-fluoro-benzylcarbamoyl)-4-chlorophenoxy]-acetic acid was prepared in a manner analogous to that set forth in Example 16, except 5-chlorosalicyclic acid was used in place of 2-hydroxy-4-methoxybenzoic acid in step 1: $R_f$ 0.10 (10% ethyl acetate in dichloromethane); $^1$H NMR (DMSO-d6, 300 MHz) δ 9.13 (br t, J=5.7 Hz, 1H), 7.76 (d, J=2.7 Hz, 1H), 7.55–7.46 (m, 2H), 7.42–7.30 (m, 2H), 7.16 (d, J=8.7 Hz, 1H), 4.86 (s, J=6.3 Hz, 2H), 4.49 (d, J=6.3 Hz, 2H). ESI-LC/MS m/z calcd for $C_{16}H_{12}BrClFNO_4$: 415.0 found 416.5 (M+1)$^+$.

EXAMPLE 18

[2-(4-Bromo-2-fluoro-benzylcarbamoyl)-4-fluoro-phenoxy]-acetic Acid

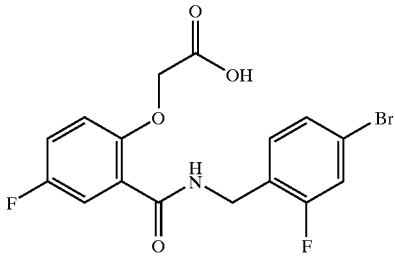

[2-(4-Bromo-2-fluoro-benzylcarbamoyl)-4-fluorophenoxy]-acetic acid was prepared in a manner analogous to that set forth in Example 1, except 5-fluorosalicyclic acid was used in place of 4-chlorosalicyclic acid in step 1: mp 145–146° C.; $^1$H NMR (DMSO-d$_6$, 300 MHz) δ 9.22 (br t, J=5.7 Hz, 1H), 7.56 (dd, J$_1$=9.3 Hz, J$_2$=3.6 Hz, 1H), 7.49 (br dd, J$_1$=9.0 Hz, J$_2$=1.5 Hz, 1H), 7.41–7.29 (m, 3H), 7.16 (dd, J$_1$=9.3 Hz, J$_2$=4.2 Hz, 1H), 4.84 (s, 2H) 4.50 (d, J=5.4 Hz, 2H). ESI-LC/MS m/z calcd for $C_{16}H_{12}BrFNO_4$: 399.0; found 400.0 (M+1)$^+$. Anal. calcd for $C_{16}H_{10}BrFNO_4$: C, 48.02; H, 3.02; N, 3.50. Found C, 48.09; H, 3.05; N, 3.43.

EXAMPLE 19

[2-(4-Bromo-2-fluoro-benzylcarbamoyl)-4-fluoro-phenoxy]-acetic Acid

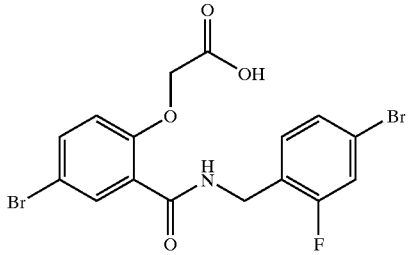

[4-Bromo-2-(4-bromo-2-fluoro-benzylcarbamoyl)-phenoxy]-acetic acid was prepared in an manner analogous to that set forth in Example 1 except 5-bromo-2-hydroxy-benzoic acid was used in place of 4-chloro-2-hydroxy-benzoic acid in step 1: mp 153–155° C.; $R_f$ 0.29 (20% methanol in dichloromethane); $^1$H NMR (DMSO-d$_6$, 300 MHz) δ 9.10 (t, J=12.3 Hz, 1H), 7.88 (dd, J$_1$=1.5 Hz, J$_2$=2.4 Hz, 1H), 7.64 (ddd, J$_1$=8.7 Hz, J$_2$=2.7 Hz, J$_3$=1.2 Hz, 1H), 7.51 (d, J=9.3 Hz, 1H), 7.37–7.53 (m, 2H), 7.10 (dd, J$_1$=8.7 Hz, J$_2$=2.1 Hz, 1H), 4.86 (s, 2H), 4.48 (d, J=6.0 Hz, 2H); ESI-LC/MS m/z calcd for $C_{16}H_{12}Br_2FNO_4$: 458.9. Found 462.0, (M+3)$^+$. Anal. calcd for $C_{16}H_{12}Br_2FNO_4$: C, 41.68; H, 2.62; Br, 34.66; N, 3.04. Found C, 41.82; H, 2.71; Br, 34.38; N, 2.92.

EXAMPLE 20

[2-(4-Bromo-2-fluoro-benzylcarbamoyl)-4-methyl-phenoxy]-acetic Acid

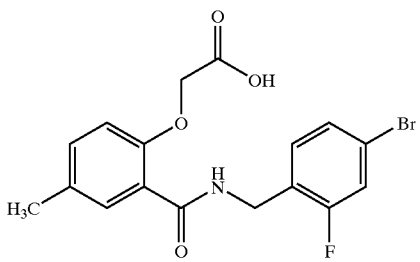

[2-(4-Bromo-2-fluoro-benzylcarbamoyl)-4-methyl-phenoxy]-acetic acid was prepared in a manner analogous to that set forth in Example 16, except 2-hydroxy-4-methylbenzoic acid was used in place of 2-hydroxy-4-methoxybenzoic acid in step 1: mp 145–196° C.; $R_f$ 0.11 (10% methanol in dichloromethane); $^1$H NMR (DMSO-d$_6$, 300 MHz) δ 9.10 (br t, J=6.0 Hz, 1H), 7.49 (br dd, J$_1$=9.0 Hz, J$_2$=2.6 Hz, 1H), 7.40–7.31 (m, 3H), 7.26 (dd, J$_1$=8.7 Hz, J$_2$=2.6 Hz, 1H), 7.00 (d, J=9.0 Hz, 1H), 4.80 (s, 2H), 4.49 (d, J=6.0 Hz, 2H), 2.25 (s, 3H). ESI-LC/MS m/z calcd for $C_{17}H_{15}BrFNO_4$: 395.0 found 394.0 (M−1). Anal. calcd for $C_{17}H_{15}BrFNO_4$: C, 51.53; H, 3.82; N, 3.54. Found C, 51.60, H, 3.88; N, 3.47.

EXAMPLE 21

[2-(4-Bromo-2-fluoro-benzylcarbamoyl)-4-nitro-phenoxy]-acetic

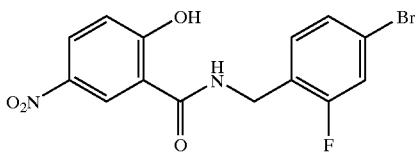

Step 1: N-(4-Bromo-2-fluoro-benzyl)-2-hydroxy-5-nitro-benzamide:

This compound was prepared in a manner analogous to that set forth in Example 1, except 2-hydroxy-5-nitrobenzoic acid was us d in place of the 4-chlorosalicyclic acid in step 1: $^1$H NMR (DMSO-d$_6$, 300 MHz) δ 9.56 (br t, J=5.5 Hz, 1H), 8.83 (s, 1 H), 8. 26 (dd, J$_1$=9.2 Hz, J$_2$=2.7 Hz, 1H), 7.53 (br d, J=9.8 Hz, 1H), 7.43–7.31 (m, 2H), 7.11 (d, J=9.1 Hz, 1 h) 4.52 (d, J=5.5 Hz, 2H).

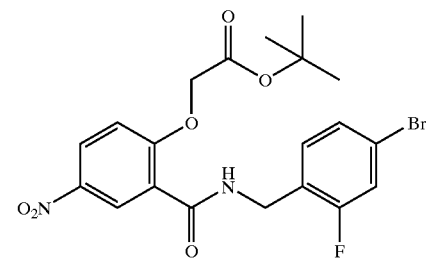

Step 2: [2-(4-Bromo-2-fluoro-benzylcarbamoyl)-4-nitro-phenoxyl-acetic Acid Tert-butyl Ester:

A solution of N-(4-bromo-2-fluoro-benzyl)-2-hydroxy-5-nitro-benzamide (0.95 g, 2.6 mmol) in acetone (15 mL, 0.2 M) was treated with aq K$_2$CO$_3$ (2 M, 1.9 mL, 3.8 mmol) and t-butyl bromoacetate (2.2 mL, 8.4 mmol). After heating to 50° C. for 30 h, the reaction was acidified to pH 1–2 with 2 N HCl and extracted with ethyl acetate (3×). The combined organic extracts were washed with saturated aq NaCl, dried over Na$_2$SO$_4$, filter ed and concentrated. The crude oil was crystallized from heptane and ethyl acetate to give [2-(4-bromo-2-fluoro-benzylcarbamoyl)-4-nitro-phenoxy]-acetic acid tert-butyl ester as a white crystalline solid (1.21 g, 97%): $^1$H NMR (DMSO-d$_6$, 300 MHz) δ 9.01 (br t, J=5.7 Hz, 1H), 8.58 (d, J=3.0 Hz, 1H), 8.33 ( dd, J$_1$=9.0 Hz, J$_2$=3.0 Hz, 1H), 7.51 (br d, J=9.6 Hz, 1H), 7.42–7.34 (m, 2H), 7.32 (d, J=9.3 Hz, 1H), 4.99 (s, 2H), 4.52 (d, J=5.7 Hz, 2H), 1.40 (s, 9H).

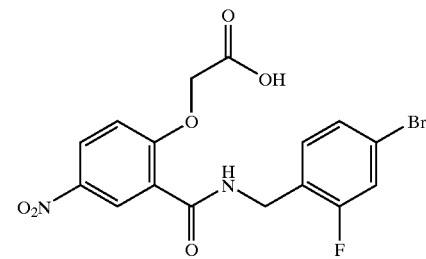

Step 3: [2-(4-Bromo-2-fluoro-benzylcarbamoyl)-4-nitro-phenoxy]-acetic Acid

A solution of [2-(4-bromo-2-fluoro-benzylcarbamoyl)-4-nitro- phenoxy]-acetic acid tert-butyl ester in dichloromethane (11mL, 0.2 M) was treated with trifluoroacetic acid (3.0 mL, 4.44 g. 39.0 mmol) and stirred for 24 h. The reaction was diluted with H$_2$O and extracted with ethyl acetate (3×). The combined organic extracts were washed with H$_2$O (2×), saturated aq NaCl, dried over MGSO$_4$, filtered and concentrated to a crude solid that was recrystallized from heptane and ethyl acetate to give [2-(4-bromo-2-fluoro-benzylcarbamoyl)-4-nitro-phenoxy]-acetic acid as a white crystalline solid (0.98 g, 92%); R$_f$ 0.10 (10% ethyl acetate in dichloromethane); $^1$H NMR (DMSO-d$_6$, 300 MHz) δ 9.14 (br t, J=6.0 Hz, 1H), 8.58 (d, J=3.3 Hz, 1H), 8.34 (dd, J$_1$=9.0 Hz, J$_2$=3.0 Hz, 1H), 7.52 (br dd, J$_1$=9.3 Hz, J$_2$=3.0 Hz, 1H), 7.43–7.32 ( m, 3H), 5.02 (s, 2H), 4.52 (d, J=6.0 Hz, 2H). ESI-LC/MS m/z calcd for C$_{16}$H$_{12}$BrFN$_2$O$_6$: 426.0 found 427.0 (M+1)$^+$. Anal. calcd for C$_{16}$H$_{12}$BrFN$_2$O$_6$: C, 25 44.99; H, 2.83; N, 6.56. Found C, 44.97; H, 2.83; N, 6.47.

EXAMPLE 22

[2-(4 Bromo-2-fluoro-benzylcarbamoyl)-5-methyl-phenoxy]-acetic Acid

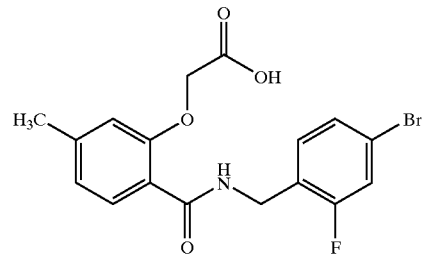

[-(4-Bromo-2-fluoro-benzylcarbamoyl)-5-methyl-phenoxy]-acetic acid was prepared in a manner analogous to that set forth in Example 16, except 2-hydroxy-4-methylbenzoic acid was used i place of 2-hydroxy-4-methoxybenzoic acid in step 1: mp 188–189° C.; R$_f$ 0.10 (10% ethyl acetate in dichloromethane); $^1$H NMR (DMSO-d$_6$, 300 MHz) δ 8.89 (br t, J=6.0 Hz, 1H), 7.57 (d, J=7.8 Hz, 1H), 7.30 (dd, J$_1$=10.5 Hz, J$_2$=1.5 Hz, 1H), 7.20–7.08 (m, 2H), 6.76 (s, 1H), 6.69 (d, J=8.1 Hz, 1H), 4.64 ( s, 2H), 4.29 (d, J=6.0 Hz, 2H), 2.12 (s, 3H). ESI-LC/MS m/z calcd for C$_{17}$H$_{15}$BrFNO$_4$: 395.0 found 394.0 (M−1)$^-$. Anal. calcd for C$_{17}$H$_{15}$BrFNO$_4$: C, 51.53; H, 3.82; N, 3.54. Found C, 51. 42; H, 3.88; N, 3.53.

EXAMPLE 23

[2- 4-Bromo-2-fluoro-benzylcarbamoyl)-phenoxy]-acetic Acid

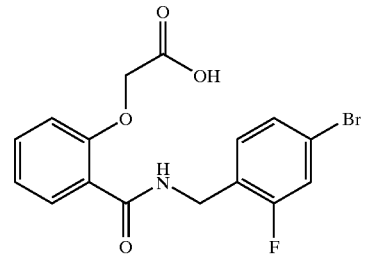

[2-(4-Bromo-2-fluoro-benzylcarbamoyl)-phenoxy]-acetic acid was prepared in a manner analogous to that set forth in Example 16, except salicyclic acid was used in place of 2-hydroxy-4-methoxybenzoic acid in step 1: mp 144–145° C.; $R_f$ 0.10 (10% methanol in dichloromethane); $^1$H NMR (DMSO-$d_6$, 300 MHz) δ 9.11 (br t, J=6.0 Hz, 1H), 7.84 (dd, $J_1$=7.8 Hz, $J_2$=1.8 Hz, 1 H), 7. 4–7.43 (m, 3H), 7.41–7.32 (m, 1H), 7.08 (dd, $J_1$=14.1 Hz, $J_2$=7.5 Hz, 2H), 4.86 (s, 2H), 4.50 (d, J=5.7 Hz, 2 H). ESI-LC/MS m/z calcd for $C_{16}H_{13}BrFNO_4$: 381.0 found 382.0 (M+1). Anal. calcd for $C_{16}H_{13}BrFNO_4$: C, 50.28; H, 3.43; N, 3.66. Found C, 50.36; H, 3.49; N, 3.62.

EXAMPLE 24

[2 (4-Bromo-2-fluoro-benzylcarbamoyl)-5-methylsulfanyl-phenoxy]-acetic Acid

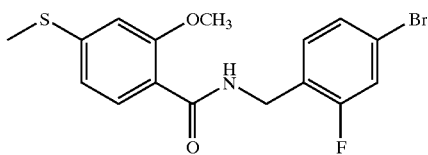

Step 1: N-(4-Bromo-2-fluoro-benzyl)-2-methoxy-4-methylsulfanyl-benzamide:

A solution of 2-methoxy-4-(methylthio)benzoic acid (5.0 g, 25.2 mmol) in dichloromethane (50 mL) was cooled to 0° C. and treated with oxalyl chloride (6.6 mL, 75.6 mmol). A drop of N,N-dimethylformamide was added and the reaction was heated to a gentle reflux for 2 h. After cooling to room temperature, the solution was concentrated in vacuo to remove the excess oxalyl chloride, diluted with dichloromethane (53 mL) and cooled to 0° C. The resulting solution was treated with N,N-diisopropylethylamine (11.6 mL, 67 mmol) and 4-bromo-2-fluorobenzylamine hydrochloride (9.7 g, 40.2 mmol). The resulting solution was stirred at room temperature overnight, concentrated in vacuo, diluted with ethyl acetate and successively washed with 2 N HCl and saturated NaCl. The organic layer was dried over MgSO$_4$, filtered and concentrated. $R_f$ 0.4 (40% ethyl acetate in heptane); $^1$H NMR (DMSO-$d_6$ 300 MHz) δ 8.63 (t, J=6 Hz, 1H), 7.70 (d, J=8.1 Hz, 1H), 7.50 (dd, $J_1$=9.6 Hz, $J_2$=2.1 Hz, 1H), 7.38 (dd, $J_1$=8.4 Hz, $J_2$=2.0 Hz , 1H), 7.28 (t, J=8.4 Hz, 1H), 6.94 (br s , 1H), 6.89 (dd, $J_1$=5.7 Hz, $J_2$=1.7 Hz, 1H), 4.46 (d, J=6 Hz, 2 H), 3.91 (s, 3H), 2.51 (s, 3H).

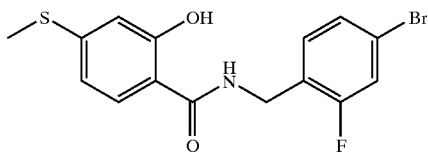

Step 2: N-(4-Bromo-2-fluoro-benzyl)-2-hydroxy-4-methylsylfanyl-benzamide:

A solution of N-(4-bromo-2-fluoro-benzyl)-2-methoxy-4-methylsulfanyl-benzamide (11g crude, from step 1) was dissolved in a 25% HBr in glacial acetic acid solution (400 mL) and heated to 100° C. for 4 h. The solution was diluted with ethyl acetate (750 mL) and washed with saturated NaCl (500 mL). The organic layer was dried over MgSO$_4$, filtered and concentrated. Purification by MPLC (10–100% ethyl acetate in heptane, 23 mL/min, 75 min) gave N-(4-bromo-2-fluoro-benzyl)-2-hydroxy-4-methylsulfanyl-benzamide (5.0 g, 50%). $R_f$ 0.57 (40% ethyl acetate in heptane); $^1$H NMR (DMSO-$d_6$ 300 MHz) δ 12.57 (s, 1H), 9.22 (t, J=5.4 Hz, 1H), 7.78 (d, J=8.4 Hz, 1H), 7.52 (dd, $J_1$=9.8 Hz, $J_2$=1.7 Hz, 1H), 7.40–7.27 (m, 2H), 6.77–6.71 (m, 2H), 4.46 (d, J=5.7 Hz, 2H), 2.46 (5, 3H).

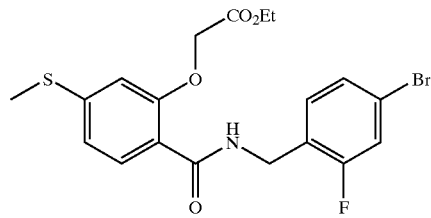

Step 3: [2-(4-Bromo-2-fluoro-benzylcarbamoyl)-5-methylsylfanyl-phenoxy]-acetic Acid Ethyl Ester:

A solution of N-(4-bromo-2-fluoro-benzyl)-2-hydroxy-4-methylsylfanyl-benzamide (5.0 g, 13.5 mmol) in acetone (27 mL) was treated with 2 N $K_2CO_3$ (10 mL, 20.3 mmol) and ethyl bromoacetate (2.2 mL, 20.3 mmol). The reaction was heated to 50° C. for 4 h, cooled to room temperature and acidified to pH 1 with aq 2 N HCl. The product was extrated with ethyl acetate and washed with saturated NaCl. The organic layer was dried over MgSO$_4$, filtered and concentrated. The light brown solid was suspended in heptane and dichloromethane. The solid was washed wit h heptane to give the [2-(4-bromo-2-fluoro-benzylcarbamoyl)-5-methylsylfanyl-phenoxy]-acetic acid ethyl ester (5.3 9, 86%): $R_f$ 0.45 (40% ethyl acetate in heptane); $^1$H NMR (DMSO-$d_6$ 300 MHz) δ 8.90 (t, J=6 Hz, 1H), 7.80 (d, J=8.4 Hz, 1H) 7.50 (dd, $J_1$=9.9 Hz, $J_2$=1.7 Hz, 1H), 7.39–7.29 (m, 2H) 6.97–6.93 (m, 2H), 5.0 (s, 2H), 4.5 0 (d, J=6.0 Hz, 2H) 4.17 (q, J=7.1 Hz, 2H) 1.919 (t, J=7.2 Hz, 3H).

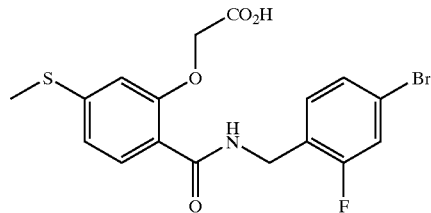

Step 4: [2-(4-Bromo-2-fluoro-benzylcarbamoyl)-5-methylsylfanyl-phenoxy]-acetic Acid:

A suspension of [2-(4-bromo-2-fluoro-benzylcarbamoyl)-5-methylsylfanyl-phenoxy-acetic acid ethyl ester (1.0 g, 2.19 mmol) in ethanol (11 mL) was treated with 2 N NaOH (6.6 mL, 13.2 mmol) . The reaction was stirred at room temperature for 2 h, concentrated in vacuo and acidified with aq 2 N HCl to pH 1. The mixture was diluted with ethyl acetate and washed with saturated NaCl. The organic layer was dried over MgSo$_4$, filtered and concentrated to give [2-(4-bromo-2-fluoro-benzylcarbamoyl)-5-methylsylfanyl-phenoxy]-acetic acid (0.8 g, 85%) as white crystalline solid: mp 196–199° C.; $R_f$ 0 0.3 (20% methanol in dichloromethane); $^1$H NMR (DMSO-$d_6$ 300 MHz) δ 9.16 (t, J 6.0 Hz, 1H), 7.7 9 (d, J=8.7 Hz, 1H), 7.48 (dd, $J_1$=28.7 Hz, $J_2$=1.5 Hz, 1H), 7.36–7.32 (m, 2H), 6.95–6.90 (m, 2H), 4.87 (s, 2H), 4.48 (d, J=3.3 Hz, 2H), 2.49 (s, 3H). ESI-LC/MS m/z calcd for calcd for $C_{17}H_{15}BrFNO_4S$: 428.3; Found 427.0 (M−1)$^-$. Anal. calcd for $C_{17}H_{15}BrFNO_4S$: C, 47.68; H, 3.53; N, 3.27; S, 7.49. Found C, 47.70; H, 3.47; N, 3.22; S, 7.38.

EXAMPLE 25

[2-(3-Nitro-benzylcarbamoyl)-4-methyl-phenoxy]-acetic Acid

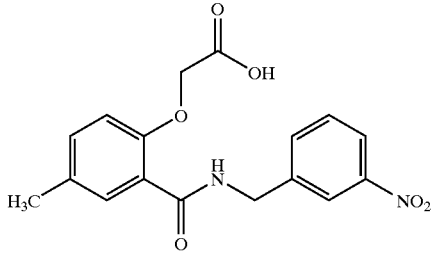

[2-(3-Nitro-benzylcarbamoyl)-4-methyl-phenoxy]-acetic acid was prepared in a manner analogous to that set forth in Example 1, except 5-methylsalicylic acid was used in place of 4-chlorosalicylic acid; and 3-nitrobenzylamine hydrochloride was used in place of 4-bromo-2-fluorobenzylamine hydrochloride in step 1: mp 193–194° C.; $R_f$ 0.48 (20% methanol in dichloromethane); $^1$H NMR (DMSO-$d_6$ 300 MHz) δ 13.37 (br s, 1H), 9.26 (t, J=6 Hz, 1H), 8.18 (t, J=1.8 Hz, 1H), 8.09 (ddd, $J_1$=8.3 Hz, $J_2$=2.3 Hz, $J_3$=1.0 Hz, 1H), 7.79 (d, J=7.5 Hz, 1H), 7.65–7.58 (m, 2H), 7.26 (ddd, $J_1$=8.4 Hz, $J_2$=2.4 Hz, $J_3$=0.6 Hz, 1H), 7.00 (d, J=8.1 Hz, 1H), 4.82 (s, 2 H), 4.62 (d, J=6 Hz, 2H), 2.25 (s, 3H). ESI-LC/MS m/z calcd for $C_{17}H_{16}N_2O_6$: 344.3; Found 345.0 (M+1)$^+$. Anal. calcd for $C_{17}H_{16}N_2O_6$: C, 59.30; H, 4.68; N, 8.14. Found C, 59.10; H, 4.78; N, 7.90.

EXAMPLE 26

[2-(3-nitro-benzylcarbamoyl)-4-trifluoromethoxy-phenoxy]-acetic Acid

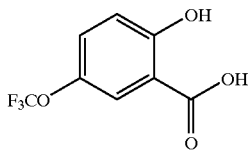

Step 1: 2-Hydroxy-5-trifluoromethoxy-benzoic Acid

To a stirring solution of NaOH (8.15 g, 203.8 mmol) in water (35 mL, 5.8 M) was added an aq solution of silver nitrate (17.3 g, 101.9 mmol, 35 mL water, 2.9 M). A brownish solid formed. The flask was placed in an ice bath and to the stirring suspension was added 2-hydroxy-5-trifluoromethoxy-benzaldehyde in 500 mg portions (10.0 g, 48.5 mmol). After addition was complete and the reaction was stirred for 10 min in an ice bath, the mixture was filtered and the brownish precipitate was washed with hot water. The combined washings were acidified with conc HCl to pH 1 and the precipitate was collected by vacuum filtration. This solid was then dissolved in ethyl acetate. The ethyl acetate was washed with saturated aq NaCl, dried over $Na_2SO_4$, and filtered. The aqueous layer was also extracted with ethyl acetate. This organic layer was washed with saturated aq NaCl, dried over $Na_2SO_4$, filtered and concentrated to provide 2-hydroxy-5-trifluoromethoxy-benzoic acid (9.8 g, 91%) as a white solid: $R_f$ 0.38 (20% methanol in dichloromethane); $^1$H NMR (CDCl$_3$, 300 MHz) δ 10.30 (bs, 1H), 7.79 (d, J=3.0 Hz, 1H), 7.41 (dd, $J_1$=9.3 Hz, $J_2$=3.0 Hz, 1H), 7.05 (d, J=9.0 Hz, 1H).

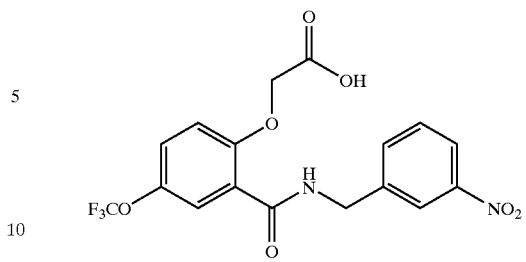

Step 2: [2-(3-nitro-benzylcarbamoyl)-4-trifluoromethoxy-phenoxy]-acetic Acid

[2-(3-Nitro-benzylcarbamoyl)-4-trifluoromethoxy-phenoxy]-acetic acid was prepared in a manner analogous to that set forth in Example 1 except in step 1, 2-hydroxy-5-trifluoromethoxy-benzoic acid was used in place of 4-chloro- 2-hydroxy-benzoic acid and 3-nitrobenzylamine hydrochloride was used in place of 4-bromo-2-fluorobenzylamine hydrochloride: mp 154–156° C.; $R_f$ 0.38 (20% methanol in dichloromethane); $^1$H NMR (DMSO-$d_6$ 300 MHz) δ 9.30 (t, J=6.0 Hz, 1H), 8.20 (s, 1H), 8.10 (ddd, $J_1$=8.1 Hz, $J_2$=3.3 Hz, $J_3$=1.2 Hz, 1H), 7.81 (d, J=7.8 Hz, 1H), 7.74 (dd, $J_1$=3.6 Hz, $J_2$=0.06 Hz, 1H), 7.62 (t, J=7.8 Hz, 1H), 7.51 (ddd, $J_1$=9.6 Hz, $J_2$=3.2 Hz, $J_3$=0.6 Hz, 1H), 7.24 (d, J=9.0 Hz, 1H), 4.92 (s, 2H), 4.63 (d, J=6.3 Hz, 2H); ESI-LC/MS m/z calcd for $C_{17}H_{13}F_3N_2O_7$: 414.07. Found 413 (M−1)$^-$. Anal. calcd for $C_{17}H_{13}F3N_2O_7$: C, 49.28; H, 3.16; N, 6.76. Found C, 49.19; H, 3.23; N, 6.67.

EXAMPLE 27

[5-Fluoro-2-(3-nitro-benzylcarbamoyl)-phenoxyl-acetic Acid

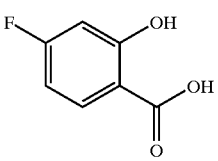

Step 1: 4-Fluoro-2-hydroxy-benzoic Acid:

A solution of 2,4-difluorobenzoic acid (100 g, 0.63 mol) in 1,3-dimethyl-2-imidazolidinone (1,400 mL, 0.45 M) was treated with sodium hydroxide (88 g, 2.2 mol) and heated to 135° C. After stirring for 4 h, the solution was cooled 0° C., dissolved in water (100 mL), and transferred to a 5 L Erlenmeyer flask and carefully treated with aq HCl (2,800 mL, 2 N). After filtering off the crude product, the precipitate was dissolved in ethyl acetate, dried over sodium sulfate and decolorizing charcol, and filtered. The solution was concentrated under reduced pressure and recrystallized from ethyl acetate and heptane to give 4-fluorosalicylic acid (2 crops, 67 g, 68%) as off-white needles. mp: 188–189° C.; $R_f$ 0.26 (20% methanol in dichloromethane).

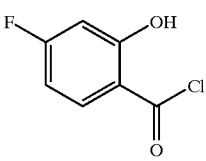

Step 2: 4-Fluoro-2-hydroxy-benzoyl Chloride:

A suspension of 4-fluoro-2-hydroxy-benzoic acid (15 g, 96.1 mmol) in heptane (190 mL) was treated with thionyl chloride (21 mL, 288 mmol) in a dropwise manner over 30 min. A drop of N,N-dimethylformamide was added and the solution was heated for 4 h at 60° C. The excess thionyl chloride was distilled off under reduced pressure. The remaining solution was cooled to room temperature, filtered, and concentrated to give 4-fluoro-2-hydroxy-benzoyl chloride as a pale yellow crystalline solid (14.2 g, 85%).

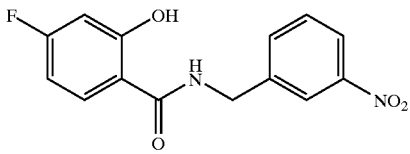

Step 3: 4-Fluoro-2-hydroxy-N-(3-nitro-benzyl)-benzamide:

A solution of 4-fluoro salicylic acid chloride (12.3 g, 70.3 mmol) in dichloromethane (140 mL) was cooled to 0° C., and treated with N,N-diisopropylethylamine (31.0 mL, 175 mmol) and 3-nitrobenzylamine hydrochloride (16 g, 84.6 mmol). After stirring at room temperature for 24 h, the solution was concentrated in vacuo and diluted with ethyl acetate. The organic layer was washed successively with aq 2 N HCl and saturated aq NaCl, dried over MgSO$_4$, filtered and concentrated.

Purification by MPLC (10–100% ethyl acetate in heptane, 23 mL/min, 75 min) provided 4-fluoro-2-hydroxy-N-(3-nitro-benzyl)-benzamide as a yellow solid (13.7 g, 67%): $^1$H NMR (DMSO-d$_6$ 300 MHz) δ 12.75 (s, 1H), 9.43 (t, J=6.0 Hz, 1H), 8.11 (ddd, J$_1$=8.3, J$_2$=2.1 Hz, J$_3$=1.2 Hz, 1H), 8.18 (t, J=1.5 Hz, 1H), 7.94 (dd, J$_1$=8.9 Hz, J$_2$=6.5 Hz, 1H), 7.78 (td, J$_1$=7.8 Hz, J$_2$=1.4 Hz, 1H), 7.63 (t, J=8.0 Hz, 1H), 6.81–6.72 (m, 2H), 4.61 (d, J=5.7 Hz, 2H).

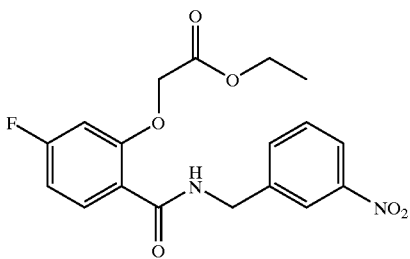

Step 4: [5-Fluoro-2-(3-nitro-benzylcarbamoyl)-phenoxy]-acetic Acid Ethyl Ester:

A solution of 4-fluoro-2-hydroxy-N-(3-nitro-benzyl)-benzamide (5.00 g, 17.2 mmol) in acetone (86.0 mL) was treated with aq 2 N K$_2$CO$_3$ (13.0 mL, 25.8 mmol) and ethyl bromoacetate (1.50 mL, 9.66 mmol) and heated to 50° C. for 2 h. The solution was cooled to 0° C. and acidified to pH of 1 with 2 N HCl. The solution was diluted with ethyl acetate and washed with saturated aq NaCl. The organic layer was dried over MgSO$_4$, filtered and concentrated. Purification by MPLC(10–100% ethyl acetate in heptane, 23 mL/min, 75 min) to give [5-fluoro-2-(3-nitro-benzylcarbamoyl)-phenoxy]-acetic acid ethyl ester as a pale yellow solid (6 g, 93%): mp 78–80° C.; R$_f$ 0.26 (40% ethyl acetate in heptane); $^1$H NMR (DMSO-d$_6$ 300 MHz) δ 9.01 (t, J=6 Hz, 1H), 8.19 (t, J=1.8 Hz, 1H), 8.10 (dd, J$_1$=8.1 Hz, J$_2$=1.5 Hz, 1H), 7.89 (dd, J$_1$=8.7 Hz, J$_2$=6.9 Hz, 1H),7.79 (d, J=7.5 Hz, 1H), 7.61 (t, J=8.1 Hz, 1H), 7.11 (dd, J$_1$=11.1 Hz, J$_2$=2.4 Hz, 1H), 6.92 (dt, J$_1$=8.4 Hz, J$_2$=2.4 Hz, 1H), 5.0 (s, 2H), 4.63 (d, J=6.3 Hz, 2H), 4.15 (q, J=7.2 Hz, 2H) 1.17 (t, J=6.5 Hz, 3H). ESI-LC/MS m/z calcd for C$_{18}$H$_{17}$FN$_2$O$_6$: 376.4. Found 377.0 (M+1)$^+$. Anal. calcd for C$_{18}$H$_{17}$FN$_2$O$_6$: C, 57.45; H, 4.55; N, 7.44. Found : C, 57.47; H, 4.64; N, 7.28.

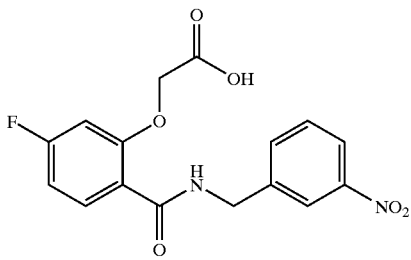

Step 5: [5-Fluoro-2-(3-nitro-benzylcarbamoyl)-phenoxy]-acetic Acid:

A suspension of [5-fluoro-2-(3-nitro-benzylcarbamoyl)-phenoxy]-acetic acid ethyl ester (3.3 g, 8.77 mmol) in ethanol (40 mL) was treated with aq 2 N NaOH (24 mL, 47.8 mmol). After stirring for 4 h, the solution was concentrated in vacuo until most of the ethanol was removed, and the mixture was acidified to pH of 1 with 2 N HCl. After extracting with ethyl acetate, the organic layer was washed with saturated aq NaCl, dried over MgSO; and concentrated to give [5-fluoro-2-(3-nitro-benzylcarbamoyl)-phenoxy]-acetic acid as an off-white solid (3.00 g, 98%): mp 148–151° C.; R$_f$ 0.39 (20% methanol in dichloromethane); $^1$H NMR (DMSO-d$_6$ 300 MHz) δ 9.20 (t, J=6.3 Hz, 1H) 8.18 (s, 1H), 8.09 (dd, J$_1$=7.2 Hz, J$_2$=2.7 Hz, 1 H), 7.90 (dd, J$_1$=8.7 Hz, J$_2$=7.0 Hz, 1H), 7.79 (d, J=7.5 Hz, 1H), 7.61 (t, J=7.8 Hz, 1H), 7.08 (dd, J$_1$=10.8 Hz, J$_2$=2.1 Hz, 1H), 6.91 (dt, J$_1$=8.7 Hz, J$_2$=2.4 Hz, 1H), 4.89 (s, 2H), 4.62 (d, J=6 Hz, 2H). ESI-LC/MS m/z calcd for C$_{16}$H$_{13}$FN$_2$O$_6$: 348.3; Found 347.0 (M−1)$^-$. Anal. calcd for C$_{16}$H$_{13}$FN$_2$O$_6$: C, 55.18; H, 3.76; N, 8.04. Found C, 55.02; H, 3.79; N, 7.98.

EXAMPLE 28

[2-(4-Bromo-2-fluoro-benzylcarbamoyl)-5-fluoro-phenoxy]-acetic Acid

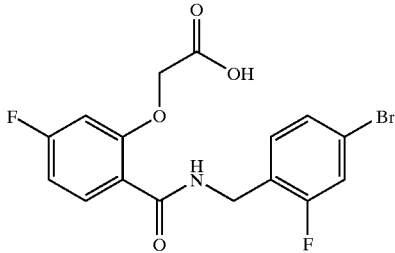

[2-(4-Bromo-2-fluoro-benzylcarbamoyl)-5-fluoro-phenoxy]-acetic acid was prepared in a manner analogous to that set forth in Example 1, except 4-fluorosalicylic acid (Example 27) was used in place of 4-chlorosalicylic acid in step 1: mp 143–145° C.; R$_f$ 0.43 (20% methanol in dichloromethane); $^1$H NMR (DMSO-d$_6$ 300 MHz) δ 13.37 (br s, 1H), 9.03 (t, J=6 Hz, 1H), 7.91 (dd, J$_1$=8.6 Hz, J$_2$=7.1 Hz, 1H), 7.50 (d, J=9.9 Hz, 1H), 7.37–7.36 (m, 2H), 7.09 (dd, J$_1$=11.0 Hz, J$_2$=2.4 Hz, 1H), 6.92 (dt, J$_1$=8.4 Hz, J$_2$=2.4 Hz, 1H), 4.90 (s, 2H), 4.50 (d, J=5.4 Hz, 2H). ESI-LC/MS m/z calcd for C$_{16}$H$_{12}$BrF$_2$NO$_4$: 400.2; Found 400.5, 402.0 (M, M+2)$^+$. Anal. calcd for C$_{16}$H$_{12}$BrF$_2$ NO$_4$: C, 48.02; H, 3.02; N, 3.50. Found : C, 48.07; H, 3.08; N, 3.41.

EXAMPLE 29

[5-Fluoro-2-(4-methyl-3-nitro-benzylcarbamoyl)-phenoxy]-acetic

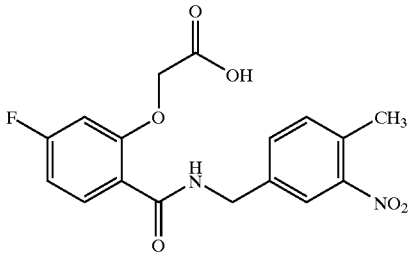

[5-Fluoro-2-(4-methyl-3-nitro-benzylcarbamoyl)-phenoxy]-acetic acid was prepared in a manner analogous to that set forth in Example 1, except 4-fluorosalicylic acid (Example 27) was used in place of 4-chlorosalicylic acid; and 4-methyl-3-nitrobenzylamine was used in place of 4-bromo-2-fluorobenzylamine hydrochloride in step 1: mp 159–160° C.; $R_f$ 0.48 (20% methanol in dichloromethane); $^1$H NMR (DMSO-$d_6$ 300 MHz) δ 13.37 (br s, 1H), 9.12 (t, J=5.9 Hz, 1H), 7.92–7.87 (m, 2H), 7.58 (d, J=8.7 Hz, 1H), 7.43 (d, J=8.1 Hz, 1H), 7.07 (d, J=10.8 Hz, 1H), 6.91 (t, J=8.6 Hz, 1H), 4.8,9 (s, 2H), 4.55 (d, J=6 Hz, 2H), 2.46 (s, 3H). ESI-LC/MS m/z calcd for $C_{17}H_{15}FN_2O_6$: 362.3; Found 361.0 (M−1)$^-$. Anal. calcd for $C_{17}H_{15}FN_2O_6$: C, 56.36; H, 4.17; N, 7.73. Found : C, 56.18; H, 4.22; N, 7.60.

EXAMPLE 30

[2-(4-Bromo-2-fluoro-benzylcarbamoyl)-4,5-difluoro-phenoxy]-acetic Acid

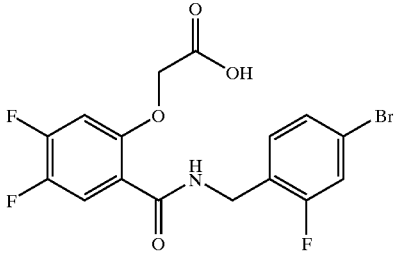

[2-(4-Bromo-2-fluoro-benzylcarbamoyl)-4,5-difluoro-phenoxy]-acetic acid was prepared in a manner analogous to that set forth in Example 27, except 2,4,5-trifluorosalicylic acid was used in place of 2,4-difluorosalicylic acid in step 1; and 4-bromo-2-fluorobenzylamine hydrochloride was used in place of 3-nitrobenzylamine hydrochloride in step 3: mp 156–158 0C; $R_f$ 0.26 (20% methanol in dichloromethane); $^1$H NMR (DMSO-$d_6$ 300 MHz) δ 9.11 (t, J=5.6 Hz, 1H), 7.80 (dd, $J_1$=11.4 Hz, $J_2$=9.6 Hz, 1H), 7.50 (dd, $J_1$=9.6 Hz, $J_2$=1.8 Hz, 1H), 7.44–7.34 (m, 3H), 4.87 (s, 2H), 4.49 (d, J=5.7 Hz, 2H). ESI-LC/MS m/z calcd for $C_{16}H_{11}BrF_3NO_4$: 418.2; Found 417.0 (M−1)$^-$. Anal. calcd for $C_{16}H_{11}BrF_3NO_4$: C, 45.96; H, 2.65; N, 3.35. Found: C, 45.96; H, 2.65; N, 3.35.

EXAMPLE 31

[2-(4-Bromo-2-fluoro-benzylcarbamoyl)-3,5-difluoro-phenoxy]-acetic Acid

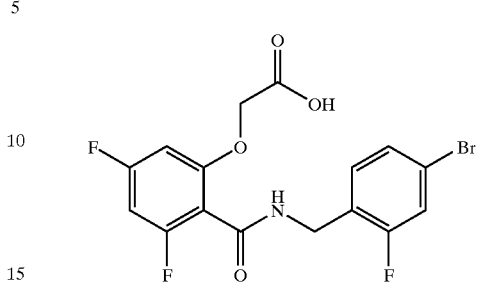

[2-(4-Bromo-2-fluoro-benzylcarbamoyl)-3,5-difluoro-phenoxy]-acetic acid was prepared in a manner analogous to that set forth in Example 27, except 2,4,6-trifluorosalicylic acid was used in place of 2,4-difluorosalicylic acid in step 1; and 4-bromo-2-fluorobenzylamine hydrochloride was used in place of 3-nitrobenzylamine hydrochloride in step 3: mp 158–159° C.; Anal. calcd for $C_{16}H_{11}BrF_3NO_4$: C, 45.96; H 2.65; N, 3.35. Found: C, 46.05; H, 2.61; N, 3.45.

EXAMPLE 32:

5-Fluoro-2-(3-nitro-benzylthiocarbamoyl)-phenoxy]-acetic Acid

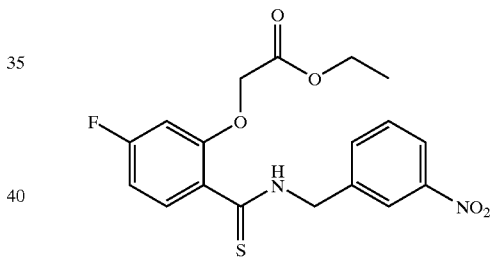

Step 1: [5-Fluoro-2-(3-nitro-benzylthiocarbamoyl)-phenoxy]-acetic Acid Ethyl Ester:

In a flame dried flask under a nitrogen atmosphere, a suspension of phosphorus pentasulfide (0.77 g, 1.73 mmol) in pyridine (6.9 mL) was treated with [5-fluoro-2-(3-nitro-benzylcarbamoyl)-phenoxy]-acetic acid ethyl ester (Example 27, 1.3 g, 3.45 mmol) and heated to 115° C. for 4 h. After cooling to room temperature, the mixture was diluted with water and ethyl acetate. The organic layer was washed successively with 2 N HCl and saturated NaCl, dried over MgSO$_4$, and concentrated. The dark orange solid was filtered through a short pad of silica and again concentrated to give [5-fluoro-2-(3-nitro-benzylthiocarbamoyl)-phenoxy]-acetic acid ethyl ester as an orange solid (1.2 g, 89%): mp 118° C.; $R_f$ 0.43 (40% ethyl acetate in heptane); $^1$H NMR (DMSO-$d_6$ 300 MHz) δ 10.71 (s, 1H), 8.23 (s, 1H), 8.12 (d, J=8.1 Hz, 1H), 7.83 (d, J=7.8 Hz, 1H), 7.71–7.60 (m, 2H), 7.04 (dd, $J_1$=11.1 Hz, $J_2$=2.4 Hz, 1H), 6.87 (dt, $J_1$=8.4 Hz, $J_2$=2.4 Hz, 1H), 5.07 (d, J=3.3 Hz, 2H), 4.89 (s, 2H), 4.13 (q, J=6.7 Hz, 2H), 1.17 (t, J=5.7 Hz, 3H). ESI-LC/MS m/z calcd for $C_{18}H_{17}FN_2O_5S$: 394.1. Found 393.0 (M+1)$^+$. Anal. calcd for $C_{18}H_{17}FN_2O_5S$: C, 55.09; H, 4.37; N, 7.14. Found C, 54.98; H, 4.36; N, 7.08.

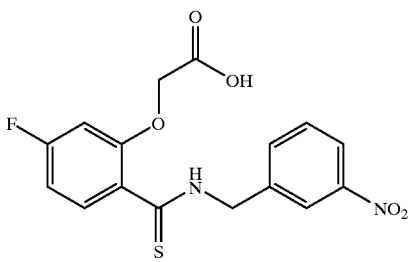

Step 2: [5-Fluoro-2-(3-nitro-benzylthiocarbamoyl)-phenoxy]-acetic Acid:

A suspension of [5-Fluoro-2-(3-nitro-benzylthiocarbamoyl)-phenoxy]-acetic acid ethyl ester (4.39 g, 11.2 mmol) in ethanol (40 mL) was treated with aq 2 N NaOH (11 mL, 22.4 mmol). After stirring for 4 h, the solution was concentrated in vacuo until most of the ethanol was removed, and the mixture was acidified to pH of 1 with 2 N HCl. After extracting with ethyl acetate, the organic layer was washed with saturated aq NaCl, dried over MgSO$_4$ and concentrated to give [5-fluoro-2-(3-nitro-benzylthiocarbamoyl)-phenoxy]-acetic acid (4.0 g, 98%) as an off-white solid: mp 147–150° C.; R$_f$ 0.27 (20% methanol in dichloromethane); $^1$H NMR (DMSO-d$_6$ 300 MHz) δ 13.23 (s, 1H), 10.79 (t, J=5.7 Hz, 1H), 8.23 (t, J=1.8 Hz, 1H), 8.11 (ddd, J$_1$=8.3 Hz, J$_2$=2.7 Hz, J$_3$=1.2 Hz, 1 H), 7.85 (br d, J=7.5 Hz, 1H), 7.73 (dd, J$_1$=8.9 Hz, J$_2$=7.1 Hz, 1H), 7.63 (t, J=8.1 Hz, 1H), 7.03 (dd, J$_1$=11.4 Hz, J$_2$=2.4 Hz, 1H), 6.86 (dt, J$_1$=8.4 Hz, J$_2$=2.4 Hz, 1H), 5.07 (d, J=5.7 Hz, 2H), 4.83 (s, 2H). ESI-LC/MS m/z calcd for C$_{16}$H$_{13}$FN$_2$O$_5$S: 364.4. Found 363.0 (M−1). Anal. calcd for C$_{16}$H$_{13}$FN$_2$O$_5$S: C, 52.74: H, 3.60; N, 7.69. Found C, 52.65; H, 3.62; N, 7.58.

EXAMPLE 33

[2-(4-Bromo-2-fluoro-benzylthiocarbamoyl)-5-fluoro-phenoxy]-acetic Acid

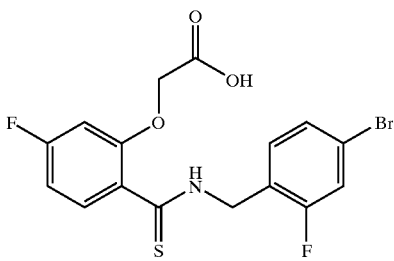

[2-(4-Bromo-2-fluoro-benzylthiocarbamoyl)-5-fluoro-phenoxy]-acetic acid was prepared in a manner analogous to that set forth in Example 32, except [5-fluoro-2-(4-bromo-2-fluoro-benzylcarbamoyl)-phenoxy]-acetic acid ethyl ester (Example 28) was used in place of [5-fluoro-2-(3-nitro-benzylcarbamoyl)-phenoxy]-acetic acid ethyl ester in step 1: mp 154–157° C.; R$_f$ 0.46 (20% methanol in dichloromethane); $^1$H NMR (DMSO-d$_6$ 300 MHz) δ 13.29 (br s, 1H), 10.66 (t, J=5.7 Hz, 1H), 7.73 (dd, J$_1$=8.9 Hz, J$_2$=6.8 Hz, 1H), 7.52 (dd, J$_1$=9. 9 Hz, J$_2$=1.5 Hz, 1H), 7.46–7.36 (m, 2H), 7.04 (dd, J=11.3 Hz, J$_2$=2.3 Hz, 1H), 6.86 (dt, J$_1$=8.4 Hz, J$_2$=2.4 Hz, 1H), 4.90 (d, J=5.7 Hz, 2H), 4.81 (s, 2H). ESI-LC/MS m/z calcd for C$_{16}$H$_{12}$BrF$_2$NO$_3$S: 415.0; Found 416.0 (M+1)$^+$. Anal. calcd for C$_{16}$H$_{12}$BrF$_2$NO$_3$S: C, 46. 17; H, 2.91; N, 3.37; S, 7.70; Br, 19.20. Found: C, 46.17; H, 2.90; N, 3.33; S, 7.62; Br, 19.31.

EXAMPLE 34

[4-Bromo-2-(4-bromo-2-fluoro-benzylthiocarbamoyl)-phenoxy]-acetic Acid

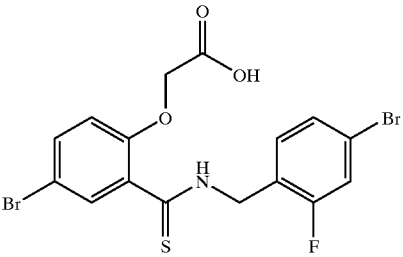

[4-Bromo-2-(4-bromo-2-fluoro-benzylthiocarbamoyl)-phenoxy]-acetic acid was prepared in an manner analogous to that set forth in Example 32 except, [4-bromo-2-(4-bromo-2-fluoro-benzylcarbamoyl)-phenoxy]-acetic acid ethyl ester (Example 19) was used in place of [5-fluoro-2-(3-nitro-benzylcarbamoyl)-phenoxy]-acetic acid ethyl ester in step 1: R$_f$ 30 (20% methanol in dichloromethane); $^1$H NMR (DMSO-d$_6$, 300 MHz) δ 10.78 (t, J=5.9 Hz, 1H), 7.68 (t, J=2.4 Hz, 1H), 7.56–7.51 (m, 2H), 7.46–7.37 (m, 2H), 7.04 (d, J=9.0 Hz, 1 H), 4.87 (bd s, 2H), 4.76 (s, 2H); ESI-LC/MS m/z calcd for C$_{16}$H$_{12}$Br$_2$FNO$_3$S: 474.9. Found 478 (M+3)$^+$. Anal. calcd for C$_{16}$H$_{12}$Br$_2$FNO$_3$S: C, 40.28; H, 2.53; Br, 33.49; N, 2.94; S, 6.72. Found C, 40.42; H, 2.53; Br, 33.31; N, 2.84; S, 6.61.

EXAMPLE 35

[2-(3-Nitro-benzylthiocarbamoyl)-4-trifluoromethoxy-phenoxy]-acetic Acid

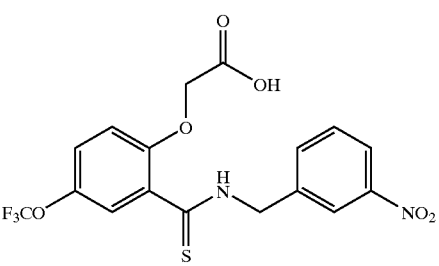

[2-(3-Nitro-benzylthiocarbamoyl)-4-trifluoromethoxy-phenoxy]-acetic acid was prepared in an analogous manner to that set forth in Example 32 except [2-(3-nitro-benzylcarbomoyl)-4-trifluoromethoxy-phenoxy]-acetic acid ethyl ester (Example 26) was used in place of [5-fluoro-2-(3-nitro-benzylcarbamoyl-phenoxy]-acetic acid ethyl ester in step 1,: mp 158–161° C.; R$_f$ 0.40 (20% methanol in dichloromethane); $^1$H NMR (DMSO-d$_6$, 300 MHz) δ 10.95 (t, J=4.4 Hz, 1H), 8.24 (s, 1H), 8.12 (dd, J$_1$=7.8 Hz, J$_2$=2.4 Hz, 1H), 7.85 (d, J=7.8 Hz, 1H), 7.64 (d, J=8.0 Hz, 1H), 7.55 (d, J=3.0 Hz, 1H), 7.40 (dd, J$_1$=8.7 Hz, J$_2$=3.0 Hz, 1H), 7.16 (d, J=9.0 Hz, 1H), 5.07 (d, J=5.7 Hz, 2H), 4.81 (s, 2H); ESI-LC/MS m/z calcd for C$_{17}$H$_{13}$F$_3$N$_2$O$_6$S: 430.04; Found 431.0 (M+1)$^+$. Anal. calcd for C$_{17}$H$_{13}$F$_3$N$_2$O$_6$S: C, 47.44; N, 6.51; H, 3.04; S, 7.45. Found C, 47.16; N, 6.37; H, 3.11; S, 7.58.

EXAMPLE 36

[2-(4-Bromo-2-fluoro-benzylthiocarbamoyl)-4,5-difluoro-phenoxy]-acetic Acid

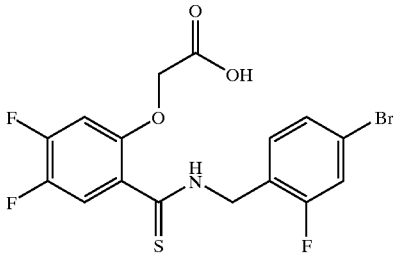

[2-(4-Bromo-2-fluoro-benzylthiocarbamoyl)-4,5-difluoro-phenoxy]-acetic acid was prepared in a manner analogous to that set forth in Example 32, except [4,5-difluoro-2-(4-bromo-2-fluoro-benzylcarbamoyl)-phenoxy]-acetic acid ethyl ester (Example 30) was used in place of 15-fluoro-2-(3-nitro-benzylcarbamoyl)-phenoxy]-acetic acid ethyl ester in step 1: mp 206–209° C.; $R_f$ 0.5 (2.0% methanol in dichloromethane); $^1$H NMR (DMSO-$d_6$ 300 MHz) δ 10.8 (br s, 1H), 7.70 (dt, $J_1$=9.3 Hz, $J_2$=2.1 Hz, 1H), 7.52 (dd, $J_1$=9,9 Hz, $J_2$=2.1 Hz, 1H), 7.45–7.30 (m, 3H), 4.88 (br s, 2H), 4.79 (s, 2H). ESI-LC/MS m/z calcd for $C_{16}H_{11}BrF_3NO_3S$: 434.2; Found 432.0, 433.0 (M−2, M−1)$^-$. Anal. calcd for $C_{16}H_{11}BrF_3NO_3S$: C, 44.26; H, 2.55; N, 3.23; S, 7.38. Found C, 44.43; H, 2.64; N, 3.12; S, 7.23.

EXAMPLE 37

[2-(4-Bromo-2-fluoro-benzylcarbamoyl)-5-methanesulfonyl-phenoxy]-acetic Acid

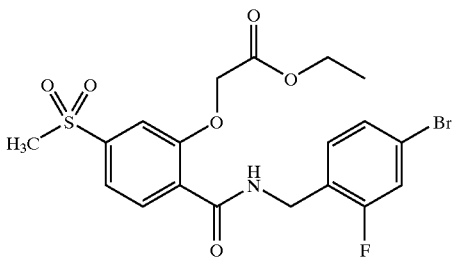

Step 1: [2-(4-Bromo-2-fluoro-benzylcarbamoyl)-5-methanesulfonyl-phenoxy]-acetic Acid Ethyl Ester To a stirring solution of [2-(4-bromo-2-fluoro-benzylcarbamoyl)-5-methylsulfanyl-phenoxyl-acetic acid ethyl ester (Example 24, 2.0 g, 4.38 mmol) in glacial acetic acid (44 mL, 0.1 M) at 55° C. was added sodium perborate (NaBO$_3$.4 H$_2$O, 16.9 g, 109.6 mmol) and the reaction was allowed to stir overnight. The reaction mixture was then cooled to room temperature and diluted with 50 mL of ethyl acetate. The organic layer was washed with water (3×50 mL) and with saturated aq NaCl (50 mL). The organic layer was dried over Na$_2$SO$_4$, filtered, and concentrated under reduced pressure. The resulting oil was purified via a plug of silica gel (5% methanol in dichloromethane). The filtrate was concentrated to afford [2-(4-bromo-2-fluoro-benzylcarbamoyl)-5-methanesulfonyl-phenoxy]-acetic acid ethyl ester as a white solid (1.56 g, 73%): mp 140–143° C.; $R_f$ 0.11 (40% ethyl acetate in heptane); $^1$H NMR (DMSO-$d_6$, 300 MHz) δ 9.01 (t, J=6.2 Hz, 1H), 7.92 (d, J=8.7 Hz, 1H), 7.61–7.58 (m, 2H), 7.52 (d, J=10.8 Hz, 1H), 7.39–7.37 (m, 2H), 5.02 (s, 2H), 4.49 (d, J=5.7 Hz, 2H), 4.18 (q, J=7.1 Hz, 2H), 3.24 (s, 3H), 1.19 (t, J=7.1 Hz, 3H); Anal. calcd for $C_{19}H_{19}BrFNO_6S$: C, 46.73; H, 3.92; Br, 16.36; N, 2.87; S, 6.57. Found C, 46.85; H, 3.89; Br, 16.48; N, 2.98; S, 6.48.

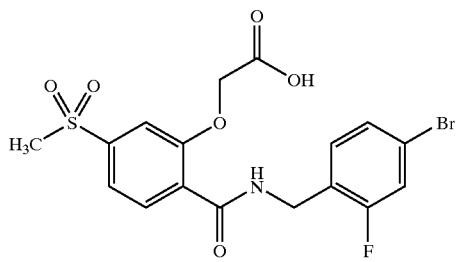

Step 2: [2-(4-Bromo-2-fluoro-benzylcarbamoyl)-5-methanesulfonyl-phenoxy]-acetic Acid

[2-(4-Bromo-2-fluoro-benzylcarbamoyl)-5-methanesulfonyl-phenoxy]-acetic acid was prepared in a fashion analogous to the method set forth in Example 1, step 3 except [2-(4-bromo-2-fluoro-benzylcarbamoyl)-5-methanesulfonyl-phenoxy]-acetic acid ethyl ester was used in place of [2-(4-bromo-2-fluoro-benzylcarbamoyl)-5-chloro-phenoxy]-acetic acid ethyl ester to provide [2-(4-bromo-2-fluoro-benzylcarbamoyl)-5-methanesulfonyl-phenoxy]-acetic acid as a white solid: mp 193–194° C.; $R_f$ 0.19 (20% methanol in methylene chloride); $^1$H NMR (DMSO-$d_6$, 300 MHz) δ 9.13 (t, J=6.0 Hz, 1H), 7.94 (d, J=8.1 Hz, 1H), 7.61–7.58 (m, 2H), 7.51 (d, J=10.8 Hz, 1H), 7.40 –7.38 (m, 2H), 4.99 (s, 2H), 4.49 (d, J=6.0 Hz, 2H), 3.24 (s, 3H); ESI-LC/MS m/z calcd for $C_{17}H_{11}BrFNO_6S$: 458.98; Found 460.0 (M+1)$^+$; Anal. calcd for $C_{17}H_{15}BrFNO_6S.0.5$ H$_2$O: c, 43.51; H, 3.44; N, 2.98; S, 6.83. Found C, 43.43; H, 3.34; N, 2.90; S, 6.59.

EXAMPLE 38

[4-Amino-2-(4-bromo-2-fluoro-benzylcarbamoyl)-phenoxy]-acetic Acid

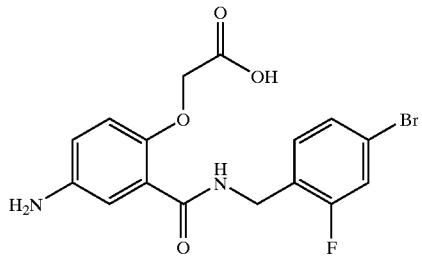

[2-(4-Bromo-2-fluoro-benzylcarbamoyl)-4-nitro-phenoxy]-acetic acid (1.10 g, 2.76 mmol) was dissolved in ethyl alcohol (40 mL, 0.1 M), treated with 10% Pd on carbon (Degussa, 0.10 g) and placed under a balloon of hydrogen for 12 h. The reaction was filtered through Celite and concentrated to give a crude solid which was recrystallized from heptane and ethyl acetate to give [4-amino-2-(4-bromo-2-fluoro-benzylcarbamoyl)-phenoxy]-acetic acid (0.79 g, 66%): mp 204° C (dec.); $R_f$ 0.10 (10% methanol in dichloromethane); $^1$H NMR (DMSO-$d_6$, 300 MHz) δ 9.16 (br t, J=6.3 Hz, 1H), 7.85 (d, J=2.7 Hz, 1H), 7.46–7.11 (m, 5H), 4.91 (s, 2H), 4.57 (br d, J=3.6 Hz, 2H). ESI-LC/MS m/z calcd for $C_{16}H_{14}BrFN_2O_4$: 396.0 found 395.0 (M−1)$^-$. Anal. calcd for $C_{16}H_{14}BrFN_2O_4$: C, 48.38; H, 3.55; N, 7.05. Found C, 48.05; H, 4.02; N, 6.94.

EXAMPLE 39

[2-(4-Bromo-2-fluoro-benzylcarbamoyl)-4-methoxy-phenoxy]-acetic Acid

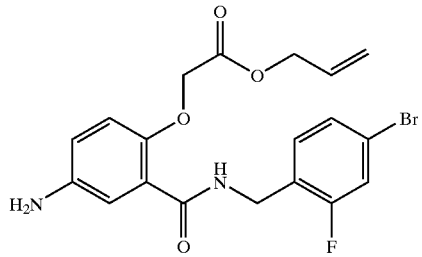

Step 1: [4-Amino-2-(4-bromo-2-fluoro-benzylcarbamoyl)-phenoxy]-acetic Acid Allyl Ester:

[4-Amino-2-(4-bromo-2-fluoro-benzylcarbamoyl)-phenoxy] acetic acid (0.62g, 1.56 mmol) was dissolved in allyl alcohol (15 mL, 0.1 M). This solution was treated with 7 drops of concentrated $H_2SO_4$ and stirred at room temperature for 48 h. The reaction was concentrated, redissolved in ethyl acetate, washed with $H_2SO$, saturated aq NaCl (3×), dried over $Na_2SO_4$ and filtered. The filtrate was treated with decolorizing charcoal, boiled for 10 minutes, cooled to room temperature, filtered and concentrated. The crude solid was recrystallized from heptane and ethyl acetate to give [4-amino-2-(4-bromo-2-fluoro-benzylcarbamoyl)-phenoxy]-acetic acid allyl ester as a light orange solid (0.13 g, 20%). $^1$H NMR (DMSO-$d_6$, 300 MHz) δ 8.92 (br t, J=5.4 Hz, 1H), 7.49–7.80 (m, 4H); 6.84 (d, J=8.7 Hz, 1 H), 6.63 (br dd, $J_1$=8.7 Hz, $J_2$=2.7 Hz, 1H), 5.95–5.79 (m, 1H), 5.29 (br d, J=17.1 Hz, 1H), 5.19 (br d, J=10.5 Hz, 1 H), 4.91 (br s, 1H), 4.83 (br s, 2H), 4.61 (br d, J=5.4 Hz, 1 H).

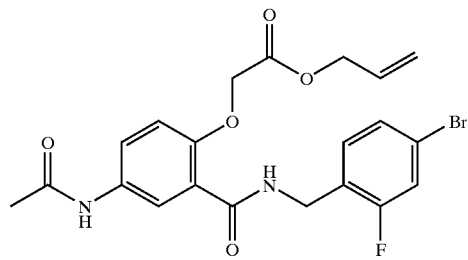

Step 2: [4-Acetylamino-2-(4-bromo-2-fluoro-benzylcarbamoyl)-phenoxy]-acetic acid allyl ester A solution of [4-amino-2-(4-bromo-2-fluoro-benzylcarbamoyl)-phenoxy]-acetic acid allyl ester (0.13 g, 0.30 mmol) was dissolved in tetrahydrofuran (2 mL, 0.2 M) along with pyridine (0.05 mL, 0.05 g, 0.61 mmol). This mixture was cooled to 0° C. before treatment with acetic anhydride (0.10 mL, 0.098 g, 0.95 mmol). After stirring at room temperature for 24 h, the reaction mixture was diluted ethyl acetate and sucessively washed with 2 N HCl, saturated aq $NaHCO_3$ and saturated aq NaCl. The organic layer was dried over $Na_2SO_4$, filtered and concentrated to give [4-acetylamino-2-(4-bromo-2-fluoro-benzylcarbamoyl)-phenoxy]-acetic acid allyl ester (0.125 g, 87%): $^1$H NMR (DMSO-$d_6$, 300 MHz) δ 9.95 (br s, 1H), 8.94 (br t, J=5.7 Hz, 1H), 7.98 (d, J=2.7 Hz, 1H), 7.74 (dd, $J_1$=9.0 Hz, $J_2$=3.0 Hz, 1H), 7.42–7.24 (m, 2H), 7.22–7.02 (m, 2H), 5.88 (m, 1H), 5.30 (dd, $J_1$=17.1 Hz, $J_2$=1.8 Hz, 1H), 5.21 (dd, $J_1$=9.0 Hz, $J_2$=1.8 hz, 1H), 4.97 (s, 2H), 4.64 (br d, J=5.4 Hz, 2H), 4.55 (br d, J=6.0 Hz, 2H), 2.00 (s, 3H).

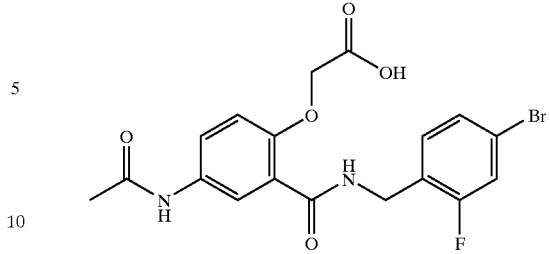

Step 3: [4-Acetylamino-2-(4-bromo-2-fluoro-benzylcarbamoyl)-phenoxy]-acetic Acid A solution of [4-acetylamino-2-(4-bromo-2-fluoro-benzylcarbamoyl)-phenoxy]-acetic acid allyl ester (0.114 g, 0.24 mmol) in 10% $H_2O$ in 1,4-dioxane (8 mL, 0.03 M) was treated with pyrollidine (0.05 mL, 0.60 mmol) and [$(C_6H_5)_3$P]$_4$Pd (0.01 g, 3.6 mol%) was stirred for 6 h. The reaction was diluted with ethyl acetate and washed with 2 N HCl (3×), $H_2O$ (2×), saturated aq NaCl, dried over $MgSO_4$, filtered, concentrated and recrystallized from heptane and ethyl acetate to give [4-acetylamino-2-(4-bromo-2-fluoro-benzylcarbamoyl)-phenoxy]-acetic acid (0.055 g, 52%) as a white solid: mp 235° C.; $^1$H NMR (DMSO-$d_6$, 300 MHz) δ 9.93 (br s, 1H), 9.16 (br t, 1H), 7.98 (br d, J=2.7 Hz, 1H), 7.73 (br dd, $J_1$=9.0 Hz, $J_2$=2.7 Hz, 1 H), 7.44–7.20 (m, 2H), 7.20–7.00 (m, 2H), 4.80 (s, 2H), 4.54 br d, J=4.5 Hz, 2H), 1.99 (s, 3H).

EXAMPLE 40

[2-(4-Bromo-2-fluoro-benzylcarbamoyl)-5-trifluoromethyl-phenoxy]-acetic Acid

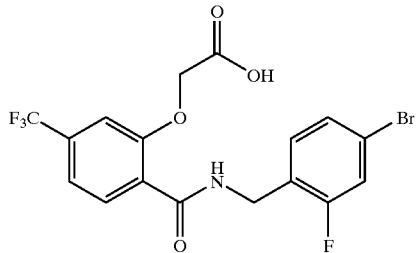

[2-(4-Bromo-2-fluoro-benzylcarbamoyl)-4-trifluoromethyl-phenoxy]-acetic acid was prepared in a manner analogous to that set forth in Example 31, except 2-fluoro-4-(trifluoromethyl)-benzoic acid was used in place of 2,4,6-trifluorobenzoic acid in step 1: mp 169–170° C.; $^1$H NMR (DMSO-$d_6$, 300 MHz) δ 9.12 (br t, J=6.5 Hz, 1H), 7.94 (d, J=7.5 Hz, 1H), 7.54–7.34 (m, 5 H), 4.98 (s, 2H), 4.49 (d, J=5.7 Hz, 2H); Anal. calcd for $C_{17}H_{12}BrF_4NO_4$: C, 45.36; H, 2.69; N, 3.11. Found C, 45.55; H, 2.76; N, 3.12.

EXAMPLE 41

[4-Allyloxy-2-(4-bromo-2-fluoro-benzylcarbamoyl)-phenoxy]-acetic Acid

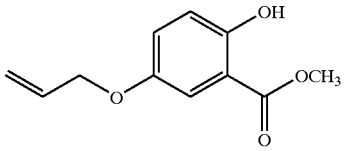

Step 1: 5-Allyloxy-2-hydroxy-benzoic Acid Methyl Ester:

Methyl 2,4-dihydroxybenzoate (8.60 g, 51.2 mmol) was dissolved in acetone (125 mL, 0.4 M) then treated with $K_2CO_3$ (27.2 g, 196.8 mmol) and allyl bromide (6.0 mL, 8.39 g, 69.3 mmol). The reaction was heated at 60° C. for 20 h then acidified to pH 1–2 with 2 N HCl and extracted with $Et_2O$ (4×). The combined extracts were washed with saturated aq NaCl (2×), dried over $Na_2SO_4$, filtered and concentrated to give 5-allyloxy-2-hydroxy-benzoic acid methyl ester as a crude yellow oil (6.11 g, 57%): $^1$H NMR (DMSO-$d_6$, 300 MHz) δ 10.74 (s, 1H), 7.69 (d, J=8.4 Hz, 1H), 6.55–6.51 (m, 2H), 6.08–5.94 (m, 1H), 5.38 (dd, $J_1$=1.8 Hz, $J_2$=16.8 Hz, 2H), 4.61 (d, J=5.4 Hz, 2H), 3.81 (s, 3H).

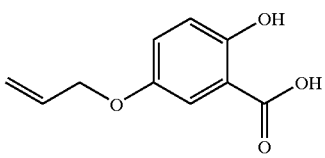

Step 2: 2-Hydroxy-5-propoxy-benzoic Acid:

5-allyloxy-2-hydroxy-benzoic acid methyl ester (6.10 g, 29.30 mmol) was dissolved in methanol (25.0 mL, 1.2 M). This solution was treated with aq NaOH (75 mL, 1.33 M, 100 mmol) and stirred at room temperature for 48 h. The reaction is acidified to pH 1–2 with conc. HCl and extracted with ethyl acetate (4×). The combined organic extracts are washed with $H_2O$ (2×), aq saturated NaCl, dried with $Na_2SO_4$, filtered and concentrated to give 2-hydroxy-5-propoxy-benzoic acid (5.30 g, 91%) as a pale yellow solid: Anal. calcd for $C_{10}H_{10}O_4$: C, 61.85; H, 5.19. Found: C, 62.06; H, 5.27.

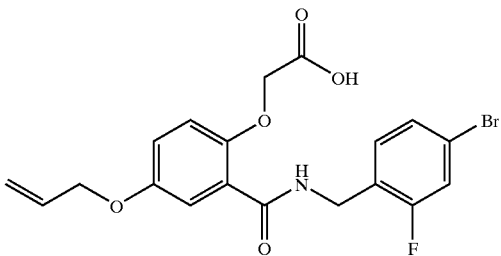

Step 3: [4-Allyloxy-2-(4-bromo-2-fluoro-benzylcarbamoyl)-phenoxy]-acetic Acid

[4-Allyloxy-2-(4-bromo-2-fluoro-benzylcarbamoyl)-phenoxy]-acetic acid was prepared in a manner analogous to that set forth in Example 1, except 5-allyloxy-2-hydroxy-benzoic acid was used in place of the 4-chlorosalicyclic acid. $^1$H NMR (DMSO-$d_6$, 300 MHz) δ 13.33 (br s, 1H), 9.03 (t, J=5.7 Hz, 1H), 7.83 (d, J=9.0 Hz, 1H), 7.48 (d, J=9.6 Hz, 1H), 7.38–7.28 (m, 2H), 6.70–6.65 (m, 2H), 6.10–5.94 (m, 1H), 5.39 (d, J=17.1 Hz, 1H), 5.25 (d, J=10.5 Hz, 1H), 4.85 (s, 2H), 4.61 (dd, $J_1$=1.5 Hz, $J_2$=5.4 Hz, 2H), 4.48 (d, J=6.0 Hz, 2H). ESI-LC/MS m/z calcd for $C_{19}H_{17}BrFNO_5$: 437.0; found 438.0 (M+1)$^+$. Anal. calcd for $C_{19}H_{17}BrFNO_5$: C, 52.07; H, 3.91; N, 3.20. Found: C, 52.12; H, 3.95; N, 3.19.

EXAMPLE 42

[2-(4-Bromo-2-fluoro-benzylcarbamoyl)-4-hydroxy-phenoxy]-acetic Acid

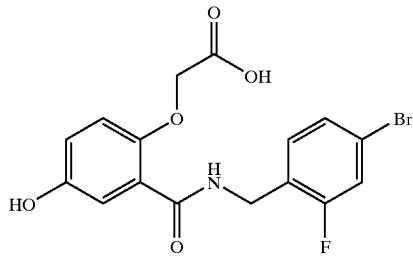

A solution of [4-allyloxy-2-(4-bromo-2-fluoro-benzylcarbamoyl)-phenoxy]-acetic acid ethyl ester (1.02 g, 2.40 mmol) and Pd(Ph3)4 (15 mg, 1.4 mol %) in a aq 1,4-dioxane solution (10 mL, 95% 1,4-dioxane) was treated with pyrrolidine (0.45 mL, 5.39 mmol) in a dropwise manner. After stirring for 2 h at room temperature, the solution was diluted with ethyl acetate and washed with aq 10% HCl, sat's aq NaCl, dried over Na2SO4, filtered and concentrated. The resulting crude solid was recrystallized with ethyl acetate and heptane to give [4-hydroxy-2-(4-bromo-2-fluoro-benzylcarbamoyl)-phenoxy]-acetic acid ethyl ester (0.780 g, 76%) as a white crystalline solid.

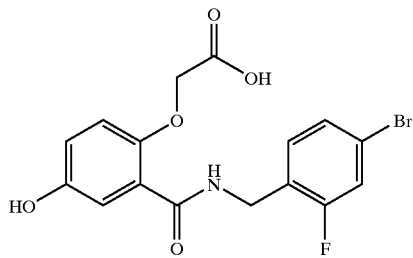

Step 2: [4-hydroxy-2-(4-bromo-2-fluoro-benzylcarbamoyl)-phenoxy-acetic Acid

A solution of [4-hydroxy-2-(4-bromo-2-fluoro-benzylcarbamoyl)-phenoxy]-acetic acid ethyl ester (0.773 g, 1.83 mmol) in ethanol (10 mL, 0.18 M) was cooled to 0° C. and treated with aq KOH (5 mL, 1.25 M) and warmed to room temperature. The solution was acidified to pH 1–2, diluted with ethyl acetate and washed with sat'd aq NaCL. The organic layer was dried over $Na_2SO_4$, filtered and concentrated to give [4-hydroxy-2-(4-bromo-2-fluoro-benzylcarbamoyl)-phenoxy]-acetic acid as a white crystalline solid: mp 244 dec; $^1$H NMR (DMSO-$d_6$, 300 MHz) δ 10.14 (br s, 1H), 8.97 (t, J=5.4 Hz, 1H), 7.75 (dd, $J_1$=8.4 Hz, $J_2$=0.3 Hz, 1H), 7.48 (d, J=9.6 Hz, 1H), 7.37–7.26 (m, 2H), 6.46 (dd, $J_1$=8.7 Hz, $J_2$=2.1 Hz, 1H), 6.40 (s, 1H), 4.77 (s, 2H), 4.47 (d, J=5.4 Hz, 2 Hz). Anal. calcd for $C_{16}H_{13}BrFNO_5$: C, 48.26; H, 3.29; N, 3.52. Found C, 48.19; H, 3.52; N, 3.32.

EXAMPLE 43

[2-(4-Bromo-2-fluoro-benzylcarbamoyl)-4-propoxy-phenoxy]-acetic Acid

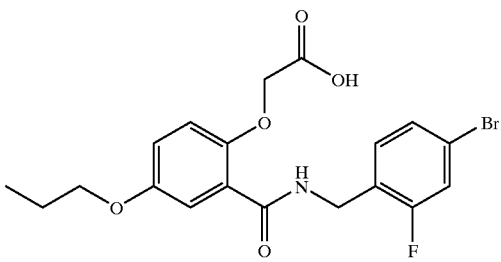

[2-(4-Bromo-2-fluoro-benzylcarbamoyl)-4-propoxy-phenoxy]-acetic acid was prepared in a manner analogous to that set forth in Example 1, except 2-hydroxy-5-propoxy-benzoic acid was used in place of the 4-chlorosalicyclic acid in step 1: $^1$H NMR (DMSO-$d_6$, 300 MHz) δ. ESI-LC/MS m/z calcd for $C_{19}H_{19}BrFNO_5$: 439.0; found 440.0 (M+1)$^+$.

EXAMPLE 44

[2-(2-Fluoro-benzylcarbamoyl)-4-propoxy-phenoxy]-acetic Acid

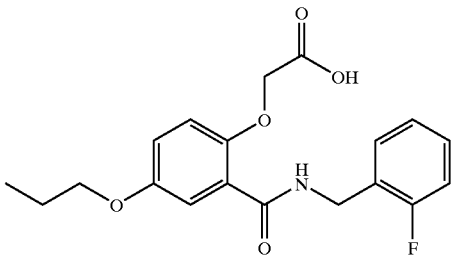

Step 1: [4-Propyloxy-2-(2-fluoro-benzylcarbamoyl)-phenoxy]-acetic Acid Ethyl Ester A solution of [4-allyloxy-2-(4-bromo-2-fluoro-benzylcarbamoyl)-phenoxy]-acetic acid ethyl ester (0.998 g, 2.35 mmol) in ethanol (150 mL) and ethyl acetate (5 mL) was degassed and put under a nitrogen atmosphere. Palladium catalyst (10% Pd-c, Degussa) was added and the flask was evacuated and treated with hydrogen (balloon). After stirring overnight, the solution was filtered through a pad of silica gel and washed with methanol. After concentrating the solution, the crude product was purified by flash collumn chromatography (30% hepatane in ethyl acetate) to give [4-propyloxy-2-(2-fluoro-benzylcarbamoyl)-phenoxy]-acetic acid ethyl ester.

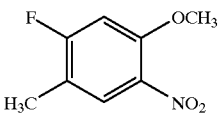

Step 2: [4-Propyloxy-2-(2-fluoro-benzylcarbamoyl)-phenoxy]-acetic Acid

A solution of [4-propyloxy-2-(fluoro-benzylcarbamoyl)-phenoxy]-acetic acid ethyl ester in ethanol (20 mL) was cooled to 0° C. and treated with aq KOH (7.5 mL, 1.25 M) and warmed to room temperature. The solution was acidified to pH 1–2, diluted with ethyl acetate and washed with sat'd aq NaCL. The organic layer was dried over $Na_2SO_4$, filtered and concentrated to give [4-hydroxy-2-(4-bromo-2-fluoro-benzylcarbamoyl)-phenoxy]-acetic acid as a white crystalline solid: $^1$H NMR (DMSO-$d_6$, 300 MHz) δ 13.34 (br s, 1H), 9.03 (s, 1H), 7.85 (dd, $J_1$=9 Hz, $J_2$=2.1 Hz, 1H), 7.40–7.12 (m, 4H), 6.62 (s, 2H), 4.84 (s, 2H), 4.54 (s, 2H), 3.96 (t, J=6.3 Hz, 2H), 1.78–1.63 (m, 2H), 0.98–0.91 (m, 3H).

EXAMPLE 45

[2-(4-Bromo-2-fluoro-benzylcarbamoyl)-5-fluoro-4-methyl-phenoxy]-acetic Acid

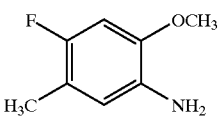

Step 1: 1-Fluoro-5-methoxy-2-methyl-4-nitro-benzene:

Under nitrogen in a nalgene bottle, a stirring solution of pyridine (17.1 mL, 3.2 M, −70° C.) was treated dropwise with HF-pyridine (51.91 mL). Next, 5-methoxy-2-methyl-4-nitro-phenylamine (10.0 g, 54.9 mmol) was added followed by sodium nitrite (6.4 g, 92.76 mmol). The dry ice/acetone bath was removed and the reaction was allowed to warm to room temperature. The solution was then heated at 60° C. for 2 h (or until nitrogen evolution stops.) After cooling to room temperature, the nalgene bottle was placed in an ice bath and 375 mL of water was slowly added to the solution. The resulting orange precipitate was collected by suction filtration and washed with 250 mL of water. Purification of the solid via silica gel flash chromatography (30% ethyl acetate in heptane) provided 1-fluoro-5-methoxy-2-methyl-4-nitro-benzene (7.69 g, 76%) as a light orange solid: mp 71–74°C. $R_f$ 0.56 (30% ethyl acetate in heptane); $^1$H NMR (CDCl$_3$, 300 MHz) δ 7.82 (d, J=7.5 Hz, 1H), 6.75 (d, J=10.5 Hz, 1H), 3.93 (s, 3H), 2.25 (d, J=2.1 Hz, 3H); ESI-LC/MS m/z calcd for $C_8H_8FNO_3$: 185.1; Found 186.0 (M+1)$^+$. Anal. calcd for $C_8H_8FNO_3$: C, 51.90; H, 4.36. Found C, 52.11; H, 4.47.

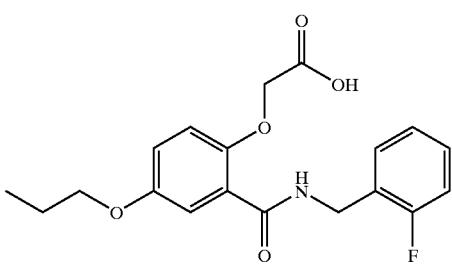

Step 2: 4-Fluoro-2-methoxy-5-methyl-phenylamine:

A solution of 1-fluoro-5-methoxy-2-methyl-4-nitro-benzene (5.5 g, 29.3 mmol) and 10% Pd-C (1.56 g) in ethanol (300 mL, 0.1 M) was hydrogenated at 1 atm. After stirring overnight, the solution was flushed through a pad of silica gel using 400 mL of ethanol as the eluant. The filtrate was concentrated under reduced pressure to afford 4-fluoro-2-methoxy-5-methyl-phenylamine (4.5 g, 99%) as a pale purple solid: mp 108–110° C.; $R_f$ 0.35 (30% ethyl acetate in heptane); $^1$H NMR (DMSO-$d_6$, 300 MHz) δ 6.62 (d, J=11.4 Hz, 1H)', 6.43 (d, J=7.8 Hz, 1H), 3.70 (s, 3H), 2.02 (d, J=1.8 Hz, 3H); ESI-LC/MS m/z calcd for $C_8H_{10}FNO$: 155.1;

Found 156.0 (M+1)⁺. Anal. calcd for $C_8H_{10}FNO$: C, 61.92; H, 6.50. Found: C, 61.64; H, 6.53.

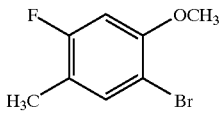

Step 3: 1-Bromo-4-fluoro-2-methoxy-5-methyl-benzene:

A suspension of 4-fluoro-2-methoxy-5-methyl-phenylamine (25.75 g, 0.17 mol) in 180 mL of HBr (48%, 0.9 M) in an ice bath was treated dropwise with an aq solution of sodium nitrite (12.6 g, 0.18 mol, 3.6 M). A brown gas was evolved and the temperature of the reaction was monitored so that the internal temperature did not raise above 10° C. In the meantime, a suspension of CuBr (13.1 g, 0.09 mol) in 6.5 mL of HBr (48%, 13.9 M) was heated to 110° C. Next, the solution at 0° C. was slowly poured (over a period of 20 minutes) into the stirring CuBr suspension. The combined reaction mixture was heated for 2.5 h at 110° C. After cooling to room temperature, the solution was diluted with ethyl acetate and treated with aq sulfuric acid ( 50% v/v). The organic layer was separated and was washed successively with water, sulfuric acid, water, 1.25 M NaOH, water, and saturated aq NaCl. The organic layer was dried over $Na_2SO_4$, filtered, and concentrated under reduced pressure. The resulting brown oil was purified via silica gel flash chromatography (5% ethyl acetate in heptane) to afford 1-bromo-4-fluoro-2-methoxy-5-methyl-benzene (17.1 g, 47%) as a clear liquid: $R_f$ 0.70 (30% ethyl acetate in heptane); ¹H NMR (CDCl₃, 300 MHz) δ 7.34 (d, J=8.4 Hz, 1H), 6.61 (d, J=10.8 Hz, 1H), 3.85 (s, 3H), 2.18 (d, J=1.8 Hz, 3H); Anal. calcd for $C_8H_8BrFO$: C, 43.86. ; H, 3.68; Br, 36.48. Found C, 44.01; H, 3.68; Br, 36.57.

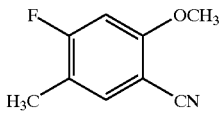

Step 4: 4-Fluoro-2-methoxy-5-methyl-benzonitrile:

A solution of 1-bromo-4-fluoro-2-methoxy-5-methyl-benzene (5.0 g, 22.8 mmol) in DMF (100 mL, 0.2 M) was treated with CuCN (4.7 g, 52.5 mmol). Equipped with a reflux condenser, the reaction was heated to 160° C. for 20 h. After cooling to room temperature, the solution was poured into a 2 L Erlenmeyer flask. Ethyl acetate (400 mL), saturated aq LiCl (100 mL), 1N HCl (100 mL), 11 g of iron (III) chloride hexahydrate, and 15 mL of concd HCl was added to the solution. This green mixture was heated at 70° C. for 2 h (or until emulsion dissipated). After cooling to room temperature, the mixture was poured into a separatory funnel and extracted with ethyl acetate (600 mL total). The combined organics were washed with 1N HCl (200 mL)), saturated aq LiCl (2×200 mL)), and saturated aq NaCl (100 mL). The organic layer was dried over $Na_2SO_4$, filtered, and concentrated under reduced pressure. The resulting powder was dissolved in ethyl acetate (50 mL) and washed with saturated aq LiCl (3×30 mL), dried over $Na_2SO_4$, filtered, and concentrated under reduced to afford 4-fluoro-2-methoxy-5-methyl-benzonitrile (3.25 g, 86%) as a beige powder: mp 99–101° C.; R, 0.53 (30% ethyl acetate in heptane); ¹H NMR (CDCl₃, 300 MHz) δ 7.39 (d, J=8.1 Hz, 1H), 6.65 (d, J=11.1 Hz, 1H), 3.89 (d, J=0.9 Hz, 3H), 2.21 (s, 3H); Anal. calcd for $C_9H_8FNO$: C, 65.45; H, 4.88. Found C, 65.17; H. 4.97.

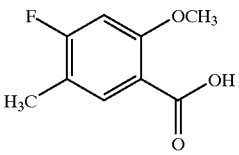

Step 5: 4-Fluoro-2-methoxy-5-methyl-benzoic Acid

A suspension of 4-fluoro-2-methoxy-5-methyl-benzonitrile (3.0 g, 18.2 mmol) in 2N NaOH (300 mL, 0.06 M)) was heated to 90° C. for 19 h. The precipitate was then filtered to recover 0.86 g of 4-fluoro-2-methoxy-5-methyl-benzonitrile. The aqueous layer was acidified to pH 1 using concentrated HCl. The cloudy aqueous layer was extracted with ethyl acetate (2×250 mL). The combined organics were dried over $Na_2SO_4$, filtered, and concentrated to afford 4-fluoro-2-methoxy-5-methyl-benzoic acid a white powder (2.28 g, 96% based on recovered starting material): mp 125–127° C.; $R_f$ 0.15 (40% ethyl acetate in heptane); ¹H NMR (CDCl₃, 300 MHz) δ 10.20 (s, 1H), 8.05 (d, J=9.0 Hz, 1H), 6.74 (d, J=10.8 Hz, 1H), 4.04'(s, 3H), 2.25 (d, J=1.8 Hz, 3H); ESI-LC/MS m/z calcd for $C_9H_9FO_3$: 184.1. Found 185.0 (M+1)⁺. Anal. calcd for $C_9H_9FO_3$: C, 58.70; H, 4.93. Found C, 58.58; H, 4.97.

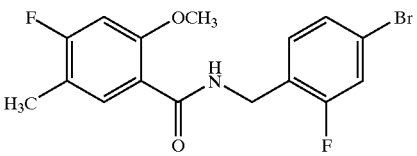

Step 6: N-(4-Bromo-2-fluoro-benzyl)-4-fluoro-2-methoxy-5-methyl-benzamide

Under a dry atmosphere of nitrogen, a solution of 4-fluoro-2-methoxy-5-methyl-benzoic acid (1.19 g, 6.47 mmol) in dichloromethane (16 mL, 0.5 M) was treated with oxalyl chloride (1.7 mL, 19.4 mmol) and a drop of DMF at 0° C. The mixture was allowed to gradually warm to room temperature and was then concentrated to afford a yellow powder. The powder was dissolved in dichloromethane (16 mL, 0.5 M). To the stirring solution at 0° C. was added diisopropylethylamine (2.8 mL, 16.2 mmol) followed by 4-bromo-2-fluorobenzylamine hydrochloride salt (2.34 g, 9.71 mmol). Stirring under nitrogen, the mixture was gradually allowed to warm to room temperature. After 21 hours, the reaction was washed successively with 1N HCl (3×50 mL) and saturated aq NaCl (50 mL). The organic layer was dried over $Na_2SO_4$, filtered, and concentrated to afford N-(4-bromo-2-fluoro-benzyl)-4-fluoro-2-methoxy-5-methyl-benzamide (2.33 g, 97%) as a brown oil which was used without further purification: $R_f$ 0.40 (30% ethyl acetate in heptane); ¹H NMR (CDCl₃, 300 MHz)δ 8.17 (bd s, 1H), 8.06 (d, J=9.3 Hz, 1H), 7.33–7.22 (m, 3H), 6.65 (d, J=11.1 Hz, 1H), 4.63 (d, J=6.3 Hz, 2H), 3.92 (s, 3H), 2.23 (bd d, J=1.8 Hz, 3H).

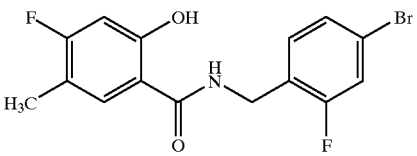

Step 7: N-(4-Bromo-2-fluoro-benzyl)-4-fluoro-2-hydroxy-5-methyl-benzamide

A stirring suspension of N-(4-bromo-2-fluoro-benzyl)4-fluoro-2-methoxy-5-methyl-benzamide (2.32 g, 6.51 mmol) in a 25% solution of HBr in acetic acid (60 mL, 0.11 M) was equipped with a reflux condenser and heated to 120° C. for 3.5 h. The mixture was allowed to cool and saturated aq NaCl (50 mL) and ethyl acetate (50 mL) were added. The layers were allowed to separate and the organic layer was collected. The aqueous layer was extracted with ethyl acetate (2×50 mL). The combined organics were dried over $Na_2SO_4$, filtered, and concentrated to provide an orange powder. Purification of the solid via silica gel flash chromatography (30% ethyl acetate in heptane) provided N-(4-bromo-2-fluoro-benzyl)-4-fluoro-2-hydroxy-5-methyl-benzamide (1.69, 73%) as a white powder: mp 149–150° C.; $R_f$ 0.51 (30% ethyl acetate in heptane); $^1H$ NMR ($CDCl_3$, 300 MHz) δ 12.20 (d, J=1.5, 1H), 7.30–7.29 (m, 2H), 7.26 (s, 1H), 7.14 (d, J=8.1 Hz, 1H), 6.64 (d, J=10.8, 1H), 6.48 (bd s, 1H), 4.62 (d, J=5.7'Hz, 2H), 2.19 (s, 3H); ESI-LC/MS m/z calcd for $C_{15}H_{12}BrF_2NO_2$: 355.0. Found 354.0 (M−1)⁻. Anal. calcd for $C_{15}H_{12}BrF_2NO_2$: C, 50.58; H, 3.40; N, 3.93. Found C, 50.65; H, 3.47; N, 3.87.

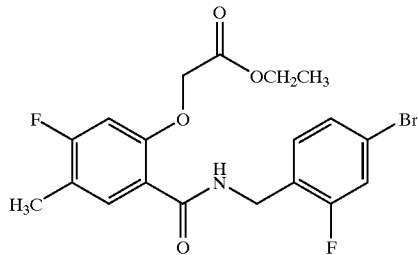

Step 8: [2-(4-Bromo-2-fluoro-benzylcarbamoyl)-5-fluoro-4-methyl-phenoxy]-acetic Acid Ethyl Ester A stirring solution of N-(4-bromo-2-fluoro-benzyl)-4-fluoro-2-hydroxy-5-methyl-benzamide (1.69 g, 4.76 mmol) in acetone (24 mL, 0.2 M) was treated with an aq $K_2CO_3$ solution (3.6 mL, 2 M, 7.12 mmol) and ethylbromoacetate (0.63 mL, 5.69 mmol) in acetone (24 mL, 0.2 M) and heated to 50° C. for 2.5 h. After cooling to room temperature, the solution was concentrated, acidified to pH 1 with 2 N HCl, and diluted with ethyl acetate (100 mL) and washed with 50 mL of saturated aq NaCl. The organic layer was dried over $Na_2SO_4$, filtered, and concentrated to provide [2-(4-bromo-2-fluoro-benzylcarbamoyl)-5-fluoro-4-methyl-phenoxy]-acetic acid ethyl ester (1.95, 93%) as a white solid: mp 128–129° C.; $R_f$ 0.42 (30% ethyl acetate in heptane); $^1H$ NMR ($CDCl_3$, 300 MHz) δ 8.79 (bd t, J=4.5 Hz, 1H), 8.10 (d, J=9.0 Hz, 1H), 7.34 (t, J=8.3 Hz, 1H), 7.26–7.23 (m, 1H), 7.21 (t, J=2.3 Hz, 1H), 6.53 (d, J=10.5 Hz, 1H), 4.66 (d, J=3.9 Hz, 1H), 4.65 (s, 2H), 4.28 (q, J=7.2 Hz, 2H), 2.23 (bd d, J=1.5 Hz, 3H), 1.30 (t, J=7.2 Hz, 3H); Anal. calcd for $C_{19}H_{18}BrF_2NO_4$: C, 51.60; H, 4.10; N, 3.17. Found C, 51.65; H, 4.19; N, 3.10.

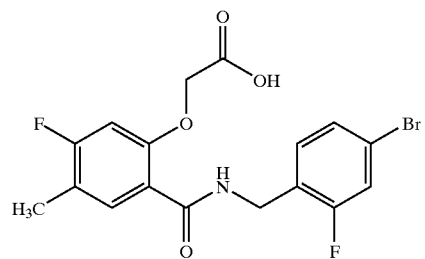

Step 9: [2-(4-Bromo-2-fluoro-benzylcarbamoyl)-5-fluoro-4-methyl-phenoxy]-acetic Acid A stirring solution of (2-(4-bromo-2-fluoro-benzylcarbamoyl)-5-fluoro-4-methyl-phenoxy]-acetic acid ethyl ester (0.72 g, 1.62 mmol) in ethanol (8.1 mL, 0.2 M) was placed in an ice bath and treated with aq NaOH (1.25 M, 7.8 mL, 9.73 mmol). The mixture was gradually allowed to warm to room temperature and after two hours the mixture was concentrated under reduced pressure, diluted with ethyl acetate, and treated with 2 N HCl (10 mL). The separated organic layer was washed with saturated aq NaCl. The organic layer was dried over $Na_2SO_4$, filtered, and concentrated to afford [2-(4-bromo-2-fluoro-benzylcarbamoyl)-5-fluoro-4-methyl-phenoxy]-acetic acid (0.66 g, 98%) as a white solid: mp 169° C.; $R_f$ 0.22 (20% methanol in dichloromethane); $^1H$ NMR (DMSO-$d_6$, 300 MHz) δ 9.00 (bd t, J=5.3 Hz, 1H), 7.76 (d, J 9.6 Hz, 1H), 7.49 (d, J=9.6 Hz, 1H), 7.39–7.33 (m, 2H), 7.04 (dd, $J_1$=11.4 Hz, $J_{2=1.4}$ Hz, 1H), 4.84 (d, J=1.8 Hz, 2H), 4.48 (bd s, 2H), 2.17 (s, 3H); ESI-LC/MS m/z calcd for $C_{17}H_{14}BrF_2NO_4$: 413.0; found 412 (M−1)⁻. Anal. calcd for $C_{17}H_{14}BrF_2NO_4$: C, 49.30; H, 3.41; N, 3.38. Found C, 49.32; H, 3.43; Br, 3.32.

EXAMPLE 46

[2-(4-Bromo-2-fluoro-benzylthiocarbamoyl)-5-fluoro-4-methyl-phenoxy]-acetic Acid

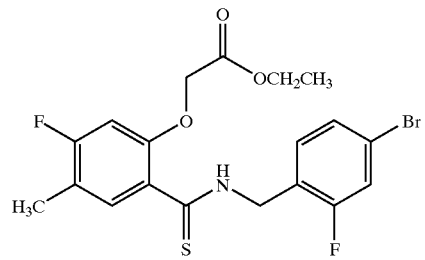

Step 1: [2-(4-Bromo-2-fluoro-benzylthiocarbamoyl)-5-fluoro-4-methyl-phenoxy]-acetic Acid Ethyl Ester A stirring solution of [2-(4-bromo-2-fluoro-benzylcarbamoyl)-5-fluoro-4-methyl-phenoxy]-acetic acid ethyl ester (0.816 g, 1.83 mmol) in pyridine (3.7 mL, 0.5 M) was treated with phosphorus pentasulfide (0.41 g, 0.92 mmol) and heated to 115° C. for 3 h. The reaction was allowed to cool to room temperature, diluted with ethyl acetate and successively washed with 1 M HCl and saturated aq NaCl. The organic layer was dried over $Na_2SO_4$, filtered, and concentrated under reduced pressure. The resulting brown oil was dissolved in a minimal amount of methylene chloride and flushed through a plug of silica using 40% ethyl acetate in heptane as the eluant. The filtrate was concentrated to afford [2-(4-bromo-2-fluorobenzylthiocarbamoyl)-5-fluoro-4-methyl-phenoxy]-acetic acid ethyl ester (0.75 g, 89%) as a yellow solid: mp 98–100° C.; $R_f$ 0.45 (30% ethyl acetate in heptane); $^1$H NMR (CDCl$_3$, 300 mHz) δ 10.15 (bs, 1H), 8.26 (d, J=8.4 Hz, 1H), 7.38 (t, J=8.4 Hz, 1H), 7.26–7.23 (m, 2H), 6.53 (d, J=10.8 Hz, 1H), 5.08 (d, J=5.4 Hz, 2H), 4.67 (s, 3H), 4.20 (q, J=7.2 Hz, 2H), 2.23 (s, 2H), 1.27 (dt, J$_1$=6.8 Hz, J$_2$=0.6 Hz, 3H).

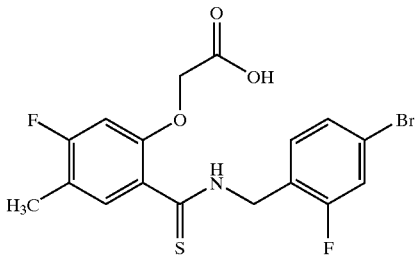

Step 2: [2-(4-Bromo-2-fluoro-benzylthiocarbamoyl)-5-fluoro-4-methyl-phenoxy]-acetic Acid A stirring solution of [2-(4-bromo-2-fluoro-benzylthiocarbamoyl)-5-fluoro-4-methyl-phenoxy]-acetic acid ethyl ester (0.79 g, 1.53 mmol) in ethanol (7.6 mL, 0.2 M) and treated with aqueous NaOH (2 N, 7.4 mL, 9.15 mmol) in an analogous fashion to Example 45, Step 9 to provide [2-(4-bromo-2-fluoro-benzylthiocarbamoyl)-5-fluoro-4-methyl-phenoxy]-acetic acid (0.65 g, 98%) as a yellow solid: mp 162–164° C.; $R_f$ 0.41 (20% methanol in methylene chloride); $^1$H NMR (DMSO-d$_6$, 300 mHz) δ 10.64 (t, J=5.0 Hz, 1H), 7.61 (d, J=9.0 Hz, 1H), 7.52 (dd, J$_1$=9.6 Hz, J$_2$=1.7 Hz, 1H), 7.45–7.36 (m, 2H), 7.00 (d, J=11.4 Hz, 1H), 4.89 (bd d, J=5.1 Hz, 2H), 4.78 (s, 2H), 2.15 (d, J=1.2 Hz, 3H); ESI-LC/MS m/z calcd for C$_{17}$H$_{14}$BrF$_2$NO$_3$S: 428.98; found 428.0 (M−1)$^-$; Anal. calcd for C$_{17}$H$_{14}$BrF$_2$NO$_3$S: C, 47.45; H, 3.28; N, 3.26; S, 7.45. Found C, 47.54; H, 3.19; N, 3.11; S, 7.33.

EXAMPLE 47

[2-(3-Nitro-benzylcarbamoyl)-5-fluoro-4-methyl-phenoxy]-acetic Acid

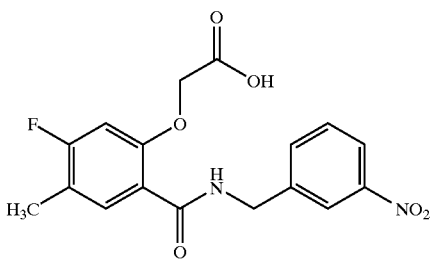

[5-Fluoro-4-methyl-2-(3-nitro-benzylcarbamoyl)-phenoxy]-acetic acid was prepared in a manner analogous to that set forth in Example 45, except 2,3-nitrobenzylamine hydrochloride salt was used in place of 4-bromo-2-fluorobenzylamine hydrochloride salt in Step 6: mp 177–179° C.; $R_f$ 0.28 (20% methanol in dichloromethane); $^1$H NMR (DMSO-d$_6$, 300 MHz) δ 9.14 (t, J=6.2 Hz, 1H), 8.17 (s, 1H), 8.09 (dd, J$_1$=8.4 Hz, J$_2$=1.2 Hz, 1H), 7.79–7.75 (m, 2H), 7.60 (t, 1H), 7.04 (d, J=5.9 Hz, 1H), 4.87 (s, 2H), 4.62 (d, J=4.2 Hz, 2H), 2.17 (s, 3H); ESI-LC/MS m/z calcd for C$_{17}$H$_{15}$FN$_2$O$_6$: 362.1; Found 363.0 (M+1)$^+$. Anal. calcd for C$_{17}$H$_{15}$FN$_2$O$_6$: C, 56.36; H, 7.73; N, 4.17. Found C, 56.45; H, 7.64; N, 4.19.

Example 48

[2-(3-Nitro-benzylthiocarbamoyl)-5-fluoro-4-methyl:-phenoxy]-acetic Acid

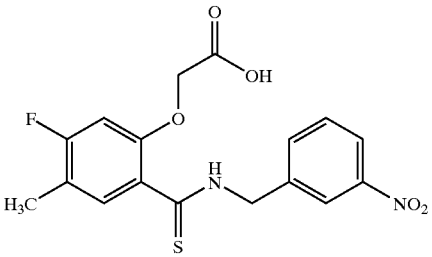

[5-Fluoro-4-methyl-2-(3-nitro-benzylthiocarbamoyl)-phenoxy]-acetic acid was prepared in a manner analogous to that set forth in Example 46, except [5-fluoro-4-methyl-2-(3-nitro-benzylcarbamoyl)-phenoxy]-acetic acid ethyl ester was used in place of [2-(4-bromo-2-fluoro-benzylcarbamoyl)-5-fluoro-4-methyl-phenoxy]-acetic acid ethyl ester in Step 1: mp 137–139° C.; $R_f$ 0.29 (20% methanol in dichloromethane); $^1$H NMR (DMSO-d$_6$, 300 MHz) δ 10.81 (bd s, 1H), 8.23 (s, 1H), 8.12 (dd, J$_1$=7.8 Hz, J$_2$=2.0 Hz, 1H), 8.84 (d, J=7.5 Hz, 1H), 7.65–7.60 (m, 2H), 6.99 (d, J=11.4 Hz, 1H), 5.07 (bd d, J=3.6 Hz, 2H), 4.79 (3, 2H), 2.15 (d, J=1.5 Hz, 3H) ; ESI-LC/MS mi/z calcd for C$_{17}$H$_{15}$FN$_2$O$_5$ S: 378.1; Found 377.0 (M−1)$^-$. Anal. calcd for C$_{17}$H$_{15}$FN$_2$O$_5$ S: C, 53.96; H, 4.00; N, 7.4; S, 8.47. Found C, 53.97; H, 4.02; N, 7.33; S, 8.40.

EXAMPLE 49

[4-Bromo-5-fluoro-2-(3-nitro-benzylcarbamoyl)-phenoxy]-acetic Acid

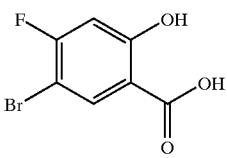

Step 1: 5-Bromo-4-fluoro-2-hydroxy-benzoic Acid

To a stirring solution of 4-fluoro-2-hydroxy-benzoic acid (5.58 g, 35.7 mmol) in dimethyl formamide (72 mL, 0.5 M) was added N-bromosuccinimide (7.08 g, 39.3 mmol). The mixture was allowed to stir for 24 h at room temperature. Next, the mixture was diluted with 300 mL of ethyl acetate and washed successively with water (3 x 330 mL) and saturated aq LiCl (4×200 mL). The organic layer was dried over Na$_2$SO$_4$, filtered and concentrated to afford 5-bromo-4-fluoro-2-hydroxy-benzoic acid (8.1 g, 96%) as a beige powder. Please note, the product may contain up to 20% of a dibrominated impurity which may be separated from the desired product after coupling with a benzylamine or upon methylation (Example 50): $R_f$ 0.32 (20% methanol in dichloromethane); $^1$H NMR (DMSO-d$_6$, 300 mHz) δ 8.00 (d, J=8.1 Hz, 1H), 7.05 (d, J=10.5 Hz, 1H).

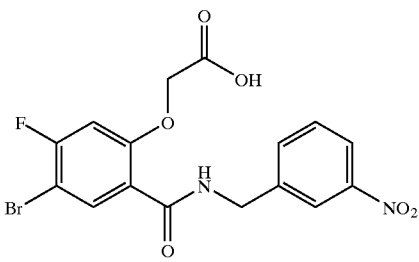

Step 2: [4-Bromo-5-fluoro-2-(3-nitro-benzylcarbamoyl)-phenoxy]-acetic Acid

[4-Bromo-5-fluoro-2-(3-nitro-benzylcarbamoyl)-phenoxy]-acetic acid was prepared in a manner analogous to that set forth in Example 1 except in step 1, 5-bromo-4-fluoro-2-hydroxy-benzoic acid was used in place of 4-chloro-2-hydroxy-benzoic acid and 3-nitrobenzylamine hydrochloride was used in place of 4-bromo-2-fluorobenzylamine hydrochloride: mp 169–172° C.; $R_f$ 0.28 (20% methanol in dichloromethane); $^1$H NMR (DMSO-$d_6$, 300 mHz) δ 9.17 (bt, J=4.5, 1H), 8.19 (s, 1H), 8.11 (d, J=8.1 Hz, 1H), 8.05 (d, J=8.4 Hz, 1H), 7.80 (d, J=7.8 Hz, 1H), 7.62 (t, J=8.1 Hz, 1H), 7.35 (d, J=10.5 Hz, 1H), 4.93 (s, 2H), 4.63 (d, J=5.7 Hz, 2H); ESI-LC/MS m/z calcd for $C_{16}H_{12}BrFN_2O_6$: 426.0. Found 427.0 (M+1)$^+$. Anal. calcd for $C_{16}H_{12}BrFN_2O_6$: C, 44.99; H, 2.83; N, 6.56; Br, 18.71. Found C, 44.87; H, 2.87; N, 6.46; Br, 18.59.

EXAMPLE 50
[5-(3-Nitro-benzylcarbamoyl)-2-fluoro-biphenyl-4-yloxy]-acetic Acid

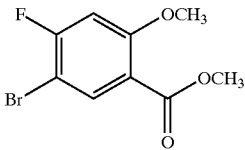

Step 1: 5-Bromo-4-fluoro-2-methoxy-benzoic Acid Methyl Ester

A stirring solution of 5-bromo-4-fluoro-2-hydroxy-benzoic acid (15.0 g, 63.8 mmol) in acetone (128 mL, 0.5 M) was treated with anhydrous $K_2CO_3$ (19.4 g, 140.4 mmol) and iodomethane (24.0 mL, 383.0 mmol). Equipped with a reflux condenser, the mixture was heated overnight at 60° C. Based upon TLC, there was no starting material present so the reaction mixture was cooled to room temperature, concentrated, and purified by MPLC (10–100% ethyl acetate in heptane, 23 mL/min, 70 min) to afford 5-bromo-4-fluoro-2-methoxy-benzoic acid methyl ester (13.52 g, 80%) as a white solid: mp xx ° C.; $R_f$ 0.56 (40% ethyl acetate in heptane); $^1$H NMR (CDCl$_3$, 300 MHz) δ 8.05 (d, J=7.8 Hz, 1H), 6.76 (d, J=10.5 Hz, 1H), 3.89 (s, 3H), 3.88 (s, 3H).

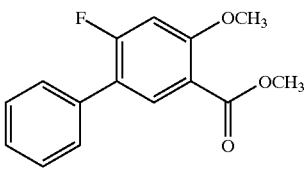

Step 2: 6-Fluoro-4-methoxy-biphenyl-3-carboxylic Acid Methyl Ester

To a flame dried flask containing degassed toluene (15.2 mL, 0.5 M) was added 5-bromo-4-fluoro-2-methoxy-benzoic acid methyl ester (2.0 g, 7.6 mmol), anhydrous $K_2CO_3$ (2.1 g, 15.2 mmol), phenylboronic acid (3.7 g, 30.4 mmol), and Pd(PPh$_3$)$_4$ (0.88 g, 0.76 mmol). Using a reflux condenser, the stirring mixture was heated to 110° C. for 3.5 h. The mixture was then cooled to room temperature, placed in an ice bath and H$_2$O$_2$ (30%, 10 mL) was slowly added. The ice bath was removed and the reaction was allowed to stir at room temperature for one hour. The mixture was then diluted with ether and washed successively with 2 N HCl and saturated aq NaCl. The organic layer was dried over Na$_2$SO$_4$, filtered, and concentrated to afford a brown oil. Purification by MPLC (10–100% ethyl acetate in heptane, 23 mL/min, 75 min) provided 6-fluoro-4-methoxy-biphenyl-3-carboxylic acid methyl ester (1.8 g, 91%) as a pale yellow solid: $R_f$ 0.5 (40% ethyl acetate in heptane); $^1$H NMR (CDCl$_3$, 300 MHz) δ 8.00 (d, J=9.0 Hz, 1H), 7.53–7.33 (m, 5H), 6.79 (d, J=12.6 Hz, 1H), 3.94 (s, 3H), 3.89 (s, 3H).

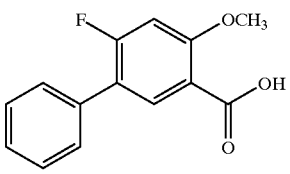

Step 3: 6-Fluoro-4-methoxy-biphenyl-3-carboxylic Acid

To a stirring solution of 6-fluoro-4-methoxy-biphenyl-3-carboxylic acid methyl ester (0.5 g, 2.3 mmol) in dioxane (8 mL, 0.3 M) was added 2N NaOH (6.0 mL, 12 mmol). After one hour at room temperature, the reaction mixture was concentrated, and 2N HCl was added. The aqueous layer was diluted with ether. The organic layer was separated, dried over Na$_2$SO$_4$, filtered and concentrated to afford a 6-fluoro-4-methoxy-biphenyl-3-carboxylic acid (0.55 g, 96%) as a pale yellow powder: $R_f$ 0.18 (5% methanol in dichloromethane); $^1$H NMR (CDCl$_3$, 300 MHz) δ 8.35 (d, J=9.0 Hz, 1H), 7.55–7.52 (m, 2H), 7.48–7.38 (m, 3H), 6.89 (d, J=11.7 Hz, 1H), 4.12 (s, 3H).

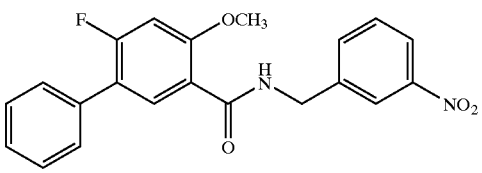

Step 4: 6-Fluoro-4-methoxy-biphenyl-3-carboxylic Acid 3-Nitro-benzylamide

A stirring slurry of 6-fluoro-4-methoxy-biphenyl-3-carboxylic acid (1.0 g, 4.06 mmol) in dichloromethane (8.2 mL, 0.5 M) was treated with oxalyl chloride (1.1 mL, 12.2 mmol) and DMF (1 drop). The mixture was heated to 40° C. until the solution was clear (1–2 h). Next, the mixture was allowed to cool to room temperature, concentrated under reduced pressure, and then diluted with dichloromethane (8.2 mL, 0.5 M). To the stirring mixture at 0° C. was added diisdpropylethyl amine (1.8 mL, 10.2 mmol) followed by 3-nitrobenzylamine hydrochloride salt (1.2 g, 6.1 mmol). Stirring under nitrogen, the solution was gradually warmed to room temperature and stirred overnight. The mixture was then diluted with dichloromethane and washed with 2N HCl (2×50 mL) and saturated aq NaCl (1×100 mL) The organic layer was dried over Na$_2$SO$_4$, filtered, and concentrated to afford a yellow oil. Purification by MPLC (10–100% ethyl acetate in heptane, 23 mL/min, 75 min) provided 6-fluoro- 4-methoxy-biphenyl-3-carboxylic acid 3-nitro-benzylamide (1.0 g, 65%) as a yellow solid: $R_f$ 0.33 (50% ethyl acetate in heptane); $^1$H NMR (DMSO-$d_6$, 300 MHz) δ 8.90 (bd t, J=6.2 Hz, 1H), 8.10 (dd, $J_1$=7.2 Hz, $J_2$=2.4 Hz, 1H), 7.84 (d, J=9.3 Hz, 1H), 7.79 (d, J=7.5 Hz, 1H), 7.63 (t, J=8.0 Hz, 1H), 7.52–7.43 (m, 5H), 7.40–7.34 (m, 1H), 7.20 (d, J=12.9 Hz, 1H), 4.61 (d, J=6.0 Hz, 2H), 3.96 (s, 3H).

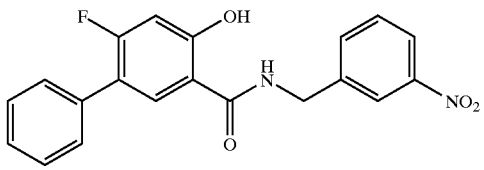

Step 5: 6-Fluoro-4-hydroxy-biphenyl-3-carboxylic Acid 3-Nitro-benzylamide

A stirring solution of 6-fluoro-4-methoxy-biphenyl-3-carboxylic acid 3-nitro-benzylamide (2.18 g, 5.7 mmol) in dichloromethane (150 mL, 0.4 M) at −78° C. was treated with BBr$_3$ (27 mL, 27 mmol). The mixture was allowed to stir for 45 min at −78° C. and was then quenched with 100 mL of methanol. The mixture was allowed to warm to room temperature, concentrated, and filtered through a plug of silica gel using 50% ethyl acetate as the eluant. The filtrate was concentrated to provide 6-fluoro-4-hydroxy-biphenyl-3-carboxylic acid 3-nitro-benzylamide (2.1 g, 100%) as a yellow powder: $R_f$ 0.68 (50% ethyl acetate in heptane); $^1$H NMR (CDCl$_3$, 300 MHz) δ 12.29 (bd s, 1H), 8.14–8.09 (m, 2H), 7.65 (d, J=7.2 Hz, 1H), 7.48 (t, J=8.0 Hz, 1H), 7.38–7.29 (m, 5H), 6.74 (d, J=11.4 Hz, 1H), 6.60 (bd s, 1H), 4.68 (d, J=6.0 Hz, 2H).

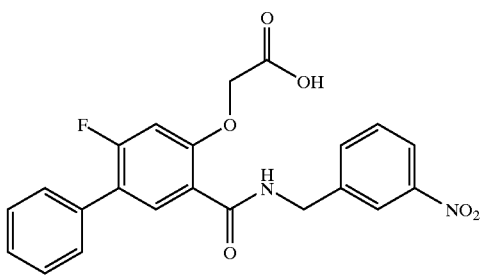

Step 6: [2-Fluoro-5-(3-nitro-benzylcarbamoyl)-biphenyl-4-yloxy]-acetic Acid

[2-Fluoro-5-(3-nitro-benzylcarbamoyl)-biphenyl-4-yloxy]-acetic acid was prepared in an analogous manner as that set forth in Example 45 (steps 8–9) except 6-fluoro-4-hydroxy-biphenyl-3-carboxylic acid 3-nitro-benzylamide was used in place of N-(4-bromo-2-fluoro-benzyl)-4-fluoro-2-hydroxy-5-methyl-benzamide in Step 8: mp 210–211° C.; $R_f$ 0.53 (20% methanol in dichloromethane); $^1$H NMR (DMSO-$d_6$, 300 MHz) δ 9.18 (t, J=5.9 Hz, 1H), 8.20 (s, 1H), 8.11 (dd, $J_1$=8.1 Hz, $J_2$=1.1 Hz, 1H), 7.96 (d, J=9.3 Hz, 1H), 7.81 (d, J=8.1 Hz, 1H), 7.62 (t, J=7.8 Hz, 1H), 7.52–7.35 (m, 5H), 7.22 (d, J=12.3 Hz, 1H), 4.96 (s, 2H), 4.64 (d, J=6.3 Hz, 2H); ESI-LC/MS m/z calcd for $C_{22}H_{17}FN_2O_6$: 424.1; Found 423.0 (M−1)$^-$. Anal. calcd for $C_{22}H_{17}FN_2O_6$: C, 62.26; N, 6.60; H, 4.04. Found C, 62.18; N, 6.47; H, 4.14.

EXAMPLE 51

[5-(3-Nitro-benzylthiocarbamoyl)-2-fluoro-biphenyl-4-yloxy]-acetic Acid

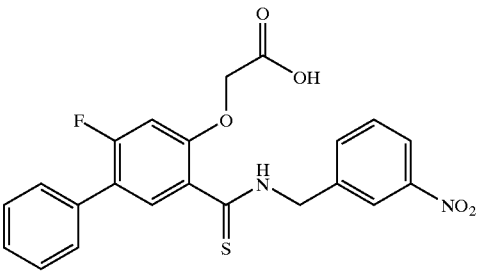

[2-Fluoro-5-(3-nitro-benzylthiocarbamoyl)-biphenyl-4-yloxy]-acetic acid was prepared in an analogous manner to that set forth in Example 46 except that in Step 1, [2-fluoro-5-(3-nitro-benzylcarbamoyl)-biphenyl-4-yloxy]-acetic acid ethyl ester was used in place of [2-(4-bromo-2-fluoro-benzylcarbamoyl)-5-fluoro-4-methyl-phenoxy]-acetic acid ethyl ester: mp 177–179° C.; $R_f$ 0.46 (20% methanol in dichloromethane); $^1$H NMR (DMSO-$d_6$, 300 MHz) δ 10.85 (bd S, 1H), 8.26 (d, J=3.0 Hz, 1H), 8.12 (d, J=8.4 Hz, 1H), 7.86 (d, J=6.6 Hz, 1H), 7.82 (d, J=9.3 Hz, 1H), 7.64 (t, J=8.0 Hz, 1H), 7.51–7.36 (m, 5H), 7.18 (d, J=12.6 Hz, 1H), 5.10 (bd d, J=6.0 Hz, 2H), 4.89 (s, 2H); ESI-LC/MS m/z calcd for $C_{22}H_{17}FN_2O_5S$: 440.1; Found 439.0 (M−1)$^-$. Anal. calcd for $C_{22}H_{17}FN_2O_5S$: C, 59.99; N, 6.36; H, 3.89. Found C, 59.79; N, 6.12; H, 4.11.

EXAMPLE 52

[2-(3-Nitro-benzylcarbamoyl)-4-cyano-5-fluoro-phenoxy]-acetic Acid

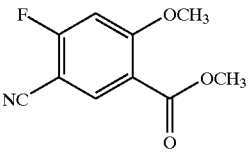

Step 1: 5-Cyano-4-fluoro-2-methoxy-benzoic Acid Methyl Ester

A stirring solution of 5-bromo-4-fluoro-2-methoxy-benzoic acid methyl ester (5.0 g, 10.0 mmol) in DMF (38 mL, 0.5 M) was treated with CuCN (3.92 g, 43.7 mmol). Equipped with a reflux condenser, the mixture was heated at 150° C. for 24 hours. After cooling, the reaction was poured into a 2 L erlenmeyer flask. Ethyl acetate (400 mL), saturated aq LiCl (100 mL), 1N HCl (100 mL)), 11 g of iron (III) chloride hexahydrate, and 15 mL of concd HCl was added to the solution. This green mixture was heated at 70° C. for 2 h (or until emulsion dissapated). After cooling to room temperature, the mixture was poured into a seperatory funnel and extracted with ethyl acetate (600 mL total). The combined organics were washed with 1N HCl (200 mL), saturated aq LiCl (2×200 mL) and saturated aq NaCl (100 mL). The organic layer was dried over Na$_2$SO$_4$, filtered, and concentrated under reduced pressure. Purification by MPLC (10–100% ethyl acetate in heptane, 23 mL/min, 75 min) provided 5-cyano-4-fluoro-2-methoxy-benzoic acid methyl ester (2.98 g, 75%) as a white crystalline solid: $^1$H NMR (CDCl₃, 300 MHz) δ 8.15 (d, J=7.5 Hz, 1H), 6.80 (d, J=11.1 Hz, 1H), 3.97 (s, 3H), 3.90 (s, 3H).

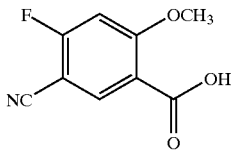

Step 2: 5-Cyano-4-fluoro-2-methoxy-benzoic Acid

A stirring suspension of 5-cyano-4-fluoro-2-methoxy-benzoic acid methyl ester (2.98 g, 14.25 mmol) in ethanol (30 mL, 0.5 M) was treated with 1.25 M NaOH (68 mL, 85.5 mmol). Within 10 minutes, the solution was clear and by TLC, all of the starting material was consumed. The solution was concentrated and then treated with 2N HCl until the pH was 1. The white precipitate formed was collected by suction filtration, dissolved in dioxane, and was washed with aq saturated NaCl. The organic layer was dried over Na₂SO₄, filtered and concentrated to afford 5-cyano-4-fluoro-2-methoxy-benzoic acid (1.9 g, 70%) as a white solid. $R_f$=0.34 (20% methanol in dichloromethane); ¹H NMR (CDCl₃, 300 MHz) δ 8.13 (d, J=8.1 Hz, 1H), 7.36 (d, J=12.0 Hz, 1H), 3.90 (s, 3H).

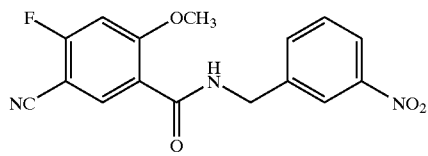

Step 3: [5-Cyano-4-fluoro-2-methoxy-N-(3-nitro-benzyl)-benzamide

To a stirring slurry of 5-cyano-4-fluoro-2-methoxy-benzoic acid (1.92 g, 9.8 mmol) in dichloromethane (20 mL, 0.5 M) was added oxalyl chloride (2.57 mL, 29.5 mmol) and DMF (1 drop). The mixture was heated to 40° C. until the solution was clear (1–2 h). Next, the mixture was allowed to cool to room temperature, concentrated under reduced pressure, and then diluted with dichloromethane (20 mL, 0.5 M). To the stirring mixture at 0° C. was added diisopropylethyl amine (4.3 mL, 24.6 mmol) followed by 3-nitrobenzylamine hydrochloride salt (2.78 g, 14.8 mmol). The stirring under nitrogen, the solution was gradually warmed to room temperature and stirred overnight. The mixture was then diluted with dichloromethane and washed with 2N HCl (3×25 mL) and saturated aq NaCl (2×25 mL). The organic layer was dried over Na₂SO₄, filtered, and concentrated to afford a yellow oil. Purification by MPLC (10–100% ethyl acetate in heptane, 23 mL/min, 75 min) provided [5-cyano-4-fluoro-2-methoxy-N-(3-nitro-benzyl)-benzamide (2.0 g, 63%) as a yellow solid: ¹H NMR (DMSO-d₆, 300 MHz) δ 8.55 (d, J=7.5 Hz, 1H), 8.19 (s, 1H), 8.15 (d, J=8.4 Hz, 1H), 7.96 (bd s, 1H), 7.70 (d, J=6.3 Hz, 1H), 7.54 (t, J=8.0 Hz, 5H), 6.86 (d, J=10.5 Hz, 1H), 4.76 (d, J=5.4 Hz, 1H), 4.07 (d, J=1.2 Hz, 3H).

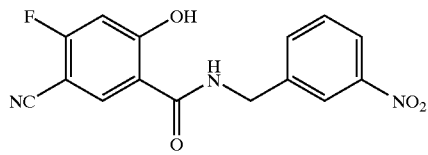

Step 4: 5-Cyano-4-fluoro-2-hydroxy-N-(3-nitro-benzyl)-benzamide

To a stirring solution of [5-cyano-4-fluoro-2-methoxy-N-(3-nitro-benzyl)-benzamide (1.5 g, 4.6 mmol) in dichloromethane (200 mL, 0.3 M) at −78° C. was added BBr₃ (21.5 mL, 21.4 mmol). the mixture was allowed to'stir for 45 min at −78° C. and the dry ice/acetone bath was then removed and the solution was allowed to warm to room temperature. Then, the solution was cooled down again to −78° C. and was then quenched with 100 mL of methanol. The mixture was allowed to warm to room temperature and concentrated. Purification by MPLC (10–100% ethyl acetate, 23 mL/min, 75 min) provided 5-cyano-4-fluoro-2-hydroxy-N-(3-nitro-benzyl)-benzamide (0.85 g, 59%) as a beige powder: $R_f$ 0.37 (70% ethyl acetate in heptane); ¹H NMR (DMSO-d₆, 300 MHz) δ 9.50 (bd s, 1H), 8.39 (d, J=7.5 Hz, 1H), 8.20 (s, 1H), 8.12 (d, J=9.3 Hz, 1H), 7.80 (d, J=7.2 Hz, 1H), 7.63 (t, J=7.8 Hz, 1H), 7.04 (d, J=11.1 Hz, 1H), 4.62 (s, 2H).

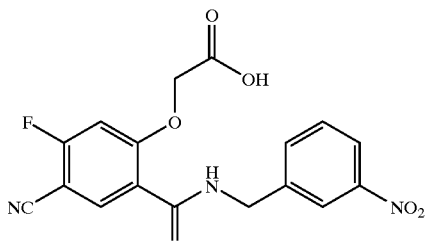

Step 5: [4-Cyano-5-fluoro-2-(3-nitro-benzylcarbamoyl)-phenoxy]-acetic Acid

[4-Cyano-5-fluoro-2-(3-nitro-benzylcarbamoyl)-phenoxy]-acetic acid was prepared in an analogous manner to that set forth in Example 45 (Steps 8–9) except that in Step 8, 5-cyano-4-fluoro-2-hydroxy-N-(3-nitro-benzyl)-benzamide was used in place of N-(4-bromo-2-fluorobenzyl)-4-fluoro-2-hydroxy-5-methyl-benzamide. In Step 9, special care was taken in the hydrolysis of [4-cyano-5-fluoro-2-(3-nitro-benzylcarbamoyl)-phenoxy]-acetic acid ethyl ester. The hydrolysis was performed in dioxane instead of ethanol and quenched after 15 minutes to prevent hydrolysis of the cyano functionality: mp 179–180° C.; $R_f$ 0.22 (20 6 methanol in dichloromethane); ¹H NMR (DMSO-d₆, 300 MHz) δ 9.12 (t, J=6.0 Hz, 1H), 8.21 (d, J=7.8 Hz, 1H), 8.19 (s, 1H), 8.10 (dd, J₁=8.4 Hz, J₂=2.6 Hz, 1H), 7.80 (d, J=8.4 Hz, 1H), 7.61 (t, J=8.0 Hz, 1H), 7.45 (d, J=11.4 Hz, 1H), 4.99 (s, 2H), 4.61 (d, J=6.0 Hz, 2H); ESI-LC/MS m/z calcd for $C_{17}H_{12}FN_3O_6$: 373.1; Found 472.0 (M−1)⁻. Anal. calcd for $C_{17}H_{12}FN_3O_6$: C, 54.70; N, 11.26; H, 3.24. Found C, 54.43; N, 11.07; H, 3.32.

EXAMPLE 53

[2-(3-Nitro-benzylcarbamoyl)-5-fluoro-4-morpholin-4-yl-phenoxy]-acetic Acid

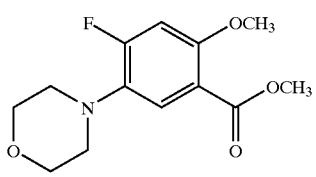

Step 1: 4-Fluoro-2-methoxy-5-morpholin-4-yl-benzoic Acid Methyl Ester

In a flame-dried flask, under a nitrogen atmosphere, oven-dried cesium carbonate (4.33 g, 13.3 mmol) was combined with palladium acetate (85.3 mg, 0.380 mmol) and R-(+)-2,2'-bis(diphenylphosphino)-1,1'-binaphthyl (0.355 g, 0.570 mmol). While under a constant nitrogen flow, the mixture was dissolved in toluene (0.76 mL) and treated with 5-bromo-4-fluoro-2-methoxy-benzoic acid methyl ester (2.50 g, 9.50 mmol) and morpholine (0.995 mL, 11.4 mmol). After being heated to 100° C. for 24 h, the reaction was cooled to room temperature, diluted with ether, filtered and concentrated. Purification by MPLC (ethyl acetate in heptane) provided 4-fluoro-2-methoxy-5-morpholin-4-yl-benzoic acid methyl ester (1.20 g, 47%): $^1$H NMR (DMSO-$d_6$ 300 MHz) δ 7.33 (d, J=9.9 Hz, 1H), 7.08 (d, J=14.4 Hz, 1H), 3.76 (s, 3H), 3.75 (s, 3H), 3.70 (t, J=4.7 Hz, 4H), 2.90 (t, J=4.5 Hz, 4H).

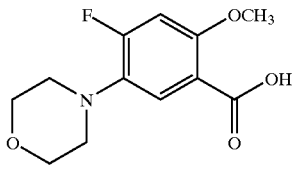

Step 2: 4-Fluoro-2-methoxy-5-morpholin-4-yl-benzoic Acid:

A suspension of 4-fluoro-2-methoxy-5-morpholin-4-yl-benzoic acid methyl ester (1.2.0 g, 4.46 mmol) in ethanol (22.0 mL) was treated with aq 2 N NaOH (13 mL, 26.7 mmol). The mixture was stirred at room temperature for 2 h, concentrated until most of the ethanol was removed and acidified with aq 2 N HCl to pH 1. After extracting with ethyl acetate, the organic layer was washed with saturated aq NaCl, dried over MgSO$_4$ and concentrated to give 4-fluoro-2-methoxy-5-morpholin-4-yl-benzoic acid (0.90 g, 79%): $^1$H NMR (DMSO-$d_6$ 300 MHz) δ 12.62 (s, 1H), 7.34 (d, J=10.5 Hz, 1H), 7.04 (d, J=14.7 Hz, 1H), 3.76 (s, 3H), 3.70 (t, J=4.7 Hz, 4H), 2.90 (t, J=4.7 Hz, 4H).

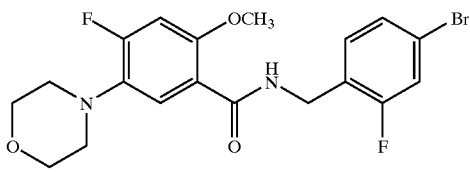

Step 3: N-(4-Bromo-2-fluoro-benzyl)-4-fluoro-2-methoxy-5-morpholin-4yl-benzamide:

A solution of 4-fluoro-2-methoxy-5-morpholin-4-yl-benzoic acid (0.90 g, 3.53 mmol) in dichloromethane (7.0 mL) was cooled to 0° C. and treated with oxalyl chloride (0.90 mL, 10.6 mmol.) and catalyzed with a catalytic amount of N,N-dimethylformamide (one drop). After 30 min, the reaction was heated to 40° C. for 1 h, cooled to room temperature and concentrated. The resulting brown solid was subsequently dissolved in dichloromethane (7.0 mL), cooled to 0° C., and treated with N,N-diisopropylethyl amine (3.0 mL, 17.6 mmol) and 5-bromo-2-fluoro-benzylamine hydrochloride( 1.0 g, 5.29 mmol). The mixture was stirred at room temperature overnight. The precipitated product was isolated by filtration. The remaining filtrate was washed with water and extrated with ethyl acetate. The organic layer was washed with saturated aq NaCl, dried over MgSO$_4$, concentrated and purified by MPLC (ethyl acetate in heptane). The resulting product was combined with the original precipitated product to provide N-(4-bromo-2-fluoro-benzyl)-4-fluoro-2-methoxy-5-morpholin-4yl-benzamide (0.94 g, 68%); $^1$H NMR (DMSO-$d_6$ 300 MHz) δ 8.84 (t, 6 Hz, 1H), 8.18 (s, 1H), 8.09 (dd, J$_1$=8.3 Hz, J$_2$=2.3 Hz, 1H), 7.77 (d, J=7.8 Hz, 1H), 7.61 (t, J=8.0 Hz, 1H), 7.46 (d, J=10.2 Hz, 1H), 7.10 (d, J=14.4 Hz, 1H), 4.58 (d, J=6 Hz, 2H), 3.87 (s, 3H), 3.71 (t, J=4.7 Hz, 4H), 2.90 (t, J=4.7 Hz, 4H).

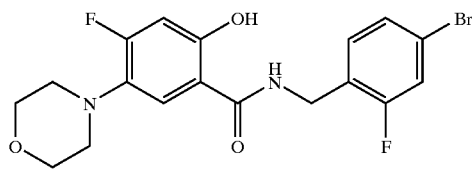

Step 4: N-(4-Bromo-2-fluoro-benzyl)-4-fluoro-2-hydroxy-5-morpholin-4-yl-benzamide:

A solution of N-(4-Bromo-2-fluoro-benzyl)-4-fluoro-2-methoxy-5-morpholin-4yl-benzamide (0.94 g, 24.1 mmol) in a 25% HBr/AcOH solution (25 mL) was heated to 100° C. for 6 h, cooled to room temperature and extracted with ethyl acetate. The crude product was filtered through a short pad of silica and concentrated to give the solid N-(4-bromo-2-fluoro-benzyl)-4-fluoro-2-hydroxy-5-morpholin-4-yl-benzamide (0.8 g, 88%): $^1$H NMR (DMSO-$d_6$ 300 MHz) δ 12.4 (s, 1H), 9.34 (br s, 1H), 8.12 (s, 1H), 8.05 (d, J=8.1 Hz, 1H), 7.72 (d, J=4.5 Hz, 1H), 7.56 (t, J=8.1 Hz, 1H), 7.47 (d, J=9.6 Hz, 1H), 6.69 (d, J=13.2 Hz, 1H), 4.56 (d, J=6 Hz, 2H), 3.65 (br d, J=3 Hz, 4H), 2.84 (br d, J=3 Hz, 4H).

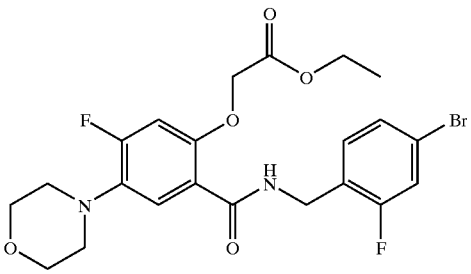

Step 5: [2-(4-Bromo-2-fluoro-benzylcarbamoyl)-5-fluoro-4-morpholin-4-yl-phenoxy]-acetic Acid Ethyl Ester:

A solution of N-(4-bromo-2-fluoro-benzyl)-4-fluoro-2-hydroxy-5-morpholin-4-yl-benzamide (0.8 g, 2.13 mmol) in acetone (11 mL), was treated with aq 2 N K$_2$CO$_3$ (1.6 mL, 3.20 mmol) and ethyl bromoacetate (0.35 mL, 3.20 mmol), and heated to 50° C. After stirring for 30 min, the reaction was cooled to room temperature and acidified to pH 7 with aq 2 N HCl. The resulting solution was extracted with ethyl acetate and washed with saturated NaCl. The organic layer was dried over MgSO$_4$, filtered and concentrated to give [2-(4-bromo-2-fluoro-benzylcarbamoyl)-5-fluoro-4-morpholin-4-yl-phenoxy]-acetic acid ethyl ester (0.8 g, 81%): $^1$H NMR (DMSO-$d_6$ 300 MHz) δ 9.05 (t, J=6 Hz, 1H), 8.18 (d, J=2.1 Hz, 1H), 8.09 (ddd, J$_1$=8.4 Hz, J$_2$=2.4 Hz, J$_3$=0.9 Hz, 1H), 7.79 (d, J=7.8 Hz, 1H), 7.61 (t, J=8.0 Hz, 1H), 7.54 (d, J=10.2 Hz, 1H), 7.15 (d, J=14.1 Hz, 1H), 4.94 (s, 2H), 4.63 (d, J=6 Hz, 2H), 4.14 (q, J=7.2 Hz, 2H), 3.71 (t, J=4.7 Hz, 4H), 2.92 (t, J=4.7 Hz, 4H), 1.16 (t, J=7.2 Hz, 3H).

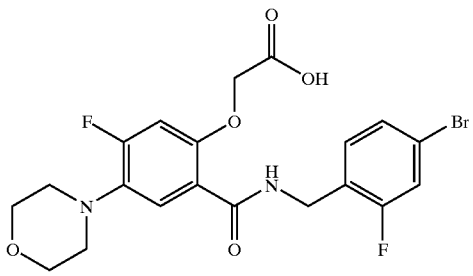

Step 6: [2-(4-Bromo-2-fluoro-benzylcarbamoyl)-5-fluoro-4-morpholin-4-yl-phenoxy]-acetic Acid A suspension of [2-(4-bromo-2-fluoro-benzylcarbamoyl)-5-fluoro-4-morpholin-4-yl-phenoxy]-acetic acid ethyl ester (0.8 g, 1.73 mmol) in ethanol (9 mL) was treated with aq 2 N NaOH (5.0 mL, 10.4 mmol). After stirring for 30 min, the reaction was concentrated in vacuo until most of the ethanol was removed. The mixture was acidified to pH 3 with aq 2 N HCl, extrated with ethyl acetate, and washed with saturated NaCl. The organic layer was dried over $MgSO_4$, filtered and concentrated to give [2-(4-bromo-2-fluoro-benzylcarbamoyl)-5-fluoro-4-morpholin-4-yl-phenoxy]-acetic acid (0.7 g, 93%) as a white crystalline solid: mp 180° C.; $R_f$ 0.17 (20% methanol in dichloromethane); $^1$H NMR (DMSO-$d_6$ 300 MHz) δ 9.21 (t, J=5.4 Hz, 1H), 8.17 (s, 1H), 8.09 (dd, $J_1$=8.1 Hz, $J_2$=2.4 Hz, 1H), 7.78 (d, J=7.5 Hz, 1H), 7.65–7.52 (m, 2H), 7.13 (d, J=13.8 Hz, 1H), 4.85 (s, 2H), 4.62 (d, J=6 Hz, 2H), 3.71 (t, J=4.7 Hz, 4H), 2.91 (t, J=4.8 Hz, 4H). Anal. calcd for $C_{20}H_{20}FN_3O_7$: C, 55.43; H, 4.65; N, 9.70. Found C, 55.49; H, 4.68; N, 9.60.

EXAMPLE 54

{5-Fluoro-2[(4,5,7-trifluoro-benzothiazol-2-ylmethyl)carbamoyl]-phenoxy}-acetic Acid

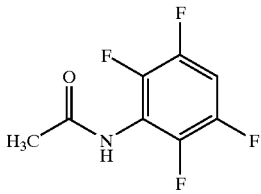

Step 1: 2,3,5,6-Tetrafluoroacetanilide

A solution of 2,3,5,6-tetrofluoroaniline (200 g, 1.21 mol) in anhydrouspyridine (103 mL, 1.27 mol) was treated with acetic anhydride (120 mL, 1.27 mol) and heated to 120° C. for 2 h. After cooling to room temperature, the solution was poured into ice-cold water (500 mL). The resulting precipitate was filtered, dissolved in ethyl acetate, dried over $MgSO_4$, filtered and concentrated. The solid material was washed with heptane (200 mL) and dried to give 2,3,5,6-tetrafluoroacetanilide as a white crystalline solid (206 g, 82%): mp 136–137° C.; $R_f$ 0.48 (50% ethyl acetate in heptane); $^1$H NMR (DMSO-$d_6$, 300 MHz) δ 10.10 (s, 1H), 7.87–7.74 (m, 1H), 2.09 (s, 3H). Anal. calcd for $C_8H_5F_4NO$: C, 46.39; H, 2.43; N, 6.67. Found C, 46.35; H, 2.39; N, 6.68.

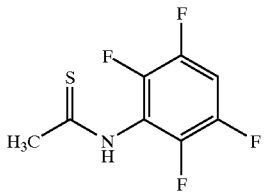

Step 2: 2,3,5,6-Tetrafluorothioacetanilide

A flame-dried; 4-necked 5,000 mL round-bottomed flask was charged with phosphorous pentasulfide (198 g, 0.45 mol) and diluted with anhydrous benzene (3,000 mL, 0.34 M). 2,3,5,6-tetrafluoroacetanilide (185 g, 0.89 mol) was added in one portion and the bright yellow suspension was heated to a gentle reflux for 3 h. The solution was cooled to 0° C. and filtered. The insoluble material was washed with ether (2×250 mL) and the combined filtrate was extracted with 10% aq NaOH (750 mL, 500 mL). After cooling the aqueous layer to 0° C., it was carefully acidified with conc. HCl (pH 2–3). The precipitated product was collected by filtration and washed with water (500 mL). The yellow-orange material was disolved in ethyl acetate (1,000 mL), dried over $MgSO_4$ and activated charcoal (3 g), filtered through a short pad of silica (50 g), and concentrated. The resulting solid was triturated with heptane (500 mL) and filtered to give 2,3,5,6-tetrafluorothioacetanilide (174.9 g, 88%): mp: 103–104° C.; $R_f$ 0.67 (50% ethyl acetate in heptane); $^1$H NMR (DMSO-$d_6$, 300 MHz) δ 11.20 (s, 1H), 8.00–7.88 (m, 1H), 2.66 (s, 3H). Anal. calcd for $C_8H_5F_4NS$: C, 43.05; H, 2.26; N, 6.28. Found C, 43.10; H, 2.23; N, 6.19.

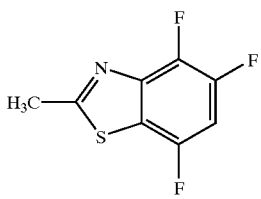

Step 3: 4,5,7-Trifluoro-2-methylbenzothiazole

A flame-dried 5,000 mL round-bottomed flask equipped with over-head stirrer was charged with sodium hydride (15.9 g, 0.66 mol) and diluted with anhydrous toluene (3,000 mL, 0.2 M). The suspension was cooled to 0° C., and treated with 2,3,5,6-tetrafluorothioacetanilide (134 g, 0.60 mol) in one portion. The solution was warmed to room temperature over 1 h, then heated to a gentle reflux. After 30 min, N,N-dimethylformamide (400 mL) was carefully added and the mixture was stirred for an additional 2 h. The solution was cooled to 0° C. and added to ice-water (2,000 mL). The solution was extracted with ethyl acetate (1,500 mL) and washed with saturated aq NaCl (1,000 mL). The organic layer was concentrated to dryness, diluted with heptane and successively washed with water (300 mL) and saturated aq NaCl (1,000 mL). The organic layer was dried over $MgSO_4$, filtered and concentrated to give 4,5,7-trifluoro-2-methylbenzothiazole (116.8 g, 96%) as a light brown solid: mp: 91–92° C.; $R_f$ 0.56 (30% ethyl acetate in heptane); $^1$H NMR (DMSO-$d_6$, 300 MHz) δ 7.76–7.67 (m, 1H), 2.87 (s, 3H);. Anal. calcd for $C_8H_4F_3NS$: C, 47.29; H, 1.98; N, 6.82; S, 15.78. Found C, 47.56; H, 2.07; N, 6.82; S, 15.59.

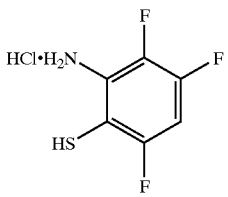

Step 4: 2-Amino-3,4,6-trifluorothiophenol Hydrochloride

A solution of 4,5,7-trifluoro-2-methylbenzothiazole (25.0 g, 123 mmol) in ethylene glycol (310 mL, 0.4 M) and 30% aq NaOH (310 mL, 0.4 M) was degassed using a nitrogen stream and subsequently heated to a gentle reflux (125° C.) for 3 h. The solution was cooled to 0° C. and acidified to pH 3–4 using conc. HCl (appox. 200 mL). The solution was extracted with ether (750 mL) and washed with water (200 mL). The organic layer was dried over $Na_2SO_4$, filtered and treated with 2,2-di-tert-butyl-4-methylphenol (0.135 g, 0.5 mol %). After concentrating to dryness, the crude product was dissolved in anhyd methanol (200 mL) and treated with an HCl solution in 1,4-dioxane (37 mL, 4 N, 148 mmol). The resulting mixture was concentrated to dryness, triturated with isopropylether (100 mL) and filtered to give 2-amino-3,4,6-trifluorothiophenol hydrochloride (19.3 g, 73%) as a light brown solid that was used without further purification. mp. 121–124° C.; $R_f$ 0.43 (30% ethyl acetate in heptane); Anal. calcd for $C_6H_5ClF_3NS$: C, 33.42; H, 2.34; N, 6.50; S, 14.87. Found C, 33.45; H, 2.27; N, 6.48; S, 14.96.

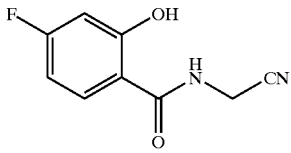

Step 5: N-Cyanomethyl-4-fluoro-2-hydroxy-benzamide:

A solution of 4-fluorosalicylic acid chloride (Example 1, 10 g, 57.3 mmol) in dichloromethane (114 mL) was treated with N,N-diisopropylethyl amine (25 mL, 143 mmol) and acetonitrile hydrochloride (7.95 g, 85.9 mmol). After stirring at 35° C. for 24 h, the solution was concentrated under reduced pressure, diluted with ethyl acetate, and washed successively with 2 N HCl and saturated aq NaCl. The resulting solution was dried over $MgSO_4$, filtered and concentrated. The resulting solid was suspended in dichloromethane, filtered and rinsed with heptane to give N-cyanomethyl-4-fluoro-2-hydroxy-benzamide (7.20 g, 65%): $^1$H NMR (DMSO-$d_6$ 300 MHz) δ 12.16 (br s, 1H), 9.17 (t, J=5.3 Hz, 1H), 7.88 (dd, $J_1$=8.7 Hz, $J_2$=6.3 Hz, 1H), 6.81–6.73 (m, 2H), 4.32 (d, J=5.7 Hz, 2H).

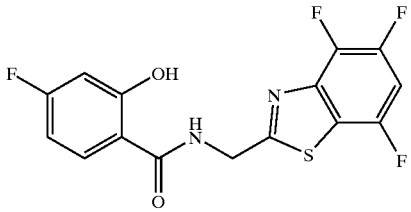

Step 6: 4-Fluoro-2-hydroxy-N-(4,5,7,-trifluoro-benzothiazol-2-ylmethyl)-benzamide:

A solution of N-cyanomethyl-4-fluoro-2-hydroxy-benzamide (2.93 g, 13.6 mmol) and 2-amino-4,5,7-trifluorothiophenol hydrochloride (6.64 g, 13.6 mmol) in ethanol (27.2 mL) was heated to reflux for 24 h. After cooling to room temperature, the mixture was the concentrated in vacuo, diluted with water and extracted with ethyl acetate. The organic layer was washed with saturated aq NaCl, dried over $MgSO_4$, filtered and concentrated. Purification by MPLC (10–100% ethyl acetate in heptane, 23 mL min, 75 min) provided 4-fluoro-2-hydroxy-N-(4,5,7,-trifluoro-benzothiazol-2-ylmethyl)-benzamide (1.00 g, 21%) as a white crystalline solid: $^1$H NMR (DMSO-$d_6$ 300 MHz) δ 12.35 (br s, 1H), 9.70 (t, J=5.4 Hz, 1H), 7.95 (dd, $J_1$=8.9 Hz, $J_2$=6.8 Hz, 1H), 7.80–7.70 (m, 1H), 6.83–6.74 (m, 2H), 4.94 (t, J=3 Hz, 2H).

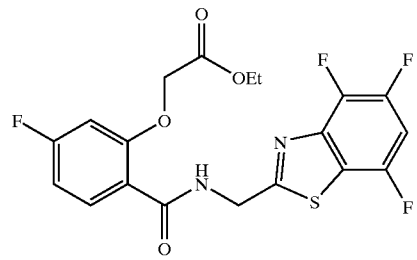

Step 7: {5-Fluoro-2[(4,5,7-trifluoro-benzothiazol-2-ylmethyl)carbamoyl]-phenoxy}-acetic Acid Ethyl Ester:

A solution of 4-fluoro-2-hydroxy-N-(4,5,7,-trifluoro-benzothiazol-2-ylmethyl)-benzamide (1.0 g, 2.8 mmol) in acetone (14 mL) was treated with aq 2 N $K_2CO_3$ (2.1 mL, 4.2 mmol) and ethyl bromoacetate (2 mL, 19 mmol) and heated to 45° C. for 5 h. After cooling to room temperature, the solution was acidified to a pH 1 with aq 2 N HCl. The resulting solution was diluted with ethyl acetate and washed with saturated NaCl. The organic layer was dried over $MgSO_4$, filtered and concentrated. Purification by MPLC (10–100% ethyl acetate in heptane 23 mL/min, 75 min) provided {5-fluoro-2[(4,5,7-trifluoro-benzothiazol-2-ylmethyl)carbamoyl]-phenoxy}-acetic acid ethyl ester (1.0 g, 81%) as a white crystalline solid: $^1$H NMR (DMSO-$d_6$ 300 MHz) δ 9.32 (t, J=5.9 Hz, 1H), 7.94 (dd, $J_1$=9.0 Hz, $J_2$=7.2 Hz, 1H), 7.80–7.70 (m, 1H), 7.13 (dd, $J_1$=11.1 Hz, $J_2$=2.4 Hz, 1H), 6.95 (dt, $J_1$=8.4 Hz, $J_2$=2.5 Hz, 1H), 5.02 (s, 2H), 4.94 (d, J=6 Hz, 2H), 4.17 (q, J=7.2 Hz, 2H), 1.18 (t, J=7.1 Hz, 3H).

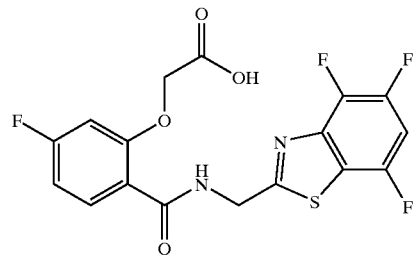

Step 8: {5-Fluoro-2[(4,5,7-trifluoro-benzothiazol-2-ylmethyl)carbamoyl]-phenoxy}-acetic Acid:

A suspension of {5-fluoro-2[(4,5,7-trifluoro-benzothiazol-2-ylmethyl)carbamoyl]-phenoxy}-acetic acid ethyl ester (1 g, 2.3 mmol) in ethanol (11 mL) was treated with aq 2 N NaOH (6.8 mL, 14 mmol) and stirred at room temperature. After stirring for 1 h, the solution was concentrated in vacuo and acidified to pH 1 with aq 2 N HCl. The resulting solution was diluted with ethyl acetate and washed with saturated NaCl. The organic layer was dried over MgSO$_4$, filtered, and concentrated to give {5-fluoro-2[(4,5,7-trifluoro-benzothiazol-2-ylmethyl)carbamoyl]-phenoxy}-acetic acid. (0.68 g, 73%) as a white crystalline solid. mp 172–174° C.; R$_f$ 0.38 (20% methanol in dichloromethane); $^1$H NMR (DMSO-d$_6$ 300 MHz) δ 13.25 (br s, 1H), 9.49 (t, J=6 Hz, 1H), 7.95 (dd, J$_1$=9 Hz, J$_2$=7.2 Hz, 1H), 7.78–7.69 (m, 1H), 7.11 (dd, J$_1$=11.0 Hz, J$_2$=2.3 Hz, 1H), 6.94 (dd, J$_1$=8.4 Hz, J$_2$=2.4 Hz, 1H), 4.94–4.92 (m, 4H). ESI-LC/MS m/z calcd for C$_{17}$H$_{10}$F$_4$N$_2$O$_4$S: 414.3. Found 413.0 (M−1)$^−$. Anal. calcd for C$_{17}$H$_{10}$F$_4$N$_2$O$_4$S: C, 49.28; H, 2.43; N, 6.76. Found C, 49.26; H, 2.47; N, 6.68.

EXAMPLE 55

{5-Fluoro-2-[(4,5,7-trifluoro-benzothiazol-2-ylmethyl)-thiocarbamoyl]-phenoxy}-acetic Acid

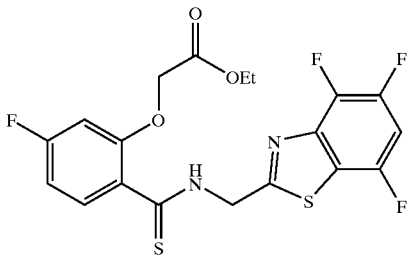

Step 1: {5-Fluoro-2-[(4,5,7-trifluoro-benzothiazol-2-ylmethyl)-thiocarbamoyl]-phenoxy}-acetic Acid Ethyl Ester:

In a flame dried flask under a nitrogen atmosphere, a suspension of phosphorus pentasulfide (2.9 g, 6.4 mmol) in pyridine (26 mL) was treated with {5-Fluoro-2[(4,5,7-trifluoro-benzothiazol-2-ylmethyl)carbamoyl]-phenoxy}-acetic acid ethyl ester (Example 54, 5.7 g, 13 mmol) and heated to 115° C. for 4 h. After cooling to room temperature, the mixture was diluted with water and ethyl acetate. The organic layer was washed successively with 2 N HCl (2×) and saturated NaCl, dried over MgSO$_4$, and concentrated. The resulting brown oil was chromatographed by MPLC (10–100% ethyl acetate in heptane, 23 mL/min, 75 min) to give {5-fluoro-2-[(4,5,7-trifluoro-benzothiazol-2-ylmethyl)-thiocarbamoyl]-phenoxy}-acetic acid ethyl ester (2.0 g, 34%): $^1$H NMR (DMSO-d$_6$ 300 MHz) δ 10.98 (br s, 1H), 7.79 (br t, J=6.0 Hz, 2H), 7.06 (br d, J=11.1 Hz, 1H), 6.90 (br t, J=9 Hz, 1H), 5.38 (br s, 2H), 4.89 (s, 2H), 4.12 (q, J=7.2 Hz, 2H), 1.16 (t, J=7.1 3H).

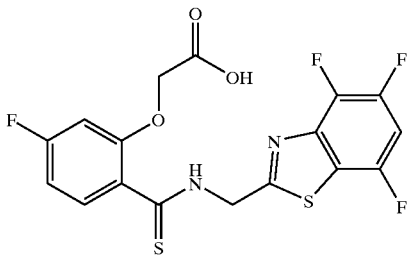

Step 2: {5-Fluoro-2-[(4,5,7-trifluoro-benzothiazol-2-ylmethyl)-thiocarbamoyl]-phenoxy}-acetic Acid:

A suspension of {5-fluoro-2-[(4,5,7-trifluoro-benzothiazol-2-ylmethyl)-thiocarbamoyl]-phenoxy}-acetic acid ethyl ester (2.0 g, 4.3 mmol) in ethanol (22 mL) and treated with aq 2 N NaOH (13 mL, 26 mmol). After stirring for 2 h, the solution was concentrated in vacuo to remove most of the ethanol and acidified to pH 1 with aq 2 N HCl. The product was extracted with ethyl acetate and washed with saturated NaCl. The organic layer was dried over MgSO$_4$, filtered and concentrated to give {5-fluoro-2-[(4,5,7-trifluoro-benzothiazol-2-ylmethyl)-thiocarbamoyl]-phenoxy}-acetic acid as an orange solid (1.05 g, 57%): mp 150° C.; R$_f$ 0.50 (20% methanol in dichloromethane); $^1$H NMR (DMSO-d$_6$ 300 MHz) δ 13.76 (br s, 1H), 7.83 (br t, J=8.0 Hz, 1H), 7.79–7.70 (m, 1H), 7.14 (dd, J$_1$=11.1 Hz, J$_2$=2.4 Hz, 1H), 6.84 (dt, J$_1$=8.4 Hz, J$_2$=2.4 Hz, 1H), 5.37 (d, J=5.7 Hz, 2H), 4.58 (s, 2H). ESI-LC/MS m/z calcd for C$_{17}$H$_{10}$F$_4$N$_2$O$_3$S$_2$: 430.4; Found 429.0 (M−1)$^−$. Anal. calcd for C$_{17}$H$_{10}$F$_4$N$_2$O$_3$S$_2$: C, 47.44; H, 2.34; N, 6.51; S, 14.90. Found C, 46.72; H, 2.81; N, 5.85; S, 12.02. Ethanol and water may still have been in the sample for the analytical values to be off.

EXAMPLE 56

{5-Fluoro-2-[(5-trifluoromethyl-benzothiazol-2-ylmethyl)-carbamoyl]-phenoxy}-acetic Acid

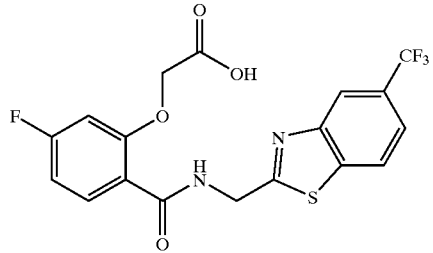

{5-Fluoro-2-[(5-trifluoromethyl-benzothiazol-2-ylmethyl)-carbamoyl]-phenoxy}-acetic acid was prepared in a manner analogous to that set forth in Example 54 (steps 5–8), except 5-amino-3-(trifluoromethyl)thiophenol hydrochloride was used in place of 2-amino-4,5,7-trifluorothiophenol hydrochloride in step 6: mp 206–208° C.; R$_f$ 0.32 (20% methanol in dichloromethane); $^1$H NMR (DMSO-d$_6$ 300 MHz) δ 13.36 (s, 1H), 9.45 (t, J=6 Hz, 1H), 8.30–8.28 (m, 2H), 7.96 (dd, J$_1$=9 Hz, J$_2$=7.2 Hz, 1H), 7.73 (dd, J$_1$=8.4 Hz, J$_2$=2.0 Hz, 1H), 7.11 (dd, J$_1$=11.1 Hz, J$_2$=2.4 Hz, 1H), 6.94 (dt, J$_1$=8.4 Hz, J$_2$=2.4 Hz, 1H), 4.95–4.93 (m, 4H). ESI-LC/MS m/z calcd for C$_{19}$H$_{13}$F$_4$NO$_4$S: 428.4; Found 428.0, 429.0 (M, M+1)$^+$. Anal. calcd for C$_{19}$H$_{13}$F$_4$NO$_4$S: C, 50.47; H, 2.82; N, 6.54. Found C, 50.54; H, 2.79; N, 6.57.

EXAMPLE 57

{5-Chloro-2-[(5-trifluoromethyl-benzothiazol-2-ylmethyl)-carbamoyl]-phenoxy}-acetic Acid

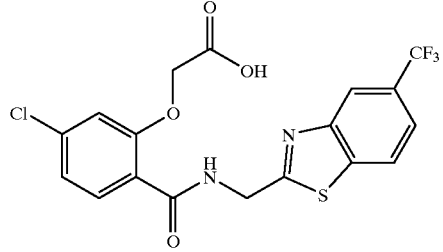

{5-Chloro-2-[(5-trifluoromethyl-benzothiazol-2-ylmethyl)-carbamoyl]-phenoxy}-acetic acid was prepared in a manner analogous to that set forth in Example 54 (steps 5–8), except 4-chlorosalicylic acid was used in place of 4-fluorosalicylic acid in step 5; and 5-amino-3-(trifluoromethyl)thiophenol hydrochloride was used in place of 2-amino-4,5,7-trifluorothiophenol hydrochloride in step 6: mp 225–227° C.; $R_f$ 0.44 (20% methanol in dichloroymethane); $^1$H NMR (DMSO-$d_6$ 300 MHz) δ 9.49 (t, J=6.2 Hz, 1H), 8.30–8.28 (m, 2 H), 7.89 (d, J=8.7 Hz, 1H), 7.73 (dd, $J_1$=8.7 Hz, $J_2$=1.8 Hz, 1H), 7.29 (d, J=1.8 Hz, 1H), 7.17 (dd, $J_1$=8.3 Hz, $J_2$=2.0 Hz, 1H), 4.98 (s, 2H), 4.94 (d, J=6 Hz, 2H). ESI-LC/MS m/z calcd for $C_{18}H_{12}ClF_3N_2O_4S$: 444.8; Found 443.0 (M−1)⁻. Anal. calcd for $C_{18}H_{12}ClF_3N_2O_4S$: C, 48.60; H, 2.72; N, 6.30; Cl, 7.97. Found: C, 48.47; H, 2.68; N, 6.20; Cl, 8.12.

EXAMPLE 58

[5-Fluoro-2-(3-nitro-benzylcarbamoyl)-phenoxy]-acetic Acid Benzyl Ester

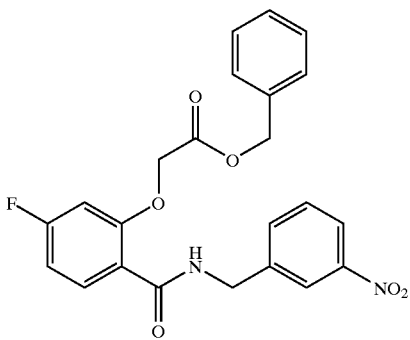

[5-Fluoro-2-(3-nitro-benzylcarbamoyl)-phenoxy]-acetic acid benzyl ester was prepared in a manner analogous to that set forth in Example 58 (steps 1–4), except benzyl chloroacetate was used in place of ethyl bromoacetate in step 3: mp 95–98° C.; $R_f$ 0.30 (40% ethyl acetate in heptane); $^1$H NMR (DMSO-$d_6$ 300 MHz) δ 8.98 (br t, J=6.2 Hz, 1H), 8.16 (s, 1H), 8.08 (br d, J=7.8 Hz, 1H), 7.88 (dd, $J_1$=8.7 Hz, $J_2$=7.2 Hz, 1H), 7.76 (d J=7.8 Hz, 1H), 7.59 (t, J=7.9 Hz, 1H), 7.36–7.32 (m, 5H), 7.12 (dd, $J_1$=10.9 Hz, $J_2$=2.4 Hz, 1H), 6.92 (dt, $J_1$=8.4 Hz, $J_2$=2.4 Hz, 1H), 5.19 (s, 2H), 5.08 (s, 2H), 4.56 (d, J=6 Hz, 2H). ESI-LC/MS m/z calcd for $C_{23}H_{19}FN_2O_6$: 438.4; Found 439.1 (M+1)⁺. Anal. calcd for $C_{23}H_{19}FN_2O_6$: C, 63.01; H, 4.37; N, 6.39. Found C, 63.09; H, 4.40; N, 6.40.

EXAMPLE 59

[5-Fluoro-2-(3-nitro-benzylcarbamoyl)-phenoxy]-acetic Acid 3-Methyl-butyl Ester

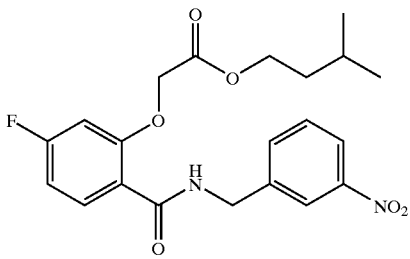

[5-Fluoro-2-(3-nitro-benzylcarbamoyl)-phenoxy]-acetic acid 3-methyl-butyl ester was prepared in a manner analogous to that set forth in Example 58 (steps 1–4), except isoamyl chloroacetate was used in place of ethyl bromoacetate in step 3: mp 65–68° C.; $R_f$ 0.33 (40% ethyl acetate in heptane); $^1$H NMR (DMSO-$d_6$ 300 MHz) δ 9.0 (t, J=6 Hz, 1H), 8.19 (s, 1H), 8.10 (d, J=7.2 Hz, 1H), 7.89 (dd, $J_1$=8.9 Hz, $J_2$=7.1 Hz, 1H), 7.79 (d, J=7.2 Hz, 1H), 7.61 (t, J=7.8 Hz, 1H), 7.11 (dd, $J_1$=11.3 Hz, $J_2$=2.4 Hz, 1H), 6.91 (dt, $J_1$=8.4 Hz, $J_2$=2.4 Hz, 1H), 5.01 (s, 2H), 4.63 (d, J=6 Hz, 2H), 4.13 (t, J=6.8 Hz, 2H), 1.58 (br spt, J=6.6 Hz, 1H), 1.42 (q, J=6.6 Hz, 2H), 0.83 (s, 3H), 0.81 (s, 3H). ESI-LC/MS m/z calcd for $C_{21}H_{23}FN_2O_6$: 418.4; Found 419.0 (M+1)⁺. Anal. alcd for $C_{21}H_{23}FN_2O_6$: C, 60.28; H, 5.54; N, 6.70. Found C, 60.16; H, 5.47; N, 6.63.

EXAMPLE 60

[5-Fluoro-2-(3-nitro-benzylcarbamoyl)-phenoxy]-acetic Acid Octyl Ester

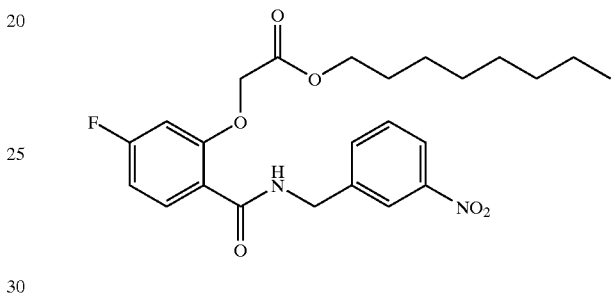

[5-Fluoro-2-(3-nitro-benzylcarbamoyl)-phenoxy]-acetic acid octyl ester was prepared in a manner analogous to that set forth in Example 58 (steps 1–4), except octyl chloroacetate was used in place of ethyl bromoacetate in step 3: mp 72–74° C.; $R_f$ 0.36 (40% ethyl acetate in heptane); $^1$H NMR (DMSO-$d_6$ 300 MHz) δ 9.0 (br t, J=6.3 Hz, 1H), 8.19 (s, 1H), 8.10 (d, J=8.4 Hz, 1H), 7.89 (dd, $J_1$=8.7 Hz, $J_2$=7.2 Hz, 1H), 7.79 (d, J=7.5 Hz, 1H), 7.61 (t, J=8.0 Hz, 1H), 7.17 (dd, $J_1$=11.0 Hz, $J_2$=2.3 Hz, 1H), 6.92 (dt, $J_2$=8.4 Hz, $J_2$=2.4 Hz, 1H), 5.01 (s, 2H), 4.63 (d, J=6 Hz, 2H), 4.09 (t, J=6.6 Hz, 2H), 1.51 (br t, J=6 Hz, 2H), 1.25–1.10 (m, 10H), 0.82 (t, J=6.6 Hz, 3H). ESI-LC/MS m/z calcd for $C_{24}H_{29}FN_2O_6$: 460.5; Found 461.0 (M+1)⁺. Anal. calcd for $C_{24}H_{29}FN_2O_6$: C, 62.60; H, 6.35; N, 6.08. Found C, 62.68; H, 6.41; N, 6.11.

EXAMPLE 61

[5-Fluoro-2-(3-nitro-benzylcarbamoyl)-phenoxy]-acetic Acid Butyl Ester

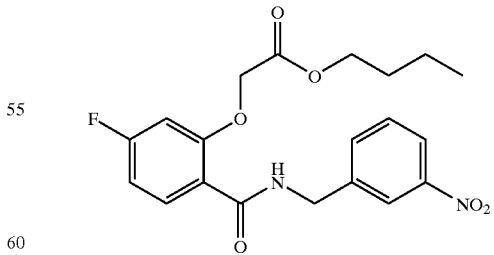

[5-Fluoro-2-(3-nitro-benzylcarbamoyl)-phenoxy]-acetic acid butyl ester was prepared in a manner analogous to that set forth in Example 58 (steps 1–4), except butyl chloroacetate was used in place of ethyl bromoacetate in step 3: mp 80–81° C.; $R_f$ 0.36 (40% ethyl acetate in heptane); $^1$H NMR (DMSO-d$_6$ 300 MHz) δ 9.0 (br t, J=6 Hz, 1H), 8.19 (s, 1H), 8.09 (d, J=8.1 Hz, 1H), 7.89 (dd, J$_1$=9 Hz, J$_2$=7.2 Hz, 1H), 7.79 (d, J=7.5 Hz, 1H), 7.61 (t, J=8 Hz, 1H), 7.11 (dd, J$_1$=11 Hz, J$_2$=2.4 Hz, 1H), 6.92 (dt, J$_1$=8.4 Hz, J$_2$=2.4 Hz, 1H), 5.01 (s, 2H), 4.63 (d, J=6 Hz, 2H), 4.10 (t, J=6.6 Hz, 2H), 1.51 (qnt, J=7.1 Hz, 2H), 1.25 (sx, J=7.5 Hz, 2H), 0.82 (t, J=7.2 Hz, 3H). ESI-LC/MS m/z calcd for C$_{20}$H$_{21}$FN$_2$O$_6$: 404.4; Found 405.0 (M+1)$^+$. Anal. calcd for C$_{20}$H$_{21}$FN$_2$O$_6$: C, 59.40; H, 5.23; N, 6.93. Found C, 59.49; H, 5.28; N, 6.90.

EXAMPLE 62

[5-Fluoro-2-(3-nitro-benzylcarbamoyl)-phenoxy]-acetic Acid Cyclohexyl Ester

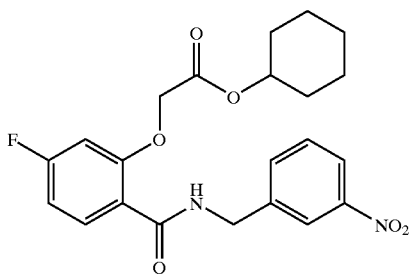

[5-Fluoro-2-(3-nitro-benzylcarbamoyl)-phenoxy]-acetic acid cyclohexyl ester was prepared in a manner analogous to that set forth in Example 58 (steps 1–4), except cyclohexyl chloroacetate was used in place of ethyl bromoacetate in step 3: mp 87–90° C.; R$_f$ 0.39 (40% ethyl acetate in heptane); $^1$H NMR (DMSO-d$_6$ 300 MHz) δ 9.01 (br t, J=6 Hz, 1H), 8.19 (s, 1H), 8.10 (dd, J$_1$=7.5 Hz, J$_2$=1.5 Hz, 1H), 7.90 (dd, J$_1$=9.0 Hz, J$_2$=7.1 Hz, 1H), 7.79 (d, J=7.5 Hz, 1H), 7.61 (t, J=8 Hz, 1H), 7.10 (dd, J$_1$=11 Hz, J$_2$=2.3 Hz, 1H), 6.92 (dt, J$_1$=8.4 Hz, J$_2$=2.4 Hz, 1H), 4.99 (s, 2H), 4.78–4.72 (m, 1H), 4.63 (d, J=6.3 Hz, 2H), 1.72 (br s, 2H), 1.57 (br d, J=5.4 Hz, 2H), 1.44–1.15 (m, 6H). ESI-LC/MS m/z calcd for C$_{22}$H$_{23}$FN$_2$O$_6$: 430.4; Found 431.0 (M+1)$^+$. Anal. calcd for C$_{22}$H$_{23}$FN$_2$O$_6$: C, 61.39; H, 5.39; N, 6.51. Found C, 61.48; H, 5.43; N, 6.57.

EXAMPLE 63

[5-Fluoro-2-(3-nitro-benzylcarbamoyl)-phenoxy]-acetic Acid 2-Ethyl-hexyl Ester

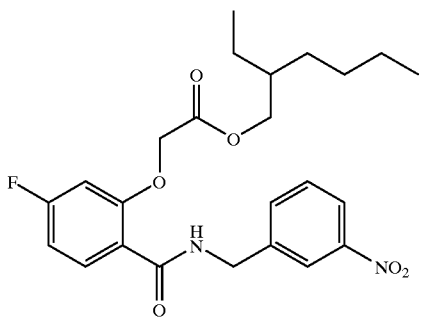

[5-Fluoro-2-(3-nitro-benzylcarbamoyl)-phenoxy]-acetic acid 2-ethyl-hexyl ester was prepared in a manner analogous to that set forth in Example 58 (steps 1–4), except 2-ethylhexyl chloroacetate was used in place of ethyl bromoacetate in step 3: mp 59–60° C.; R$_f$ 0.46 (40% ethyl acetate in heptane); $^1$H NMR (DMSO-d$_6$ 300 MHz) δ 8.99 (t, J=6 Hz, 1H), 8.19 (s, 1H), 8.09 (br d, J=8.1 Hz, 1H), 7.89 (dd, J$_1$=7.8 Hz, J$_2$=7.2 Hz, 1H), 7.79 (d, J=7.5 Hz, 1H), 7.61 (t, J=8 Hz, 1H), 7.11 (dd, J$_1$=11.2 Hz, J$_2$=2.3 Hz, 1H), 6.91 (dt, J$_1$=8.4 Hz, J$_2$=2.3 Hz, 1H), 5.04 (s, 2H), 4.63 (br d, J=3.6 Hz, 2H), 4.01 (dd, J$_1$=5.4 Hz, J$_2$=1.1 Hz, 2H), 1.50–1.44 (m, 1H), 1.25–1.15 (m, 8H), 0.82–0.70 (m, 6H). ESI-LC/MS m/z calcd for C$_{24}$H$_{29}$FN$_2$O$_6$: 460.5; Found 461.0 (M+1)$^+$. Anal. calcd for C$_{24}$H$_{29}$FN$_2$O$_6$: C, 62.60; H, 6.35; N, 6.08. Found C, 62.66; H, 6.34; N, 6.05.

EXAMPLE 64

[5-Fluoro-2-(3-nitro-benzylcarbamoyl)-phenoxy]-acetic Acid 2-Methoxy-ethyl Ester

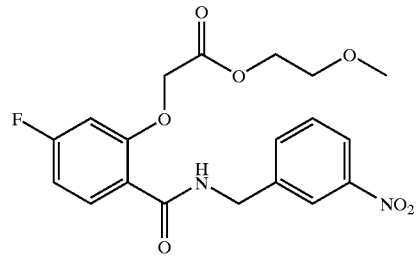

[5-Fluoro-2-(3-nitro-benzylcarbamoyl)-phenoxy]-acetic acid 2-methoxy-ethyl ester was prepared in a manner analogous to that set forth in Example 58 (steps 1–4), except 2-methoxyethyl chloroacetate was used in place of ethyl bromoacetate in step 3: mp 112–115° C.; R$_f$ 0.14 (40% ethyl acetate in heptane); $^1$H NMR (DMSO-d$_6$ 300 MHz) δ 9.0 (br t, J=6 Hz, 1H), 8.19 (br s, 1H), 8.11 (br dd, J$_1$=8.1 Hz, J$_2$=0.9 Hz, 1H), 7.89 (dd, J$_1$=8.7 Hz, J$_2$=6.9 Hz, 1H), 7.80 (d, J=7.5 Hz, 1H), 7.62 (t, J=8 Hz, 1H), 7.11 (dd, J$_1$=11.4 Hz, J$_2$=2.4 Hz, 1H), 6.93 (dt, J$_1$=8.4 Hz, J$_2$=2.4 Hz, 1H), 5.04 (s, 2H), 4.63 (d, J=6 Hz, 2H), 4.25 (t, J=4.7 Hz, 2H), 3.52 (t, J=4.5 Hz, 2H), 3.22 (s, 3H). ESI-LC/MS m/z calcd for C$_{19}$H$_{19}$FN$_2$O$_7$: 406.4; Found 407.0 (M+1)$^+$. Anal. calcd for C$_{19}$H$_{19}$FN$_2$O$_7$: C, 56.16; H, 4.71; N, 6.89. Found C, 56.13; H, 4.73; N, 6.94.

EXAMPLE 65

[5-Fluoro-2-(3-nitro-benzylthiocarbamoyl)-phenoxy]-acetic Acid Octyl Ester

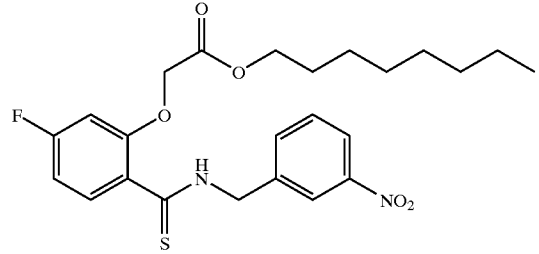

[5-Fluoro-2-(3-nitro-benzylthiocarbamoyl)-phenoxy]-acetic acid octyl ester was prepared in a manner analogous to that set forth in Example 32, except [5-Fluoro-2-(3-nitro-benzylcarbamoyl)-phenoxy]-acetic acid octyl ester (Example 60) was used in place of [5-fluoro-2-(3-nitro-benzylcarbamoyl)-phenoxy]-acetic acid ethyl ester in step 1: mp 69–72° C.; $R_f$ 0.60 (40% ethyl acetate in heptane); $^1$H NMR (DMSO-$d_6$ 300 MHz) δ 10.70 (br s, 1H), 8.23 (s, 1H), 8.15 (dd, $J_1$=8.1 Hz, $J_2$=2.1 Hz, 1H), 7.83 (d, J=7.5 Hz, 1H), 7.72–7.59 (m, 2H), 7.03 (dd, $J_1$=11.4 Hz, $J_2$=2.4 Hz, 1H), 6.86 (dt, $J_1$=8.4 Hz, $J_2$=2.4 Hz, 1H), 5.06 (br s, 2H), 4.07 (t, J=6.6 Hz, 2H), 1.54–1.48 (m, 2H), 1.28–1.16 (m, 10H), 0.83 (br t, J=6.6 Hz, 3H). ESI-LC/MS m/z calcd for $C_{24}H_{29}FN_2O_5S$: 476.6; Found 477.0 (M+1)$^+$. Anal. calcd for $C_{24}H_{29}FN_2O_5S$: C, 60.49; H, 6.13; N, 5.88; S, 6.73. Found C, 60.25; H, 6.03; N, 5.79; S, 6.58.

EXAMPLE 66

[5-Fluoro-2-(3-nitro-benzylthiocarbamoyl)-phenoxy]-acetic Acid 3-Methyl-butyl Ester

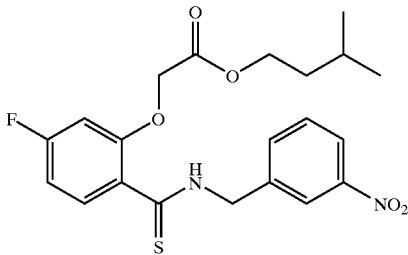

[5-Fluoro-2-(3-nitro-benzylthiocarbamoyl)-phenoxy]-acetic acid 3-methyl-butyl ester was prepared in a manner analogous to that set forth in Example 32, except [5-Fluoro-2-(3-nitro-benzylcarbamoyl)-phenoxy]-acetic acid 3-methyl-butyl ester (Example 59) was used in place of [5-fluoro-2-(3-nitro-benzylcarbamoyl)-phenoxy]-acetic acid ethyl ester in step 1: mp 56–58° C. $R_f$ 0.59 (40% ethyl acetate in heptane); $^1$H NMR (DMSO-$d_6$ 300 MHz) δ 10.68 (br s, 1H), 8.23 (s, 1H), 8.16 (d, J=8.1 Hz, 1H), 7.83 (d, J=7.8 Hz, 1H), 7.72–7.60 (m, 2H), 7.03 (d, J=8.7 Hz, 1H), 6.86 (dt, $J_1$=8.4 Hz, $J_2$=2.1 Hz, 1H), 5.06 (br s, 2H), 4.90 (s, 2H), 4.11 (t, J=6.6 Hz, 2H), 1.58 (br spt, J=6.5, 1H), 1.43 (q, J=6.7 Hz, 2H), 0.84 (s, 3H), 0.82 (s, 3H). ESI-LC/MS m/z calcd for $C_{21}H_{23}FN_2O_5S$: 434.5;. Found 435.0 (M+1)$^+$. Anal. calcd for $C_{21}H_{23}FN_2O_5S$: C, 58,05; H, 5.34; N, 6.45; S, 7.38. Found C, 58,09; H, 5.26; N, 6.41; S, 7.31.

EXAMPLE 67

[5-Fluoro-2-(3-nitro-benzylcarbamoyl)-phenoxy]-acetic Acid 2-Diethylammonium-ethyl Ester Hydrochloride

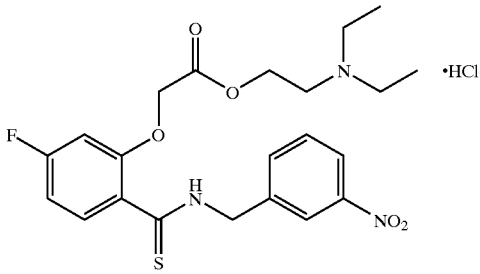

A solution of [5-fluoro-2-(3-nitro-benzylcarbamoyl)-phenoxy]-acetic acid (Example 32, 2.0 g, 5.74 mmol) in acetonitrile (150 mL), was treated with CsF-Celite$^1$ (1.9 g, 8.61 mmol) and 2-bromo-N,N-diethyl ethylamine hydrobromide (3.0 g, 11.5 mmol). The suspension was heated to reflux for 24 h, cooled to room temperature and concentrated. The mixture as diluted withethyl acetate and filtered to remove the insoluble salts. The filtrate was washed successively with aq 2 N $K_2CO_3$ and saturated NaCl. The organic layer was dried over $MgSO_4$, filtered and concentrated. The thick oil was subsequently treated with anhyd 1.0 M HCl in ether (6 mL, 1 equiv.) to give [5-fluoro-2-(3-nitro-benzylcarbamoyl)-phenoxy]-acetic acid 2-diethylammonium-ethyl ester hydrochloride (1.2 g, 43%): mp 96–100° C.; $R_f$ 0.35 (10% methanol in dichloromethane); $^1$H NMR (DMSO-$d_6$ 300 MHz) δ 10.50 (br s, 1H), 9.01 (t, J=6.2 Hz, 1H), 8.19 (s, 1H), 8.10 (br d, J=7.8 Hz, 1H), 7.88–7.79 (m, 2H), 7.62 (t, J=7.8 Hz, 1H), 7.19 (dd, $J_1$=11.1 Hz, $J_2$=2.4 Hz, 1H), 6.92 (dt, $J_{1=8.1}$ Hz, $J_2$=2.2 Hz, 1H), 5.09 (s, 2H), 4.62 (d, J=6.3 Hz, 2H), 4.48. (t, J=5.1 Hz, 2H), 3.38–3.35 (m, 2H), 3.13–3.08 (m, 4H), 1.18 (t, J=7.2 Hz, 6H). ESI-LC/MS m/z calcd for $C_{22}H_{26}FN_3O_6$: 447.5; Found 448 (M+1)$^+$.

EXAMPLE 68

[5-Fluoro-2-(3-nitro-benzylcarbamoyl)-phenoxy]-acetic Acid 2-Trimethylammonium Chloride-ethyl Ester

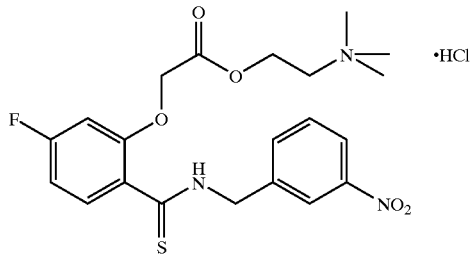

A solution of [5-fluoro-2-(3-nitro-benzylcarbamoyl)-phenoxy]-acetic acid (1.4 g, 4.02 mmol) in acetonitrile (300 mL) was treated with CsF-Celite$^1$ (1.30 g, 6.03 mmol) and (2-bromoethyl) trimethylammonium bromide (1.99 g, 8.04 mmol). The suspension was heated to reflux for 24 h, cooled and concentrated. The resulting mixture was diluted with ethyl acetate and filtered to remove the insoluble salts. The filtrate was concentrated and subsequently purified by reverse-phase HPLC (10–90% acetonitrile in water with 0.05% HCl, 10 mL/min, 35 min) to give [5-fluoro-2-(3-nitro-benzylcarbamoyl)-phenoxy]-acetic acid 2-trimethylammonium chloride-ethyl ester (0.5 g, 26%). mp 100–105° C.; $R_f$ 0.30 (20% methanol in dichloromethane); $^1$H NMR (DMSO-$d_6$ 300 MHz) δ9.00 (t, J=5.9 Hz, 1H), 8.20 (s, 1H), 8.12 (br d, J=8.1 Hz, 1H), 7.88–7.79 (m, 2H), 7.63 (t, J=8.0 Hz, 1H), 7.14 (dd, $J_1$=11.1 Hz, $J_2$=2.4 Hz, 1H), 6.95 (dt, $J_1$=8.4 Hz, $J_2$=2.4 Hz, 1H), 5.05 (s, 2H), 4.63 (d, J=6 Hz, 2H), 4.57 (br s, 2H), 3.69–3.66 (m, 2H), 3.10 (s, 9H). ESI-LC/MS m/z calcd for $C_{21}H_{25}ClFN_3O_6$: 469.90. Found 434.0 (M−35.5-chloride)$^+$.

EXAMPLE 69

[2-(4-Bromo-2-fluoro-benzylcarbamoyl)-4-methoxy-phenoxy]-acetic Acid

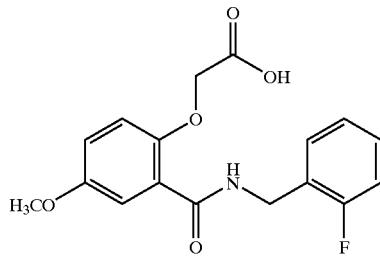

[2-(4-Bromo-2-fluoro-benzylcarbamoyl)-4-methoxy-phenoxy]-acetic acid was prepared in a manner analogous to that set forth in Example 1, except 2-hydroxy-5-methoxy-benzoic acid was used in of 4-chlorosalicyclic acid in step 1: $R_f$ 0.11 (10% methanol in dichloromethane); $^1$H NMR (DMSO-$d_6$, 300 MHz) δ 9.23 (br t, J=6.1 Hz, 1H), 7.50 (br d, J=9.1 Hz, 1H), 7.40–4.34 (m, 3H), 7.11–7.00 (m, 2H), 4.79 (s, 2H), 4.49 (d, J=5.6 Hz, 2H), 3.71 (s, 3H). ESI-LC/MS m/z calcd for $C_{17}H_{15}BrFNO_5$: 411.01 found XX (M+1)$^-$. Anal. calcd for $C_{17}H_{15}BrFNO_5$: C, 49.53; H, 3.67; N, 3.40. Found C, 49.47; H, 3.65; N, 3.33.

Representative compounds of the invention were tested for their potency, selectivity and efficacy as inhibitors of human aldose reductase. The potency or aldose reductase inhibiting effects of the compounds were tested using methods similar to those described by Butera et al. in *J. Med. Chem.* 1989, 32, 757. Using this assay, the concentrations required to inhibit human aldose reductase (hALR2) activity by 50% (IC50) were determined.

In a second assay, a number of the same compounds were tested for their ability to inhibit aldehyde reductase (hALR1), a structurally related enzyme. The test method employed were essentially those described by Ishii, et al., *J. Med. Chem.* 1996 39: 1924. Using this assay, the concentrations required to inhibit human aldehyde reductase activity by 50% (IC50) were determined.

From these data, the hALR1/hALR2 ratios were determined. Since high potency of test compounds as inhibitors of aldose reductase is desirable, low hALR2 IC50 values are sought. On the other hand, high potency of test compounds as inhibitors of aldehyde reductase is undesirable, and high hALR1 IC50s values are sought. Accordingly, the hALR1/hALR2 ratio is used to determine the selectivity of the test compounds. The importance of this selectivity is described in Kotani, et al., *J. Med. Chem.* 40: 684, 1997.

The results of all these tests are combined and illustrated in Table 1.

| Ex. # | hALR2 (aldose) (IC$_{50}$) | hALR1 (aldehyde) (IC$_{50}$) | hALR1/ hALR2 |
|---|---|---|---|
| 1 | 30 nM | 14,000 nM | 470 |
| 4 | 39 nM | | |
| 5 | 6 nM | 19% @ 25 µM | >4,200 |
| 11 | 29 nM | | |
| 14 | 34 nM | 18,000 nM | 530 |
| 17 | 46 nM | 18,000 nM | 390 |
| 18 | 150 nM | | |
| 19 | 64 nM | | |
| 20 | 69 nM | 11,000 nM | 160 |
| 21 | 200 nM | | |
| 23 | 180 nM | | |
| 24 | 83 nM | | |
| 25 | 11 nM | 48% @ 100 µM | >9,100 |
| 26 | 9 nM | | |
| 27 | 8 nM | 34,000 nM | 4,300 |
| 28 | 55 nM | 6,600 nM | 120 |
| 29 | 8 nM | | |
| 30 | 37 nM | | |
| 32 | 6 nM | 35,000 nM | 5,800 |
| 33 | 34 nM | 33,000 nM | 970 |
| 34 | 37 nM | | |
| 35 | 12 nM | | |
| 36 | 33 nM | | |
| 45 | 24 nM | 5,800 nM | 240 |
| 46 | 24 nM | 31,000 nM | 1,300 |
| 47 | 8 nM | | |
| 48 | 7 nM | | |
| 49 | 6 nM | 44,000 nM | 7,300 |
| 50 | 7 nM | 14,000 nM | 2,000 |
| 51 | 11 nM | 12,000 nM | 1,100 |
| 52 | 7 nM | | |
| 53 | 7 nM | 54,000 nM | 7,700 |
| 54 | 11 nM | 22,000 nM | 2,000 |
| 55 | 15 nM | 17,000 nM | 1,100 |
| 56 | 29 nM | 22,000 nM | 760 |
| 57 | 35 nM | | |
| Tolrestat | 13 nM | 1,940 nM | 149 |

The results show the superior potency, selectivity and efficacy of representative compounds of the invention. Such compounds are useful in the treatment of chronic complications arising from diabetes mellitus, such as diabetic cataracts, retinopathy and neuropathy. Accordingly, an aspect of the invention is treatment of such complications with the inventive compounds; treatment includes both prevention and alleviation. The compounds are useful in the treatment of, for example, diabetic cataracts, retinopathy, nephropathy and neuropathy.

In a third, optional, set of experiments, the compounds can be assayed for their ability to normalize or reduce sorbitol accumulation in the sciatic nerve of streptozotocin-induced diabetic rats. The test methods employed to determine the efficacy are essentially those of Mylari, et al., *J. Med. Chem.* 34: 108, 1991.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

I claim:
1. A compound of the formula:

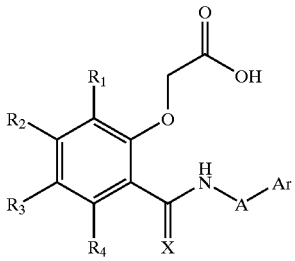

or pharmaceutically acceptable salts thereof wherein
A is a $C_1$–$C_4$ alkylene group optionally substituted with $C_1$–$C_2$ alkyl or mono- or disubstituted with halogen;
X is oxygen or sulfur;
$R_1$, $R_2$, $R_3$ and $R_4$ are each independently
hydrogen, halogen, or nitro, or an alkyl group of 1–6 carbon atoms optionally substituted with one or more halogens;
$OR_7$, $SR_7$, $S(O)R_7$, $S(O)_2R_7$, $C(O)N(R_7)_2$, or $N(R_7)_2$, wherein each $R_7$ is independently hydrogen, an alkyl group of 1–6 carbon atoms (which may be substituted with one or more halogens) or benzyl, where the phenyl portion is optionally substituted with up to three groups independently selected from halogen, $C_1$–$C_6$ alkyl, $C_1$–$C_6$ alkoxy, amino, andmono- or di($C_1$–$C_6$)alkylamino;
phenyl or heteroaryl each of which phenyl or heteroaryl is optionally substituted with up to three groups independently selected from halogen, $C_1$–$C_6$ alkyl, $C_1$–$C_6$ alkoxy, amino, and morno- or di($C_1$–$C_6$) alkylamino;
phenoxy where the phenyl portion is optionally substituted with up to three groups independently selected from halogen, $C_1$–$C_6$ alkyl, $C_1$–$C_6$ alkoxy, amino, and mono- or di($C_1$–$C_6$) alkylamino; or
a group of the formula

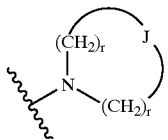

where
J is a bond, $CH_2$, oxygen, or nitrogen; and
each r is independently 2 or 3; and
Ar represents aryl which is optionally substituted with up to five groups.

2. A compound according to claim 1, wherein A is $CH_2$; and each of $R_1$–$R_4$ is independently hydrogen, halogen, $C_1$–$C_2$ alkyl, phenoxy, benzyloxy, or $C_1$–$C_2$ alkoxy.

3. A compound according to claim 2, wherein each of $R_1$–$R_4$ is independently hydrogen, bromo, chloro, $C_1$–$C_2$ alkyl, phenoxy, benzyloxy, or $C_1$–$C_2$ alkoxy.

4. A compound according to claim 1, wherein $R_1$ and $R_4$ are hydrogen, methyl or ethyl; and $R_2$ and $R_3$ are independently hydrogen, bromo, chloro, fluoro, $C_1$–$C_2$ alkyl, phenoxy, benzyloxy, $C_1$–$C_2$ alkoxy, amino, mono or di($C_1$–$C_3$ alkyl)amino, morpholinyl, piperidin-1-yl, or piperazin-1-yl.

5. A compound according to claim 4, wherein at least one of $R_2$ and $R_3$ is hydrogen, and both $R_1$ and $R_4$ are hydrogen.

6. A compound according to claim 1, wherein
A is methylene;
Ar is
phenyl where
(i) the phenyl group is optionally substituted with up to 3 groups independently selected from halogen, an alkyl group of 1–6 carbon atoms, $C_1$–$C_6$ alkyl substituted with one or more halogens, nitro, $OR_7$, $SR_7$, $S(O)R_7$, $S(O)_2R_7$ and $N(R_7)_2$ wherein $R_7$ is hydrogen, an alkyl group of 1–6 carbon atoms optionally substituted with one or more halogens, or benzyl where the phenyl portion is optionally substituted with up to three groups independently selected from halogen, $C_1$–$C_6$ alkyl, $C_1$–$C_6$ alkoxy, amino, and mono- or di($C_1$–$C_6$) alkylamino;
(ii) the phenyl group is optionally monosubstituted with any of the groups described above in (i) and disubstituted with a $C_1$–$C_5$ alkylene group forming a cycloalkyl ring fused to the phenyl where the $C_1$–$C_5$ alkylene group is optionally mono- or disubstituted with hydroxy, halogen, $C_1$–$C_2$ alkyl, $C_1$–$C_2$ alkoxy, amino or mono- or di($C_1$–$C_2$)alkyl amino, and where the $C_1$–$C_5$ alkylene group optionally contains one or two hetero atoms selected from oxygen, nitrogen and sulfur; or
(iii) the phenyl group is optionally substituted with up to 3 groups as described above in (i) and further condensed with benzo where the benzo is optionally substituted with one or two of halogen, cyano, nitro, trifluoromethyl, perfluoroethyl, trifluoroacetyl, or ($C_1$–$C_6$)alkanoyl, hydroxy, ($C_1$–$C_6$)alkyl, ($C_1$–$C_6$)alkoxy, ($C_1$–$C_6$) alkylthio, trifluoromethoxy, trifluoromethylthio, ($C_1$–$C_6$) alkylsulfinyl, ($C_1$–$C_6$)alkylsulfonyl; and
$R_1$–$R_4$ are independently hydrogen, halogen, $C_1$–$C_2$ alkyl, phenoxy, benzyloxy or phenyl where each phenyl portion is optionally substituted with $C_1$–$C_6$ alkyl, halogen, $C_1$–$C_6$ alkoxy, hydroxy, amino or mono- or di($C_1$–$C_6$)alkylamino.

7. A compound according to claim 6, wherein $R_1$ and $R_4$ are hydrogen, methyl or ethyl; and $R_2$ and $R_3$ are independently hydrogen, bromo, chloro, fluoro, $C_1$–$C_2$ alkyl, phenoxy, benzyloxy, $C_1$–$C_2$ alkoxy, amino, mono or di($C_1$–$C_3$ alkyl)amino, morpholinyl, piperidin-1-yl, or piperazin-1-yl.

8. A compound according to claim 6, wherein both $R_1$ and $R_4$ are hydrogen or $C_1$–$C_3$ alkyl.

9. A compound according to claim 8, wherein at least one of $R_2$ and $R_3$ is hydrogen, and both $R_1$ and $R_4$ are hydrogen.

10. A compound of the formula:

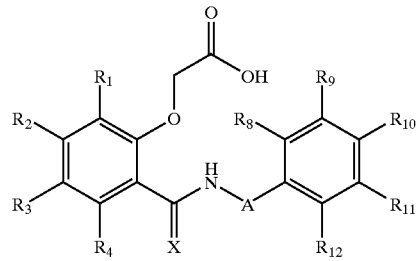

or a pharmaceutically acceptable salt thereof wherein
A is a $C_1$–$C_4$ alkylene group optionally substituted with $C_1$–$C_2$ alkyl;

X is oxygen, sulfur or $NR_6$, wherein each $R_6$ is hydrogen, cyano or an alkyl group of 1–6 carbon atoms optionally substituted with one or more halogens;

$R_1$, $R_2$, $R_3$ and $R_4$ are each independently hydrogen, halogen, an alkyl group of 1–6 carbon atoms optionally substituted with one or more halogens, nitro, $OR_7$, $SR_7$, $S(O)R_7$, $S(O)_2NR_7$, $C(O)N(R_7)_2$, or $N(R_7)_2$, wherein each $R_7$ is independently hydrogen, an alkyl group of 1–6 carbon atoms optionally substituted with one or more halogens or benzyl where the phenyl portion is optionally substituted with up to three groups independently selected from halogen, $C_1$–$C_6$ alkyl, $C_1$–$C_6$ alkoxy, amino, and mono- or di($C_1$–$C_6$)alkylamino;

phenyl or heteroaryl, each of which phenyl or heteroaryl is optionally substituted with up to three groups independently selected from halogen, $C_1$–$C_6$ alkyl, $C_1$–$C_6$ alkoxy, amino, and mono- or di($C_1$–$C_6$) alkylamino;

phenoxy where the phenyl portion is optionally substituted with up to three groups independently selected from halogen, $C_1$–$C_6$ alkyl, $C_1$–$C_6$ alkoxy, amino, and mono- or di($C_1$–$C_6$)alkylamino; or a group of the formula

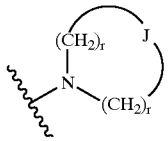

where
J is a bond, $CH_2$, oxygen, or nitrogen; and
each r is independently 2, or 3; and
$R_8$, $R_9$, $R_{10}$, $R_{11}$ and $R_{12}$ in combination, represent hydrogen, or 1–3 groups selected from hydroxy, $C_1$–$C_6$ alkoxy, $C_1$–$C_6$ alkyl, trifluoromethylthio, fluorine, chlorine, bromine, trifluoromethyl, trifluoromethoxy, or nitro.

11. A compound according to claim 10, wherein $R_1$ and $R_4$ are hydrogen, methyl or ethyl; and $R_2$ and $R_3$ are independently hydrogen, bromo, chloro, fluoro, flouro $C_1$–$C_2$ alkyl, phenoxy, benzyloxy, $C_1$–$C_2$ alkoxy, amino, mono or di($C_1$–$C_3$ alkyl)amino, morpholinyl, piperidin-1-yl, or piperazin-1-yl.

12. A compound according to claim 11, wherein $R_8$–$R_{12}$ represent one trifluoroacetyl or trifluoromethylthio, or one or two of fluoro chloro, bromo, hydroxy, methyl, methoxy, trifluoromethyl, or one or, preferably, two fluoro and one trifluoromethyl, or two fluoro or two trifluoromerehyl with one methoxy, or three fluoro.

13. A compound according to claim 10, wherein $R_1$ and $R_4$ are hydrogen, methyl or ethyl; and $R_2$ and $R_3$ are independently hydrogen, bromo, chloro, fluoro, $C_1$–$C_2$ alkyl, phenoxy, benzyloxy, $C_1$–$C_2$ alkoxy, amino, mono or di($C_1$–$C_3$ alkyl)amino, morpholinyl, piperidin-1-yl, or piperazin-1-yl.

14. A compound according to claim 13, wherein both $R_1$ and $R_4$ are hydrogen or $C_1$–$C_3$ alkyl.

15. A compound according to claim 14, wherein at least one of $R_2$ and $R_3$ is hydrogen, and both $R_1$ and $R_4$ are hydrogen.

16. A pharmaceutical composition comprising a pharmaceutically acceptable carrier and an effective amount of a compound according to claim 1.

17. A pharmaceutical composition according to claim 16, further comprising an Angotensin Converting Enzyme inhibitor.

18. A pharmaceutical composition as claimed 17, wherein the angiotensin converting enzyme inhibitor is selected from benazepril, benazeprilar, captopril, delapril, fentiapril, fosinopril, libenzapril, moexipril, pentopril, petindopril, pivopril, quinapril, quinaprilat, ramipril, spirapril, spiraprilat, zofenopril, ceronapril, enalapril, indolapril, omaprilat, lisinopril, alacepril; cilazapril, and the pharmaceutically acceptable salts thereof.

19. A pharmaceutical composition according to claim 17, wherein the angiotensin converting enzyme inhibitor is selected from the group consisting of selected from benazepril, benazeprilar, captopril, delapril, fentiapril, fosinopril, libenzapril, moexipril, pentopril, petindopril, pivopril, quinapril, quinaprilat, ramipril, spirapril, spiraprilat, zofenopril, ceronapril, enalapril, indolapril, omaprilat, lisinopril, alacepril, cilazapril, and the pharmaceutically acceptable salts thereof.

20. A method for treating diabetic complications comprising administering to a patient suffering from such complications an effective amount of a compound of according to claim 1.

21. A method according to claim 20, where the compund is administered to the patient as a pharmaceutical composition comprising the compound of claim 1 and a pharmaceutically acceptable carrier.

22. A method according to claim 21, where the pharmaceutical composition further comprises an angiotensin converting enzyme inhibitor.

23. A compound according to claim 1, which is

[2-(4-Bromo-2-fluoro-benzylcarbamoyl)-5-chloro-phenoxy]-acetic acid;

(2-Senzylcarbamoyl-5-chloro-phenoxy)-acetic acid;

[5-Chloro-2-(3-fluoro-benzylcarbarnoyl)-phenoxy]-acetic acid;

[5-Chloro-2-(3-trifluoromethyl-benzylcarbamoyl)-phenoxy]-acetic acid;

[2-(3-Nitro-benzylcarbamoyl)-5-chloro-phenoxy]-acetic acid;

[5-Chloro-2-(4-chloro-benzylcarbamoyl)-phenoxy]-acetic acid;

[2-(4-Bromo-benzylcarbamoyl)-5-chloro-phenoxy]-acetic acid;

[5-Chloro-2-(4-methoxy-benzylcarbamoyl)-phenoxy]-acetic acid; or

[5-Chloro-2-(4-trifluoromethoxy-benzylcarbamoyl)-phenoxy]-acetic acid.

24. A compound according to claim 1, which is

[5-Chloro-2-(2,6-difluoro-benzylcarbamoyl)-phenoxy]-acetic acid;

[5-Chloro-2-(3-fluoro-5-trifluoromethyl-benzylcarbamoyl)-phenoxy]acetic acid;

[2-(3,5-Bistrifluoromethyl-benzylcarbamoyl)-5-chloro-phenoxy]-acetic acid;

[5-Chloro-2-(3,5-dimethoxy-benzylcarbamoyl)-phenoxy]-acetic acid;

[5-Chloro-2-(3,4-dichloro-benzylcaybamoyl)-phenoxy]-acetic acid;

{2-[(Benzo[1,3]dioxol-5-ylmethyl)-carbamoyl]-5-chloro-phenosy}-acetic acid; or

[2-(4-Bromo-2-fluoro-benzylcarbamoyl)-5-methoxy-phenoxy]-acetic acid.

25. A compound according to claim 1, which is

[2-(4-Bromo-2-fluoro-benzylcarbamoyl)-4-chloro-phenoxy]-acetic acid;

[2-(4-Bromo-2-fluoro-benzylcarbamoyl)-4-fluoro-phenoxy]-acetic acid;

[2-(4-Bromo-2-fluoro-benzylcarbamoyl)-4-fluoro-phenoxy]-acetic acid;

[2-(4-Bromo-2-fluoro-benzylcarbamoyl)-4-methyl-phenoxy]-acetic acid;

[2-(4-Bromo-2-fluoro-benzylcarbamoyl)-4-nitro-phenoxy]-acetic acid;

[2-(4-Bromo-2-fluoro-benzylcarbamoyl)-4-nitro-phenoxy]-acetic acid; or

[2-(4-Bromo-2-fluoro-benzylcarbamoyl)-5-methyl-phenoxy]-acetic acid.

26. A compound according to claim 1, which is

[2-(4-Bromo-2-fluoro-benzylcarbamoyl)-phenoxy]-acetic acid;

[2-(4-Bromo-2-fluoro-benzylcarbamoyl)-5-methylsulfanyl-phenoxy]-acetic acid;

[2-(4-Bromo-2-fluoro-benzylcarbamoyl)-5-methylsylfanyl-phenoxy]-acetic acid;

[2-(3-Nitro-benzylcarbamoyl)-4-methyl-phenoxy]-acetic acid;

[2-(3-nicro-benzylcarbamoyl)-4-trifluoromrethoxy-phenoxy]-acetic acid; or

[5-Fluoro-2-(3-nitro-benzylcarbamoyl)-phenoxy]-acetic acid.

27. A compound according to claim 1, which is

[2-(4-Bromo-2-fluoro-benzylcarbamoyl)-5-fluoro-phenoxy]-acecic acid;

[5-Fluoro-2-(4-methyl-3-nitro-benzylcarbamoyl)-phenoxy]-acetic acid;

[2-(4-Bromo-2-fluoro-benzylcarbamoyl)-4,5-difluoro-phenoxy]-acetic acid;

[2-(4-Bromo-2-fluoro-benzylcarbamoyl)-3,5-difluoro-phenoxy]-acetic acid;

[2-(4-Bromo-2-fluoro-benzylcarbamoyl)-5-methanesulfonyl-phenoxy]-acetic acid;

[2-(4-Bromro-2-fluoro-benzylcarbamoyl)-5-merhanesulfonyl-phenoxy]-acetic acid;

[4-Amino-2-(4-bromo-2-fluoro-benzylcarbamoyl)-phenoxy]-acetic acid; or

[2-(4-Bromo-2-fluoro-benzylcarbamoyl)-4-mrethoxy-phenoxy]-acetic acid.

28. A compound according to claim 1, which is

[4-Acetylamino-2-(4-bromo-2-fluoro-benzylcarbamoyl)-phenoxy]-acetic acid;

[2-(4-Bromo-2-fluoro-benzylcarbamoyl)-5-trifluoromethyl-phenoxy]-acetic acid;

[4-Allyloxy-2-(4-bromo-2-fluoro-benzylcarbamoyl)-phenoxy]-acetic acid;

[4-Allyloxy-2-(4-bromo-2-fluoro-benzylcarbamoyl)-phenoxy]-acetic acid;

[2-(4-Bromo-2-fluoro-benzylcarbamoyl)-4-hydroxy-phenoxy]-acetic acid;

[2-(4-Bromo-2-fluoro-benzylcarbamoyl)-4-propoxy-phenoxy]-acetic acid; or

[2-(2-Eluoro-benzylcarbamoyl)-4-propoxy-phenoxy]-acetic acid.

29. A compound according to claim 1, which is [2-(4-Bromo-2-fluoro-benzylcarbamoyl)-5-fluoro-4-methyl-phenoxy]-acetic acid; [2-(3-Nitro-benzylcarbamoyl)-5-fluoro-4-methyl-phenoxy]-acetic acid; or [4-Bromo-5-fluoro-2-(3-nitro-benzylcarbamoyl)-phenoxy]-cetic acid.

30. A compound according to claim 1, which is

[4-Bromo-5-fluoro-2-(3-nitro-benzylcarbamoy1)-phenoxy]-acetic acid;

[5-(3-Nitro-benzylcarbamoyl)-2-fluoro-biphenyl-4-yloxy]-acetic acid;

[2-(3-Nitro-benzylcarbamoyl)-4-cyano-5-fluoro-phenoxy]-acetic acid; or

[2-(3-Nitro-benzylcarbanmoyl)-5-fluoro-4-morpholin-4-yl-phenoxy]-acetic acid; or

[2-(4-Bromo-2-fluoro-benzylcarbamoyl)-4-methoxy-phenoxy]-acetic acid.

\* \* \* \* \*